(12) United States Patent
Schmid et al.

(10) Patent No.: US 8,523,936 B2
(45) Date of Patent: Sep. 3, 2013

(54) EXPANDABLE SLIDE AND LOCK STENT

(75) Inventors: Eric Schmid, San Diego, CA (US);
Keith Weier, San Diego, CA (US);
Keith A. Esser, San Diego, CA (US);
Steven C. Howard, La Jolla, CA (US);
John Hobson, San Marcos, CA (US);
Craig Bonsignore, Pleasonton, CA (US)

(73) Assignee: REVA Medical, Inc., San Diego, CA (US)

( * ) Notice: Subject to any disclaimer, the term of this patent is extended or adjusted under 35 U.S.C. 154(b) by 53 days.

(21) Appl. No.: 13/083,508

(22) Filed: Apr. 8, 2011

(65) Prior Publication Data
US 2011/0251674 A1    Oct. 13, 2011

Related U.S. Application Data

(60) Provisional application No. 61/322,843, filed on Apr. 10, 2010.

(51) Int. Cl.
*A61F 2/06* (2006.01)
(52) U.S. Cl.
USPC ......... 623/1.22; 623/1.15; 623/1.2; 623/1.34; 623/1.38; 623/1.42; 623/1.43
(58) Field of Classification Search
USPC .................................................. 623/1.15
See application file for complete search history.

(56) References Cited

U.S. PATENT DOCUMENTS

| 2,361,506 | A | 10/1944 | Gray et al. |
| 3,620,218 | A | 11/1971 | Schmitt |
| 4,261,390 | A | 4/1981 | Belofsky |
| 4,383,555 | A | 5/1983 | Finley |
| 4,553,545 | A | 11/1985 | Maass et al. |
| 4,576,532 | A | 3/1986 | Hanson et al. |
| 4,714,508 | A | 12/1987 | Chivens et al. |
| 4,733,665 | A | 3/1988 | Palmaz |
| 4,739,762 | A | 4/1988 | Palmaz |
| 4,740,207 | A | 4/1988 | Kreamer |
| 4,748,982 | A | 6/1988 | Horzewski et al. |
| 4,762,129 | A | 8/1988 | Bonzel |

(Continued)

FOREIGN PATENT DOCUMENTS

| EP | 0712614 | 5/1996 |
| EP | 0756853 | 2/1997 |

(Continued)

OTHER PUBLICATIONS

International Search Report and Written Opinion, mailed Aug. 3, 2011 in related International Application No. PCT/US2011/031853, 12 pages.

(Continued)

*Primary Examiner* — David Isabella
*Assistant Examiner* — Jacqueline Woznicki
(74) *Attorney, Agent, or Firm* — Knobbe, Martens, Olson & Bear, LLP

(57) ABSTRACT

An expandable slide and lock stent comprises a tubular member that can be expanded from a collapsed state to an expanded state. The tubular member can comprise a reversing helical backbone and at least one rail member extending from the helical backbone in a circumferential direction. The backbone can have at least one engagement element that can be configured to receive a rail member to form the tubular member. In some embodiments, the reversing helical backbone can comprise a plurality of discrete segments having a variable profile and/or wave form.

22 Claims, 21 Drawing Sheets

(56) References Cited

U.S. PATENT DOCUMENTS

| | | |
|---|---|---|
| 4,776,337 A | 10/1988 | Palmaz |
| 4,788,751 A | 12/1988 | Shely et al. |
| 4,817,600 A | 4/1989 | Herms et al. |
| 4,877,030 A | 10/1989 | Beck et al. |
| 4,922,905 A | 5/1990 | Strecker |
| 4,954,126 A | 9/1990 | Wallstén |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,108,417 A | 4/1992 | Sawyer |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,314,472 A | 5/1994 | Fontaine |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A | 4/1995 | Oetiker |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneuer et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,456 A | 9/1998 | Maeda et al. |
| 5,800,507 A | 9/1998 | Schwartz |
| 5,833,707 A | 11/1998 | McIntyre et al. |
| 5,836,965 A | 11/1998 | Jendersee et al. |
| 5,849,034 A | 12/1998 | Schwartz |
| 5,851,217 A | 12/1998 | Wolff et al. |
| 5,851,231 A | 12/1998 | Wolff et al. |
| 5,855,600 A | 1/1999 | Alt |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,957,975 A | 9/1999 | Lafont et al. |
| 5,976,181 A | 11/1999 | Whelan et al. |
| 5,984,963 A | 11/1999 | Ryan et al. |
| 5,989,280 A | 11/1999 | Euteneur et al. |
| 6,007,545 A | 12/1999 | Venturelli |
| 6,015,387 A | 1/2000 | Schwartz et al. |
| 6,019,779 A | 2/2000 | Thorud et al. |
| 6,019,785 A | 2/2000 | Strecker |
| 6,033,436 A | 3/2000 | Steinke et al. |
| 6,036,715 A | 3/2000 | Yock |
| 6,048,521 A | 4/2000 | Kohn et al. |
| 6,059,825 A | 5/2000 | Hobbs et al. |
| 6,063,111 A | 5/2000 | Hieshima et al. |
| 6,080,190 A | 6/2000 | Schwartz |
| 6,080,191 A | 6/2000 | Summers |
| 6,093,157 A | 7/2000 | Chandrasekaran |
| 6,120,491 A | 9/2000 | Kohn et al. |
| 6,125,523 A | 10/2000 | Brown et al. |
| 6,132,457 A | 10/2000 | Chobotov |
| 6,156,062 A | 12/2000 | McGuiness |
| 6,159,239 A | 12/2000 | Greenhalgh |
| 6,160,084 A | 12/2000 | Langer et al. |
| 6,171,334 B1 | 1/2001 | Cox |
| 6,174,328 B1 | 1/2001 | Cragg |
| 6,179,878 B1 | 1/2001 | Duerig et al. |
| 6,183,503 B1 | 2/2001 | Hart et al. |
| 6,190,403 B1 | 2/2001 | Fischell et al. |
| 6,197,789 B1 | 3/2001 | Grainger et al. |
| 6,214,037 B1 | 4/2001 | Mitchell et al. |
| 6,224,626 B1 | 5/2001 | Steinke |
| 6,238,430 B1 | 5/2001 | Klumb et al. |
| 6,258,117 B1 | 7/2001 | Camrud et al. |
| 6,262,079 B1 | 7/2001 | Grainger et al. |

| Patent Number | Date | Inventor |
|---|---|---|
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |
| 6,284,862 B1 | 9/2001 | Kohn et al. |
| 6,287,329 B1 | 9/2001 | Duerig et al. |
| 6,287,333 B1 | 9/2001 | Appling et al. |
| 6,302,907 B1 | 10/2001 | Hijlkema |
| 6,309,350 B1 | 10/2001 | Van Tassel et al. |
| 6,319,277 B1 | 11/2001 | Rudnick et al. |
| 6,319,492 B1 | 11/2001 | Kohn et al. |
| 6,322,586 B1 | 11/2001 | Monroe et al. |
| 6,350,277 B1 | 2/2002 | Kocur |
| 6,359,102 B1 | 3/2002 | Kemnitzer et al. |
| 6,361,558 B1 | 3/2002 | Hieshima et al. |
| 6,383,211 B1 | 5/2002 | Staehle |
| 6,388,043 B1 | 5/2002 | Langer et al. |
| 6,391,032 B2 | 5/2002 | Blaeser et al. |
| 6,406,490 B1 | 6/2002 | Roth |
| 6,409,750 B1 | 6/2002 | Hyodoh et al. |
| 6,409,751 B1 | 6/2002 | Hall et al. |
| 6,409,752 B1 | 6/2002 | Boatman et al. |
| 6,425,915 B1 | 7/2002 | Khosravi et al. |
| 6,447,508 B1 | 9/2002 | Sharkey et al. |
| 6,451,034 B1 | 9/2002 | Gifford, III et al. |
| 6,458,152 B1 | 10/2002 | Khosravi et al. |
| 6,475,477 B1 | 11/2002 | Kohn et al. |
| 6,485,510 B1 | 11/2002 | Camrud et al. |
| 6,488,700 B2 | 12/2002 | Klumb et al. |
| 6,491,704 B2 | 12/2002 | Gifford, III et al. |
| 6,491,705 B2 | 12/2002 | Gifford, III et al. |
| 6,491,938 B2 | 12/2002 | Kunz et al. |
| 6,497,671 B2 | 12/2002 | Ferrera et al. |
| 6,527,791 B2 | 3/2003 | Fisher |
| 6,530,940 B2 | 3/2003 | Fisher |
| 6,530,958 B1 | 3/2003 | Cima et al. |
| 6,562,021 B1 | 5/2003 | Derbin et al. |
| 6,565,582 B2 | 5/2003 | Gifford, III et al. |
| 6,565,596 B1 | 5/2003 | White et al. |
| 6,569,191 B1 | 5/2003 | Hogan |
| 6,569,441 B2 | 5/2003 | Kunz et al. |
| 6,582,458 B1 | 6/2003 | White et al. |
| 6,582,472 B2 | 6/2003 | Hart |
| 6,585,760 B1 | 7/2003 | Fogarty |
| 6,602,497 B1 | 8/2003 | Kohn et al. |
| 6,607,551 B1 | 8/2003 | Sullivan et al. |
| 6,610,086 B1 | 8/2003 | Kock et al. |
| 6,613,073 B1 | 9/2003 | White et al. |
| 6,620,356 B1 | 9/2003 | Wong et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,645,143 B2 | 11/2003 | Van Tassel et al. |
| 6,652,555 B1 | 11/2003 | Van Tassel et al. |
| 6,659,105 B2 | 12/2003 | Burbank et al. |
| 6,676,658 B2 | 1/2004 | Burbank et al. |
| 6,682,541 B1 | 1/2004 | Gifford, III et al. |
| 6,685,736 B1 | 2/2004 | White et al. |
| 6,689,153 B1 | 2/2004 | Skiba |
| 6,689,158 B1 | 2/2004 | White et al. |
| 6,695,857 B2 | 2/2004 | Gifford, III et al. |
| 6,699,257 B2 | 3/2004 | Gifford, III et al. |
| 6,699,280 B2 | 3/2004 | Camrud et al. |
| 6,702,846 B2 | 3/2004 | Mikus et al. |
| 6,709,449 B2 | 3/2004 | Camrud et al. |
| 6,720,402 B2 | 4/2004 | Langer et al. |
| 6,736,838 B1 | 5/2004 | Richter |
| 6,736,844 B1 | 5/2004 | Glatt et al. |
| 6,746,477 B2 | 6/2004 | Moore |
| 6,749,627 B2 | 6/2004 | Thompson et al. |
| 6,786,922 B2 | 9/2004 | Schaeffer |
| 6,790,221 B2 | 9/2004 | Monroe et al. |
| 6,792,979 B2 | 9/2004 | Konya et al. |
| 6,802,849 B2 | 10/2004 | Blaeser et al. |
| 6,821,292 B2 | 11/2004 | Pazienza et al. |
| 6,852,308 B2 | 2/2005 | Kohn et al. |
| 6,869,143 B2 | 3/2005 | Secord |
| 6,878,159 B2 | 4/2005 | Iwasaka et al. |
| 6,878,162 B2 | 4/2005 | Bales et al. |
| 6,916,868 B2 | 7/2005 | Kemnitzer et al. |
| 6,929,709 B2 | 8/2005 | Smith |
| 6,951,053 B2 | 10/2005 | Padilla et al. |
| 6,962,604 B2 | 11/2005 | Hijlkema |
| 6,964,680 B2 | 11/2005 | Shanley |
| 6,974,472 B2 | 12/2005 | Hong et al. |
| 6,974,475 B1 | 12/2005 | Wall |
| 6,991,647 B2 | 1/2006 | Jadhav |
| 7,041,126 B2 | 5/2006 | Shin et al. |
| 7,056,493 B2 | 6/2006 | Kohn et al. |
| 7,077,860 B2 | 7/2006 | Yan et al. |
| 7,128,756 B2 | 10/2006 | Lowe et al. |
| 7,141,063 B2 | 11/2006 | White et al. |
| 7,175,653 B2 | 2/2007 | Gaber |
| 7,229,473 B2 | 6/2007 | Falotico et al. |
| 7,255,710 B2 | 8/2007 | White et al. |
| 7,279,664 B2 | 10/2007 | Weber |
| 7,329,277 B2 | 2/2008 | Addonizio et al. |
| 7,476,232 B2 | 1/2009 | Deal |
| 7,520,893 B2 | 4/2009 | Rivelli |
| 7,553,377 B1 | 6/2009 | Chen et al. |
| 7,556,644 B2 | 7/2009 | Burpee et al. |
| 7,637,939 B2 | 12/2009 | Tischler |
| 7,704,275 B2 | 4/2010 | Schmid et al. |
| 7,722,662 B2 | 5/2010 | Steinke et al. |
| 7,763,065 B2 | 7/2010 | Schmid et al. |
| 7,763,067 B2 | 7/2010 | Bales et al. |
| 7,766,960 B2 | 8/2010 | Alexander et al. |
| 7,780,721 B2 | 8/2010 | Bales et al. |
| 7,812,290 B2 | 10/2010 | Weber |
| 7,846,198 B2 | 12/2010 | Hogendijk |
| 7,947,071 B2 | 5/2011 | Schmid |
| 7,988,721 B2 | 8/2011 | Morris et al. |
| 8,172,894 B2 | 5/2012 | Schmid et al. |
| 8,277,500 B2 | 10/2012 | Schmid et al. |
| 8,292,944 B2 | 10/2012 | Schmid et al. |
| 2001/0010015 A1 | 7/2001 | Hijlkema |
| 2001/0020173 A1 | 9/2001 | Klumb et al. |
| 2001/0029378 A1 | 10/2001 | Blaeser et al. |
| 2001/0044651 A1 | 11/2001 | Steinke et al. |
| 2002/0010504 A1 | 1/2002 | Alt et al. |
| 2002/0040238 A1 | 4/2002 | Rudnick et al. |
| 2002/0052641 A1 | 5/2002 | Monroe et al. |
| 2002/0072656 A1 | 6/2002 | Van Tassel et al. |
| 2002/0077693 A1 | 6/2002 | Barclay et al. |
| 2002/0082682 A1 | 6/2002 | Barclay et al. |
| 2002/0095204 A1 | 7/2002 | Thompson et al. |
| 2002/0099431 A1 | 7/2002 | Armstrong et al. |
| 2002/0111669 A1 | 8/2002 | Pazienza et al. |
| 2002/0116044 A1 | 8/2002 | Cottone et al. |
| 2002/0120322 A1 | 8/2002 | Thompson et al. |
| 2002/0120323 A1 | 8/2002 | Thompson et al. |
| 2002/0123791 A1 | 9/2002 | Harrison |
| 2002/0138081 A1 | 9/2002 | Blaeser et al. |
| 2002/0138126 A1 | 9/2002 | Camrud et al. |
| 2002/0147489 A1 | 10/2002 | Hong et al. |
| 2002/0151967 A1 | 10/2002 | Mikus et al. |
| 2002/0156456 A1 | 10/2002 | Fisher |
| 2002/0156457 A1 | 10/2002 | Fisher |
| 2002/0193870 A1 | 12/2002 | Jang |
| 2003/0045923 A1 | 3/2003 | Bashiri |
| 2003/0069633 A1 | 4/2003 | Richter et al. |
| 2003/0074043 A1 | 4/2003 | Thompson |
| 2003/0078649 A1 | 4/2003 | Camrud et al. |
| 2003/0120334 A1 | 6/2003 | Gerberding |
| 2003/0176914 A1 | 9/2003 | Rabkin et al. |
| 2003/0199969 A1 | 10/2003 | Steinke et al. |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0024446 A1 | 2/2004 | Smith |
| 2004/0044401 A1 | 3/2004 | Bales et al. |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |

| | | | | | | |
|---|---|---|---|---|---|---|
| 2004/0093076 A1 | 5/2004 | White et al. | JP | 2007-185363 | 7/2007 | |
| 2004/0097959 A1 | 5/2004 | Thompson | WO | WO 90/14046 A1 | 11/1990 | |
| 2004/0106971 A1 | 6/2004 | Schwartz et al. | WO | WO 94/21196 A2 | 9/1994 | |
| 2004/0106977 A1 | 6/2004 | Sullivan et al. | WO | WO 94/21196 A3 | 2/1995 | |
| 2004/0133260 A1 | 7/2004 | Schwartz et al. | WO | WO 96/14030 A1 | 5/1996 | |
| 2004/0143319 A1 | 7/2004 | Schwartz et al. | WO | WO 97/07751 A1 | 3/1997 | |
| 2004/0167616 A1 | 8/2004 | Camrud et al. | WO | WO 97/42911 A1 | 11/1997 | |
| 2004/0186551 A1 | 9/2004 | Kao et al. | WO | WO 98/22045 | 5/1998 | |
| 2004/0186556 A1 | 9/2004 | Hogendijk et al. | WO | WO 98/22073 A2 | 5/1998 | |
| 2004/0186557 A1 | 9/2004 | Gambale et al. | WO | WO 98/41169 A1 | 9/1998 | |
| 2004/0191175 A1 | 9/2004 | Kohn et al. | WO | WO 98/22073 A3 | 2/1999 | |
| 2004/0193251 A1 | 9/2004 | Rudnick et al. | WO | WO 99/08740 A1 | 2/1999 | |
| 2004/0224003 A1 | 11/2004 | Schultz | WO | WO 99/15106 A1 | 4/1999 | |
| 2004/0236401 A1 | 11/2004 | Shin et al. | WO | WO 99/40874 A1 | 8/1999 | |
| 2004/0243217 A1 | 12/2004 | Andersen et al. | WO | WO 99/65421 A2 | 12/1999 | |
| 2004/0243218 A1 | 12/2004 | Schaeffer | WO | WO 99/65421 A3 | 1/2000 | |
| 2005/0038497 A1 | 2/2005 | Neuendorf et al. | WO | WO 00/09195 A1 | 2/2000 | |
| 2005/0038503 A1 | 2/2005 | Greenhalgh et al. | WO | WO 00/10623 A1 | 3/2000 | |
| 2005/0106119 A1 | 5/2005 | Brandom et al. | WO | WO 00/30565 A1 | 6/2000 | |
| 2005/0123481 A1 | 6/2005 | Kohn et al. | WO | WO 00/59405 A1 | 10/2000 | |
| 2005/0165203 A1 | 7/2005 | Kohn et al. | WO | WO 00/62708 A1 | 10/2000 | |
| 2005/0203615 A1 | 9/2005 | Forster et al. | WO | WO 00/71058 A1 | 11/2000 | |
| 2005/0216076 A1 | 9/2005 | Kveen et al. | WO | WO 01/24735 A1 | 4/2001 | |
| 2005/0246010 A1 | 11/2005 | Alexander et al. | WO | WO 01/35864 A1 | 5/2001 | |
| 2006/0020324 A1 | 1/2006 | Schmid et al. | WO | WO 01/51114 A2 | 7/2001 | |
| 2006/0024266 A1 | 2/2006 | Brandom et al. | WO | WO 01/70298 A2 | 9/2001 | |
| 2006/0026815 A1 | 2/2006 | Padilla et al. | WO | WO 01/87180 A2 | 11/2001 | |
| 2006/0030934 A1 | 2/2006 | Hogendijk et al. | WO | WO 01/51114 A3 | 1/2002 | |
| 2006/0034769 A1 | 2/2006 | Kohn et al. | WO | WO 01/70298 A3 | 2/2002 | |
| 2006/0036316 A1 | 2/2006 | Zeltinger et al. | WO | WO 00/62708 C2 | 6/2002 | |
| 2006/0079955 A1 | 4/2006 | Brown | WO | WO 01/87180 A3 | 6/2002 | |
| 2006/0115449 A1 | 6/2006 | Pacetti | WO | WO 02/47582 A2 | 6/2002 | |
| 2006/0136041 A1 | 6/2006 | Schmid et al. | WO | WO 02/053204 A2 | 7/2002 | |
| 2006/0182779 A1 | 8/2006 | Brandom et al. | WO | WO 02/054990 A2 | 7/2002 | |
| 2006/0204440 A1 | 9/2006 | Kohn et al. | WO | WO 02/047582 A3 | 10/2002 | |
| 2007/0010870 A1 | 1/2007 | Alt et al. | WO | WO 02/054990 A3 | 11/2002 | |
| 2007/0032854 A1 | 2/2007 | Schmid et al. | WO | WO 02/053204 A3 | 3/2003 | |
| 2007/0032857 A1 | 2/2007 | Schmid et al. | WO | WO 03/022178 A1 | 3/2003 | |
| 2007/0061004 A1 | 3/2007 | Steinke | WO | WO 03/047464 A2 | 6/2003 | |
| 2007/0142901 A1 | 6/2007 | Steinke | WO | WO 03/057076 A1 | 7/2003 | |
| 2007/0250148 A1 | 10/2007 | Perry et al. | WO | WO 03/047464 A3 | 9/2003 | |
| 2007/0270939 A1 | 11/2007 | Hood et al. | WO | WO 03/047464 C2 | 11/2003 | |
| 2008/0046066 A1 | 2/2008 | Jenson et al. | WO | WO 03/094798 A1 | 11/2003 | |
| 2008/0051868 A1 | 2/2008 | Cottone et al. | WO | WO 03/099161 A2 | 12/2003 | |
| 2008/0051873 A1 | 2/2008 | Cottone et al. | WO | WO 2003/099161 A3 | 2/2004 | |
| 2008/0051874 A1 | 2/2008 | Cottone et al. | WO | WO 2004/019820 A1 | 3/2004 | |
| 2008/0051875 A1 | 2/2008 | Cottone et al. | WO | WO 2004/026112 A2 | 4/2004 | |
| 2008/0071355 A1 | 3/2008 | Weber | WO | WO 2004/032803 A1 | 4/2004 | |
| 2008/0103584 A1 | 5/2008 | Su et al. | WO | WO 2004/026112 C2 | 6/2004 | |
| 2008/0114391 A1 | 5/2008 | Dieck et al. | WO | WO 2004/026112 A3 | 10/2004 | |
| 2008/0183275 A1 | 7/2008 | Schmid et al. | WO | WO 2004/087015 | 10/2004 | |
| 2008/0195190 A1 | 8/2008 | Bland et al. | WO | WO 2004/096340 A1 | 11/2004 | |
| 2008/0221664 A1 | 9/2008 | Bales et al. | WO | WO 2004/110312 A1 | 12/2004 | |
| 2008/0221665 A1 | 9/2008 | Peckham et al. | WO | WO 2006/010636 A1 | 2/2006 | |
| 2008/0262599 A1 | 10/2008 | Caro et al. | WO | WO 2006/014596 A1 | 2/2006 | |
| 2008/0269869 A1 | 10/2008 | Cho | WO | WO 2006/014699 | 2/2006 | |
| 2008/0288050 A1 | 11/2008 | Addonizio et al. | WO | WO 2006/020616 A1 | 2/2006 | |
| 2009/0030501 A1 | 1/2009 | Morris et al. | WO | WO 2006/107608 A1 | 10/2006 | |
| 2009/0143853 A1 | 6/2009 | Morris et al. | WO | WO 2007/084444 A2 | 7/2007 | |
| 2009/0187239 A1 | 7/2009 | Goto | WO | WO 2010/022005 A1 | 2/2010 | |
| 2010/0004725 A1 | 1/2010 | Zipse et al. | WO | WO 2010/042879 A2 | 4/2010 | |
| 2010/0042203 A1 | 2/2010 | Cottone et al. | WO | WO 2011/127452 | 10/2011 | |
| 2010/0114297 A1 | 5/2010 | Calisse | | | | |
| 2010/0131048 A1 | 5/2010 | Schmid et al. | | | | |
| 2010/0256735 A1 | 10/2010 | Morales | | | | |
| 2010/0280593 A1 | 11/2010 | Richter | | | | |
| 2010/0286759 A1 | 11/2010 | Taylor et al. | | | | |
| 2010/0292773 A1 | 11/2010 | Schmid et al. | | | | |
| 2010/0324662 A1 | 12/2010 | Addonizio et al. | | | | |
| 2011/0172759 A1 | 7/2011 | Schmid et al. | | | | |
| 2011/0245909 A1 | 10/2011 | Schmid et al. | | | | |
| 2011/0282434 A1 | 11/2011 | Morris et al. | | | | |
| 2012/0221097 A1 | 8/2012 | Schmid et al. | | | | |

FOREIGN PATENT DOCUMENTS

| | | |
|---|---|---|
| JP | 07-000531 | 1/1995 |
| JP | 08-196641 | 8/1996 |
| JP | 08-336598 | 12/1996 |
| JP | 9-313617 | 12/1997 |

OTHER PUBLICATIONS

Balcon, R. et al., *Recommendations on stent manufacture, implantation and utilization*, European Heart Journal, Oct. 1997, vol. 18, pp. 1536-1547.

Charles, Roger et al., *Ceramide-Coated Balloon Catheters Limit Neointimal Hyperplasia After Stretch Injury in Carotid Arteries*, Circulation Research, 2000; 87; pp. 282-288.

Coroneos, Emmanuel et al., *Differential Regulation of Sphingomyelinase and Ceramidase Activities by Growth Factors and Cytokines*, The Journal of Biological Chemistry, Oct. 6, 1995, vol. 270, No. 40, pp. 23305-23309.

Coroneos, Emmanuel et al., *Sphingolipid metabolites differentially regulate extracellular signal-regulated kinase and stress-activated protein kinase cascades*, Biochem. J., 1196; 316, pp. 13-17 (Printed in Great Britain).

Jacobs, Leila S. et al., *Sphingolipids as mediators of effects of platelet-derived growth factor in vascular smooth muscle cells*, Am J Physiol (American Physiological Society), 1993, pp. C740-C747.

Tanguay, Jean Francois et al., *Current Status of Biodegradable Stents*, Cardiology Clinics, Contemporary Interventional Techniques, Nov. 1994, vol. 12, No. 4, pp. 699-713, W.B. Saunders Company.

Nikol, S. et al., *Molecular biology and post-angioplasty restenosis*, Atherosclerosis, 1996; 123, pp. 17-31.

Phillips, Paul S. MD, et al., *The Stenter's Notebook*, 1998, (entire book), Physicians' Press, Birmingham, Michigan.

Ratner, Buddy D. et al., *Biomaterials Science, An Introduction to Materials in Medicine, 2nd Edition*, 2004, (entire book), Elsevier Academic Press.

Serruys, Patrick W. et al., *Handbook of Coronary Stents, Fourth Edition*, 2002, (entire book), Martin Dunitz Ltd.

Atala, Anthony et al., *Synthetic Biodegradable Polymer Scaffolds*, 1997, (entire book), Birkhauser Boston.

Asahara, T. "Local delivery of vascular endothelial growth factor accelerates reendothelialization and attenuates intimal hyperplasia in balloon-insured rate carotid artery," *Circulation* 91: 2793-2801, 1995.

Autieri, M.V. et al. "Antisense oligonucleotides to the p65 subunit of NF-Kb inhibit human vascular smooth muscle cell adherence and proliferation and prevent neointima formation in rat carotid arteries," *Biochemical and Biophysical Research Communications* 213: 827-836, 1995.

Brauner, R. "Controlled periadverntitial administration of verapamil inhibits neointimal smooth muscle cell proliferation and ameliorates vasomotor abnormalities in experimental vein bypass grafts," *The Journal of Thoracic and Cardiovascular Surgery* 114: 53-63, 1997.

Carmeliet, P. et al. "Inhibitory role of plasminogen activator inhibitor-1 in arterial wound healing and neointima formation," *Circulation* 96: 3180-3191, 1997.

Epstein, S.E. et al. "Cytotoxic effects of a recombinant chimeric toxin on rapidly proliferating vascular smooth muscle cells," *Circulation* 84: 778-787, 1991.

Hu, Y. "Inhibition of neointima hyperplasia of mouse vein grafts by locally applied suramin," *Circulation* 100: 861-868, 1999.

Kurisu, Y. et al. "Protective effect of beraprost sodium, a stable prostacyclin analogue, on cardiac allograft vasculopathy in rats," *Hiroshima Journal of Medical Science* 56: 11-19, 1997.

Morishita, R. et al. "Novel in vitro gene transfer method for study of local modulators in vascular smooth muscle cells," *Hypertension* 21: 894-899, 1993.

Nerem, R.M. et al. "Tissue engineering and the vascular system, synthetic biodegradable polymer scaffolds," pp. 164-185, 1997.

Von Der Leyen, H.E. et al. "Gene therapy neointimal vascular lesion: in vivo transfer of endothelial cell nitric oxide synthase gene," *PNAS USA* 92:1137-1141, 1995.

Yasukawa, H. "Inhibition of intimal hyperplasia after balloon injury by antibodies to intercellular adhesion molecule-1 and lymphocyte function, Associated antigen-1," *Circulation* 95: 1515-1522, 1997.

International Preliminary Report on Patentability, issued Oct. 16, 2012 in related International Application No. PCT/US2011/031853, 7 pages.

Communication Pursuant to Rules 161(1) and 162 EPC, dated Nov. 16, 2012 in corresponding European Application No. 11715815.4, 2 pages.

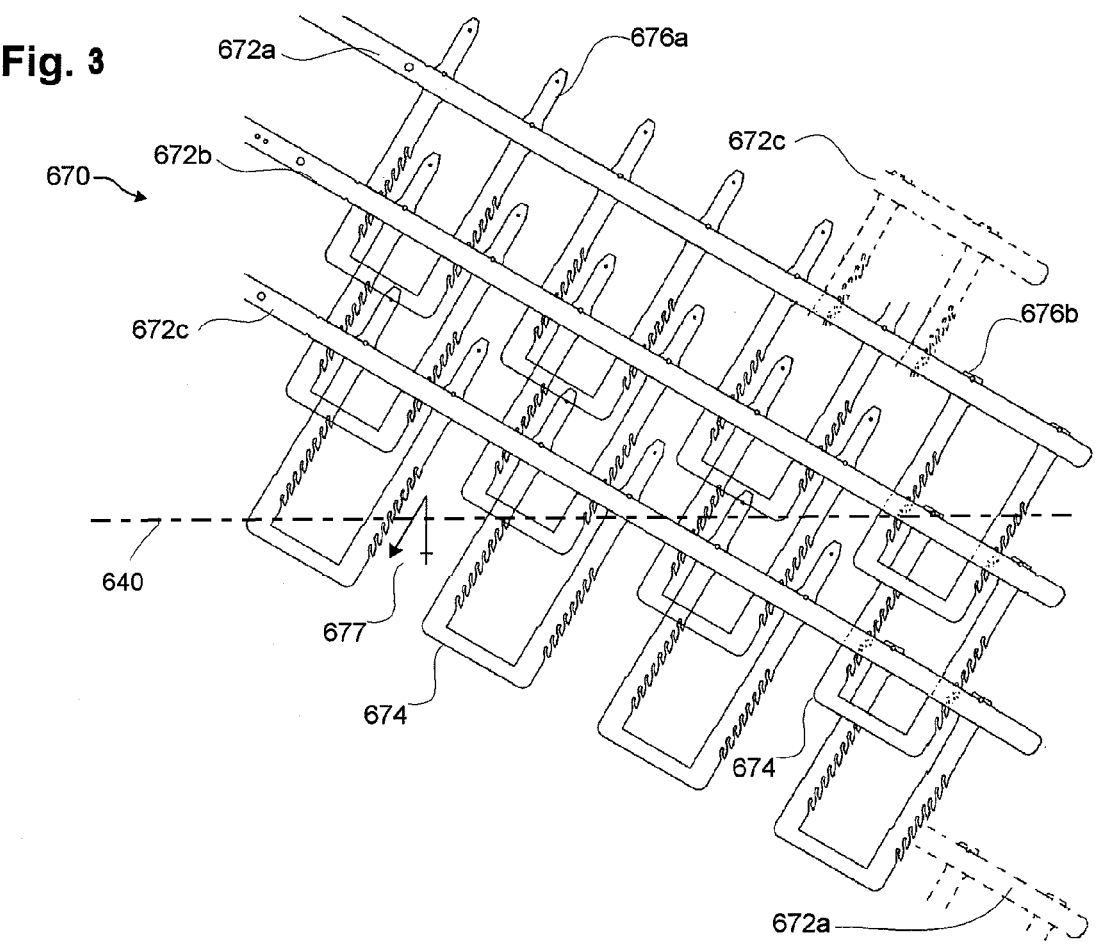

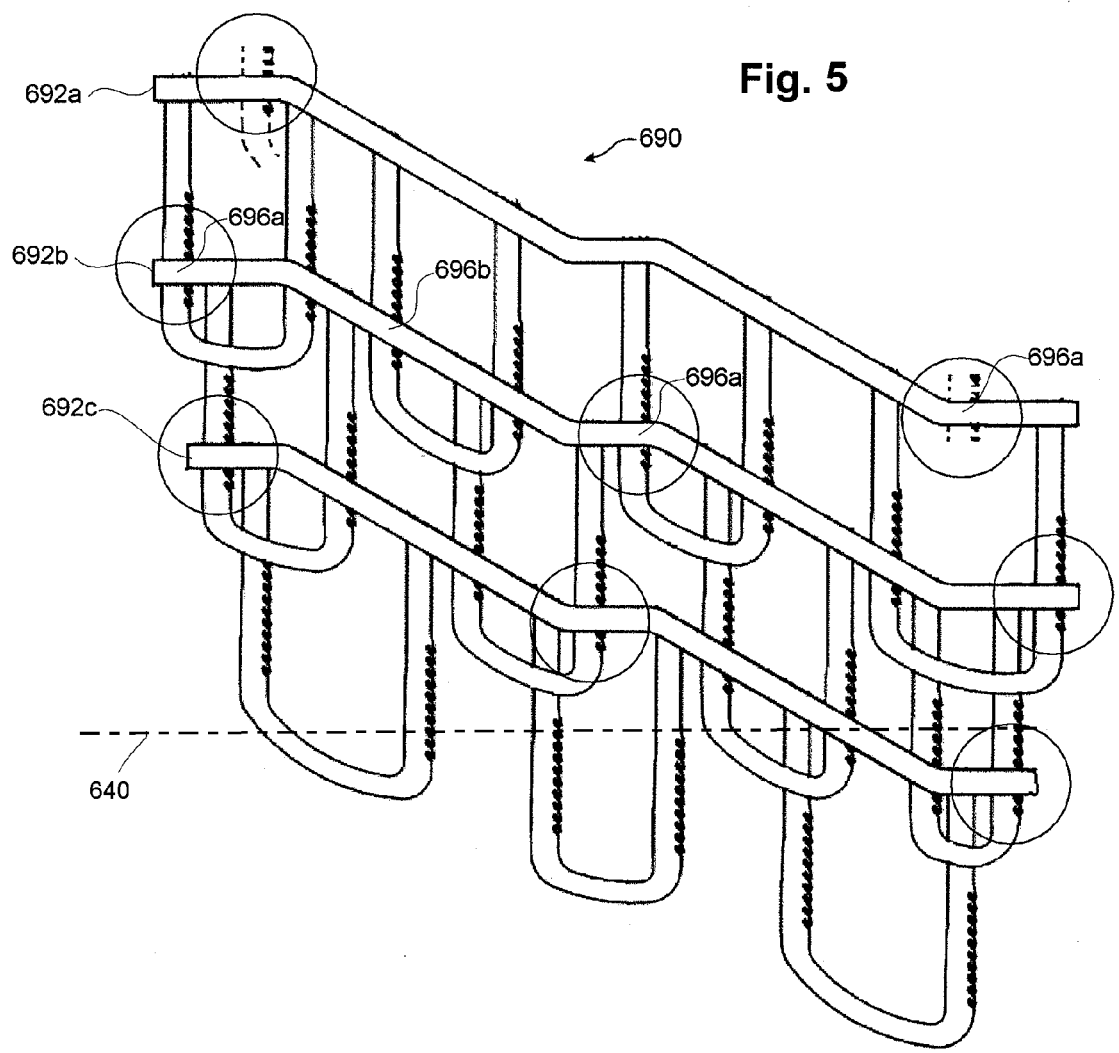

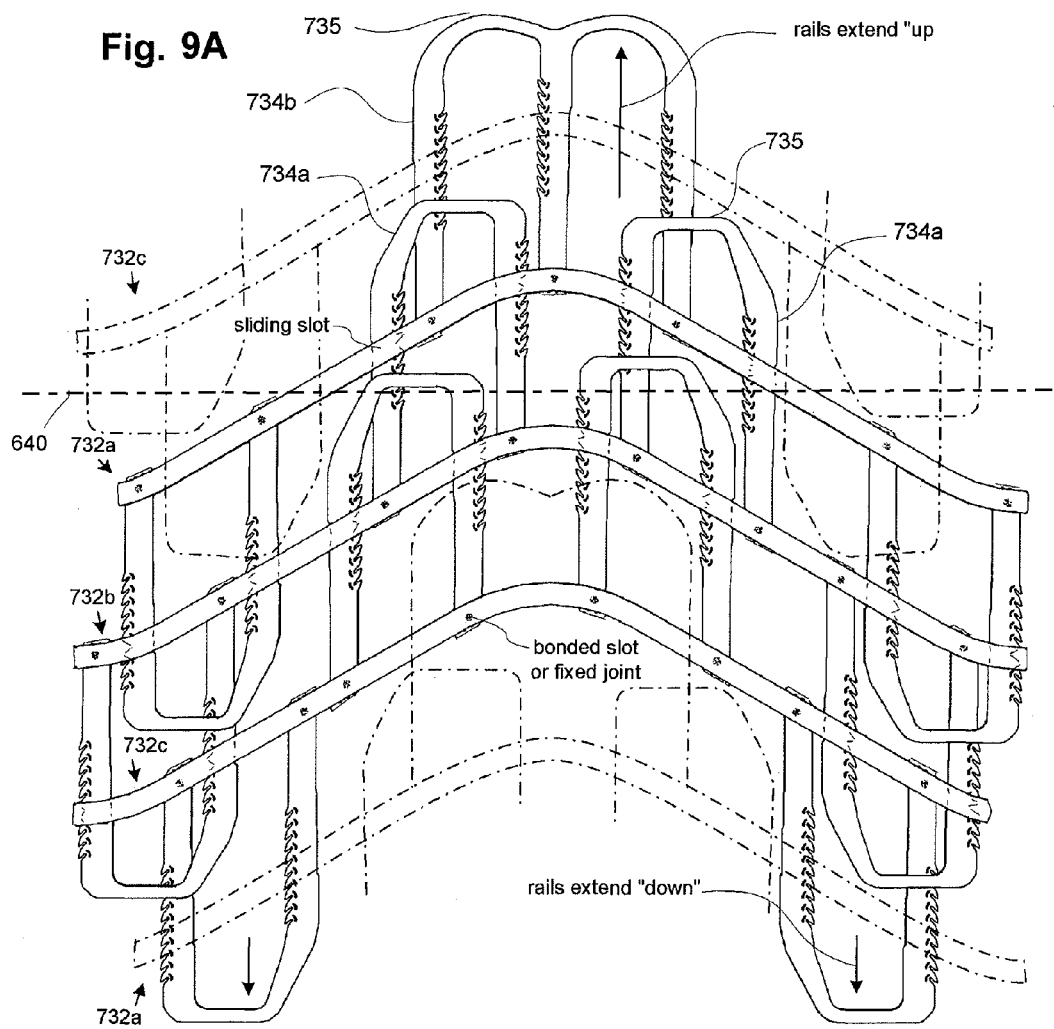

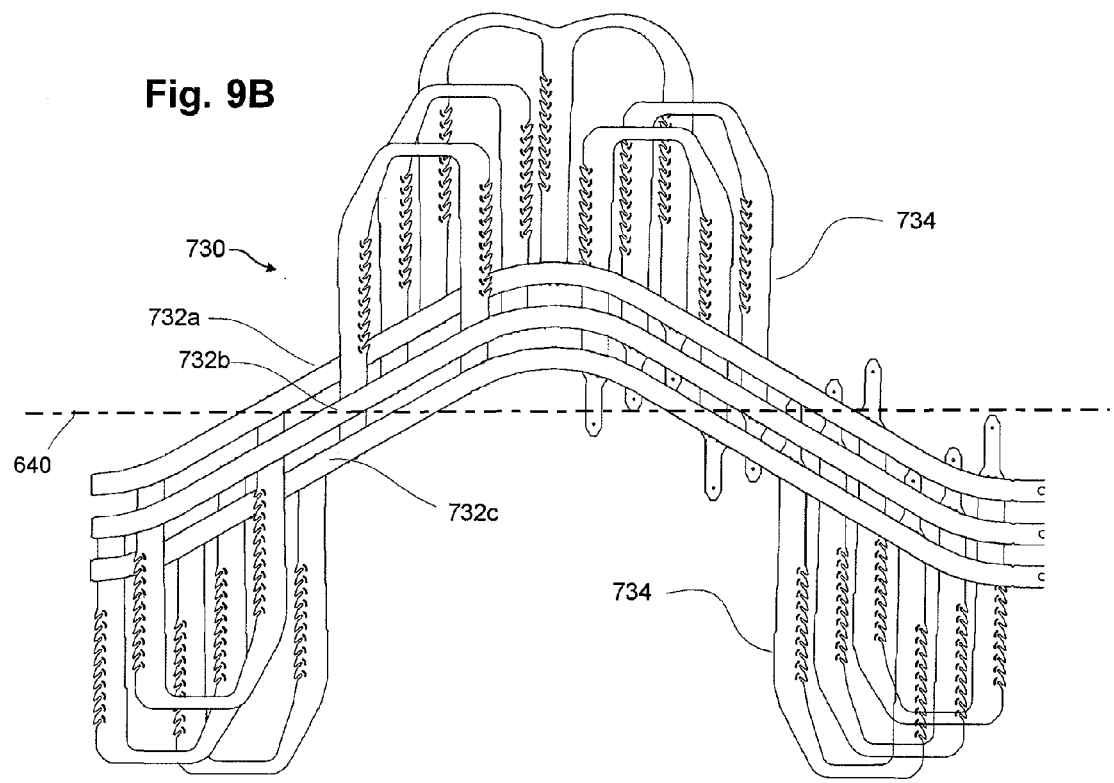

Figs. 10 A-F
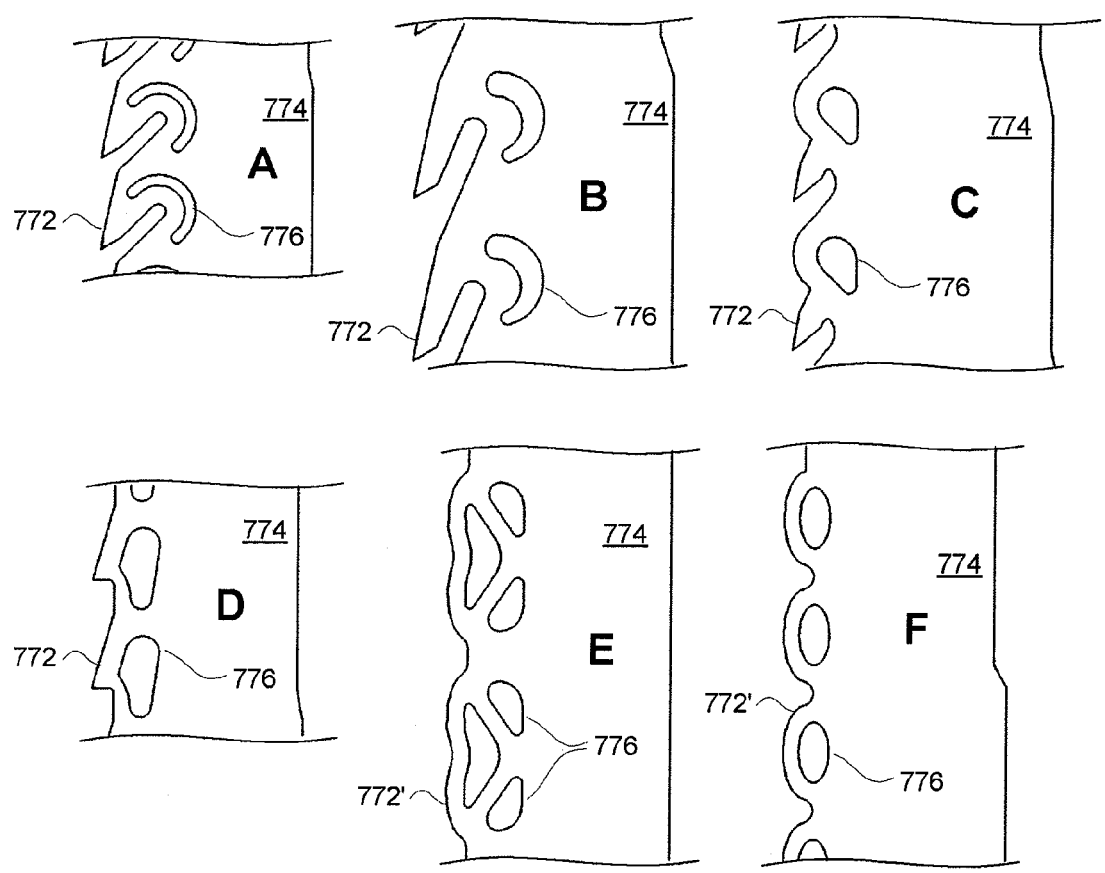

Fig. 11A
Fig. 11B
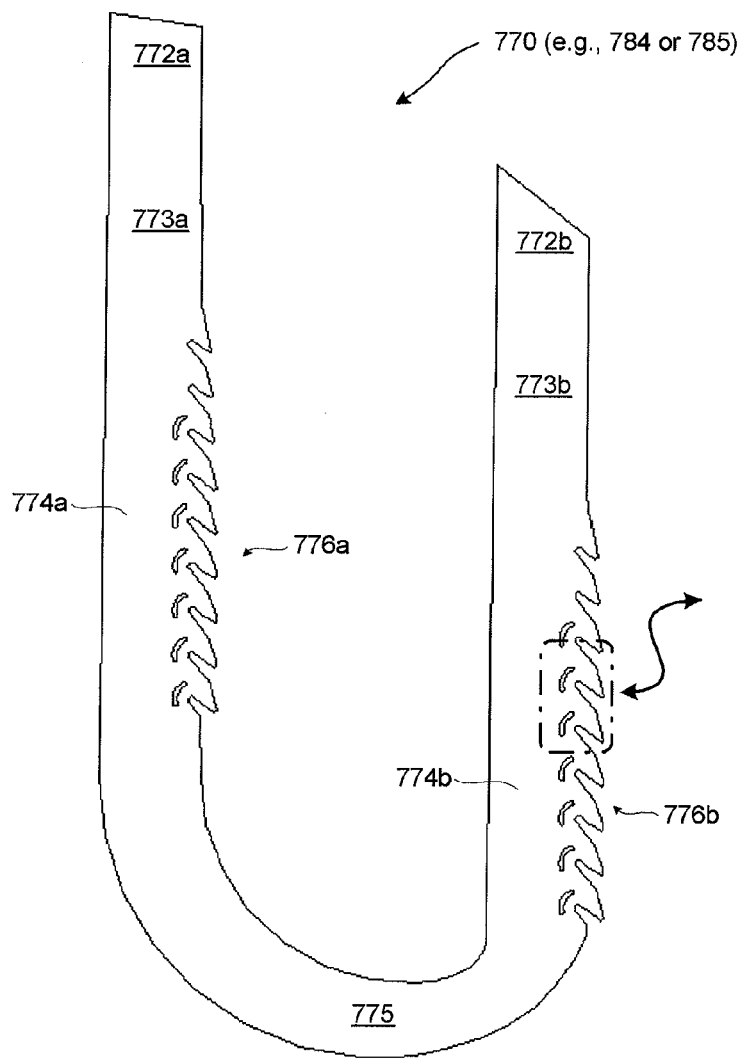
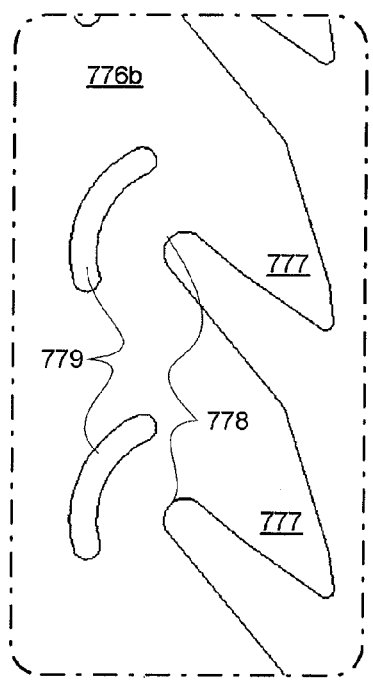

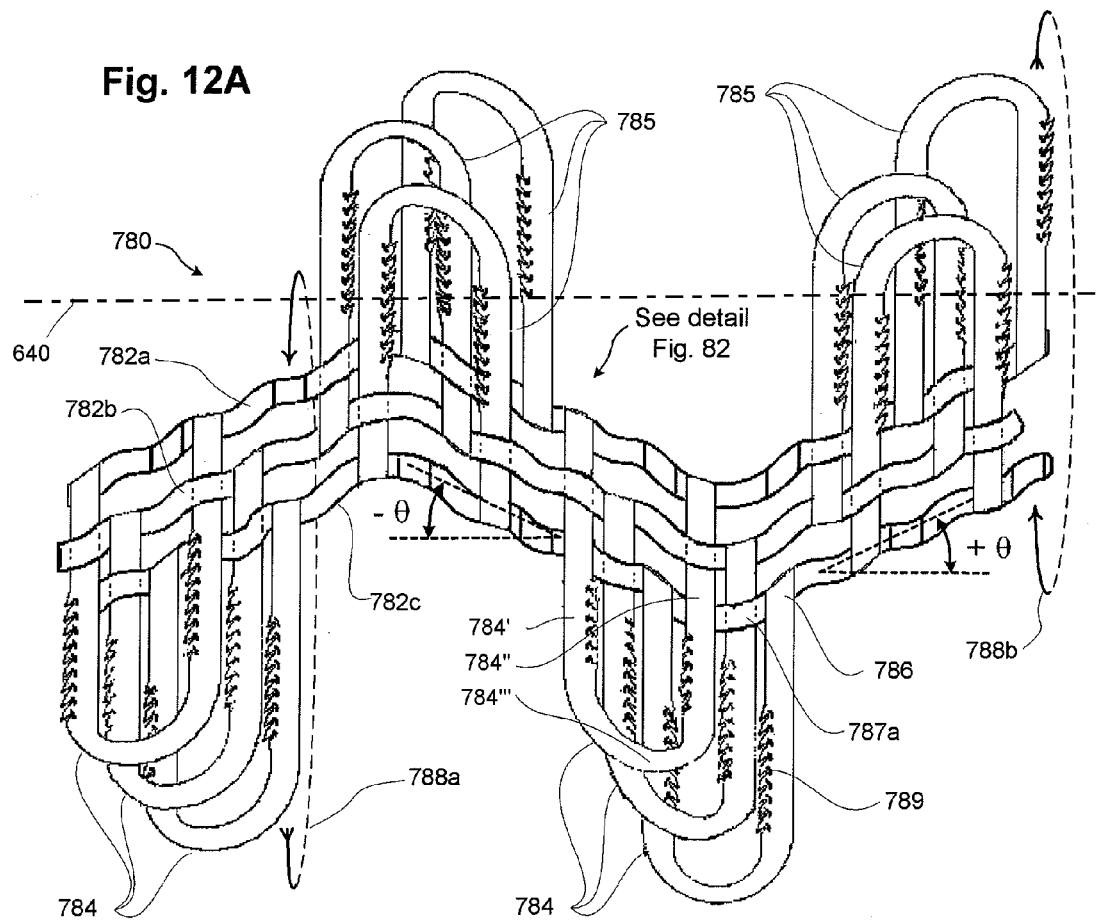

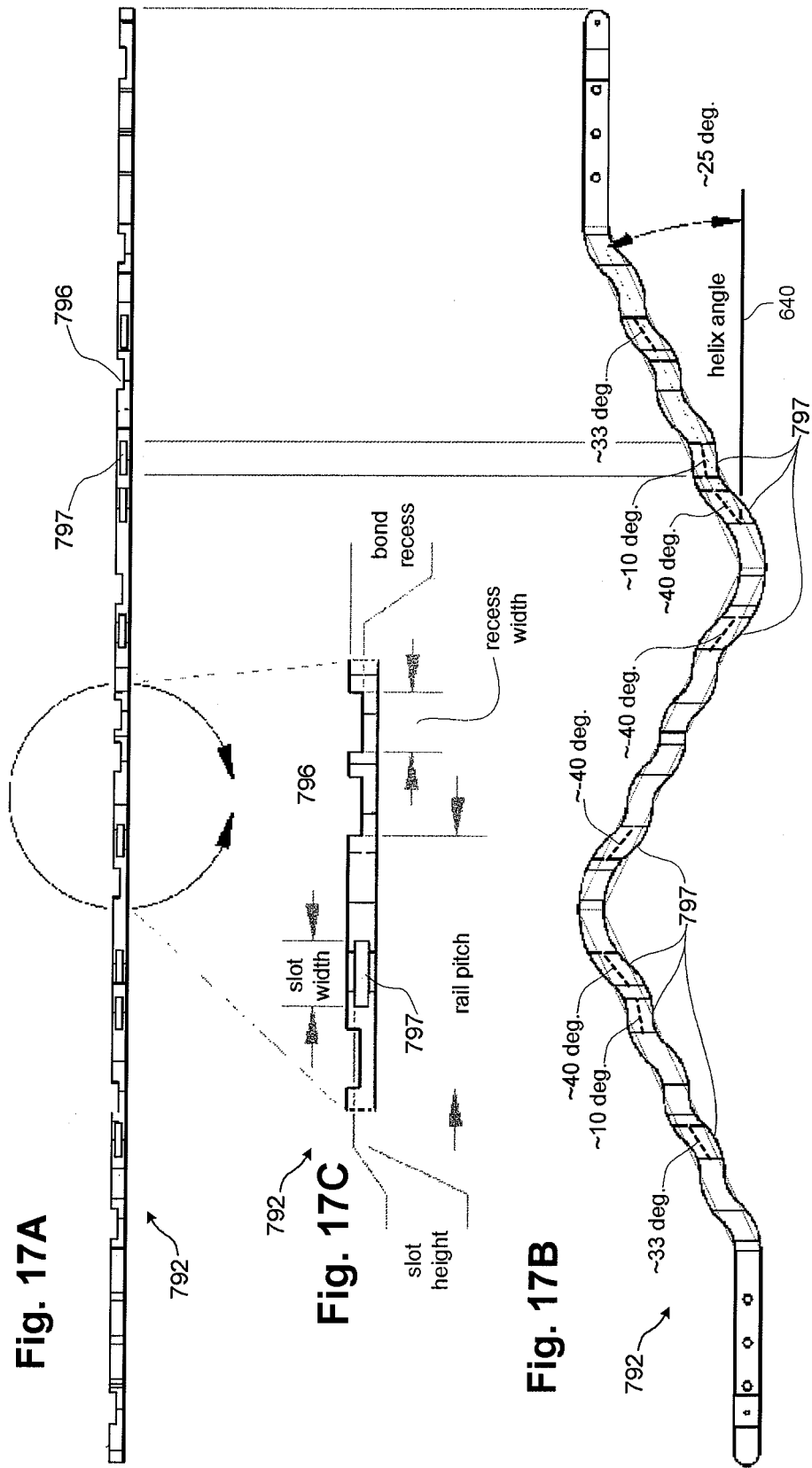

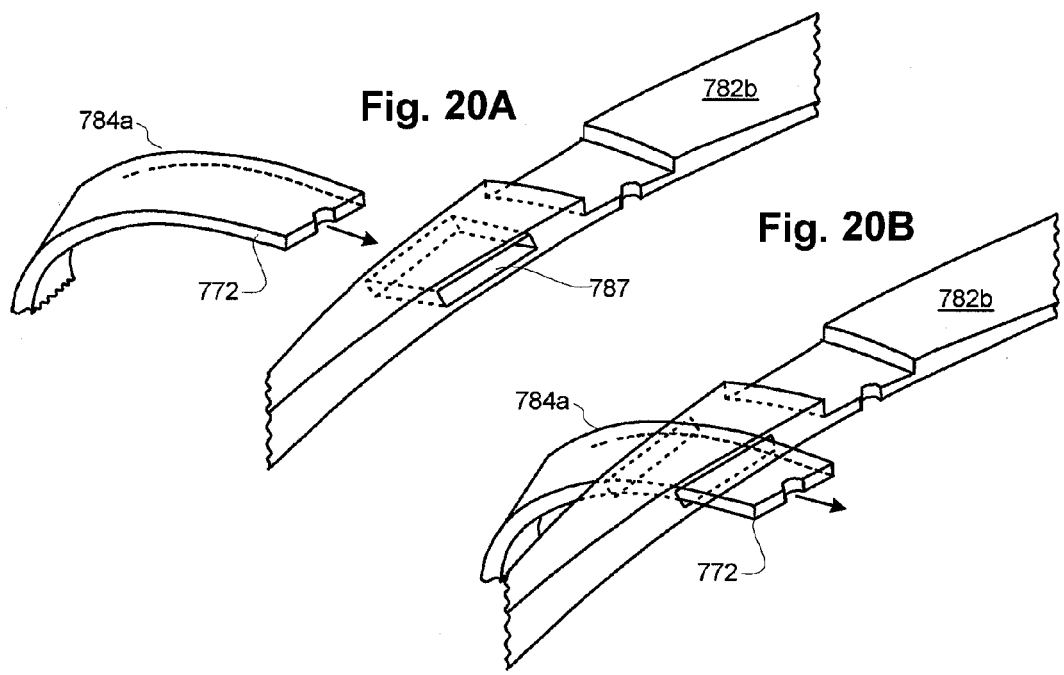
Fig. 20A
Fig. 20B
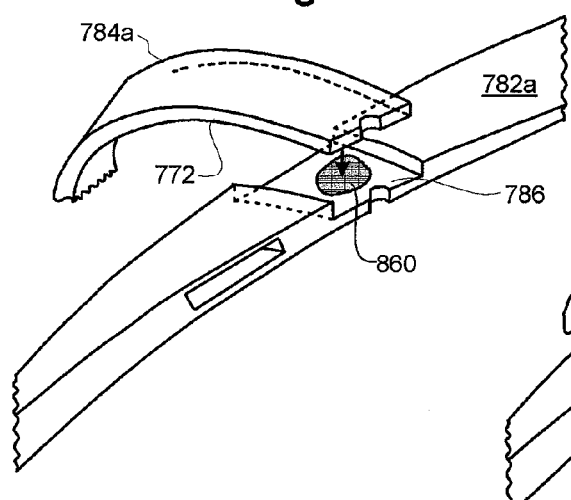
Fig. 20C
Fig. 20D

EXPANDABLE SLIDE AND LOCK STENT

CROSS-REFERENCE TO RELATED APPLICATIONS

This application claims from the benefit of U.S. Provisional Application No. 61/322,843, filed Apr. 10, 2010, titled "EXPANDABLE SLIDE AND LOCK STENT," the entirety of which is incorporated herein by reference.

BACKGROUND

1. Field

The present disclosures relate generally to expandable medical implants for maintaining support of a body lumen, and more specifically, to a uniform stent having improved mechanical and post-deployment dynamic capabilities.

2. Description of the Related Art

Various embodiments of vascular implants; such as stents, thrombus filters, and heart valves, are used in their various embodiments for medical applications. Of these vascular devices, one of the leading candidates as a stent device and structural component is the radially expandable and slidably engaged stent as disclosed in commonly owned U.S. Pat. Nos. 6,033,436; 6,224,626; and 6,623,521; the disclosures of which are hereby incorporated by reference in their entirety. These radially expandable and slidably engaged stents offer the strength of prior expandable stents with the added improvements of low cross-section deliverability, less bulk material thickness, high resolution fitting, and shape customization such as hourglass-shape configurations.

Other radially expandable and slidably engaged stents; such as those disclosed in U.S. Pat. Nos. 5,797,951; 5,549,662; and 5,733,328; further describe the state of the art and their disclosures are hereby incorporated by reference.

Although promising candidates for use as implantable devices and device components, these known radially expandable and slidably engaged stents have mechanical and vasodynamic limitations of which the inventors of the present application set out to address. These limitations can be characterized as deployment related limitations, and limitations related to vasodynamic capabilities.

Deployment related limitations of prior art stents are herein described. Intravascular space; especially that of a patient in need of a vascular implant, is generally inconsistent and varies upon the individual with respect to curvature, plaque buildup and other luminary obstructions. Furthermore, the shape and structure of the stent may impact the rate and order that discrete areas of the stent deploy, e.g., expand. For instance, one portion of the stent may expand prior to a second portion of the stent. Such inconsistent and/or non-uniform deployment may render deployment and placement of prior art stents more difficult and less predictable.

Procedures are available to physicians such as balloon angioplasty, which aid in the reduction of plaque prior to stenting. However, even after such procedures, vascular characteristics remain patient delineated and largely inconsistent. Inconsistencies in vascular characteristics; such as the interference due to a luminary occlusion, require flexibility, distribution of material strength, and vascular adaptability of devices to be implanted.

SUMMARY

In accordance with at least one of the embodiments disclosed herein is a realization that the configuration of a vascular implant, such as a stent, affects the deployment characteristics of the implant. For example, the shape and structure of the stent may impact the rate and order that discrete areas of the stent deploy, e.g., expand. For instance, based at least in part on the characteristics of the stent, one portion of the stent may expand prior to a second portion of the stent. In some embodiments, the stent can be designed with characteristics such that the stent advantageously deploys substantially equally along a longitudinal length of the stent. Accordingly, various embodiments disclosed herein provide a stent that can be deployed or expanded in a generally uniform manner without binding.

Further, in accordance with at least some embodiments disclosed herein is the realization that a helical stent can often experience binding or deployment problems as the helical arrangement unwinds, which must occur from either or both ends of the helical stent. As a result, expansion in the center of the helical stent delayed until the helix is "unwound" from its ends. These expansion characteristics are unsatisfactory as they provide nonuniform deployment and structural properties. Accordingly, in order to address these deficiencies, the inventors of the present application have developed various embodiments of a reversing helical stent having a reversing helical backbone that advantageously provides vastly improved deployment and structural characteristics. Further details such embodiments are provided herein, and can incorporate various features, structures, material configurations, and other attributes such as those disclosed in the copending U.S. patent application Ser. No. 12/577,018, filed Oct. 9, 2009, titled "EXPANDABLE SLIDE AND LOCK STENT," the entirety of which is incorporated herein by reference.

Further, in accordance with some embodiments is the realization that the shape and structure of a stent can impact whether the stent undergoes a twisting or rotation about a longitudinal axis of the stent during deployment. In certain instances, it can be advantageous to reduce or minimize the twisting of a stent during expansion, e.g., to facilitate expansion of the stent by reducing friction between components of the stent and/or between the stent and the vasculature. For example, the stent can include a longitudinally-extending structure (e.g., a backbone or backbone member) that can extend at least partially (e.g. helically) around a circumference of the stent. In some cases, such a configuration can promote deployment, provide torsional flexibility, and reduce twisting of the stent. As disclosed herein, embodiments are disclosed herein that enable such a configuration to not only provide portable flexibility, but to also provide reduced binding of the stent during deployment.

In accordance with some embodiments, the stent can comprise at least one backbone coupled with at least one rail member. The backbone can generally extend along a longitudinal axis of the stent. The rail member can generally extend in a circumferential direction of the stent. Thus, the rail member can define a portion of a circumference of the tubular member. Generally, the rail member can be configured to permit one-way sliding movement of the backbone relative to the rail member so as to permit expansion of the tubular member from the collapsed state to the expanded state.

The backbone can extend helically about the tubular member. In some embodiments, the backbone can comprise a reversing helical shape or configuration. A "reversing helical" shape can be defined as one that changes its circumferential direction as it extends in an axial direction. In some embodiments, a path of a reversing helical backbone can extend helically about the tubular member in a first axial direction and a first circumferential direction and change its path to a second circumferential direction. For example, changing course from the first to the second circumferential direction can include changing from a clockwise circumstantial direction to a counterclockwise circumferential direction. However, these are compression direction can also be varied in only the counterclockwise or clockwise circumferential directions.

In some embodiments, the reversing helical backbone can define one or more elbows or points where the direction or path of the backbone changes. Further, the shape of the backbone can also define at least one peak or high point and at least one trough or low point. For example, when seen from a side view, the backbone can extend in a generally upward direction having an overall positive slope until reaching a peak or uppermost point. Likewise, the backbone can extend from the peak in a generally downward direction having an overall negative slope until reaching a trough or lowermost point. In some embodiments, the shape of the backbone can comprise a plurality of peaks and troughs. Thus, the reversing helical shape can be characterized as comprising an undulating shape, a zig-zag shape, a wave pattern, a sinusoidal shape, and/or the like. Surprisingly, such a configuration can promote deployment of the stent. Additionally, such a configuration can allow for stent characteristics to be modified and/or selected for the requirements of a particular application, e.g., rate of expansion of the stent, force to expand the stent, etc.

Additionally, in some embodiments, at least some of the peaks and/or valleys of the backbone of the stent can be pointed or sharply angled, e.g. a sawtooth, triangle, or the like. In some embodiments, at least some of the peaks and/or valleys of the backbone of the stent can be curved, smoothed, rounded, chamfered, filleted, or the like. Further, in some embodiments, some of the peaks and valleys of the backbone can be pointed while others are rounded. In some embodiments, a generally rounded or smooth curve at a peak or valley can promote an overall rounded shape of the stent. Further, a generally pointed peak or valley may promote a desired strength, flexibility or rigidity characteristic. Thus, some embodiments of the stent can be configured to create localized stiffness, strength, flexibility, patency, roundness, and/or other characteristics by manipulating the shape of peaks and valleys and the angular direction of the backbone, as discussed further herein. For example, a rounded peak may reduce the tendency for the peak to protrude into the lumen of the stent. Thus such a feature can assist in maintaining the patency of the lumen.

In accordance with some embodiments, the reversing helical backbone can be curvilinear (e.g. having a reversing curvilinear shape). For example, the reversing helical backbone can comprise one or more continuous curves, one or more smooth curves, a continuously variable curvature, and/or the like. In some instances, the reversing helical backbone can be formed in an undulating reversing helical configuration. For example, the reversing helical configuration can extend generally in a wave pattern, a sawtooth pattern, a triangular pattern, a rectangular pattern, a zig-zag pattern, and/or the like. Further, the backbone can extend in a regular, repeating, and/or symmetrical pattern. However, in other embodiments of the stent, the backbone can extend in an irregular, non-repeating, and/or asymmetrical pattern.

Accordingly, the reversing helical configuration of the backbone can comprise nearly any wave form. For example, the reversing helical configuration can have a substantially constant amplitude. The amplitude is the distance between the adjacent peak and valley, as measured perpendicular to a longitudinal axis of the backbone. In other embodiments, the reversing helical configuration can have a substantially non-constant, varying, or changing amplitude.

Furthermore, in some embodiments, the reversing helical configuration can have a substantially constant period. The period is the distance or interval between adjacent peaks or adjacent valleys, as measured parallel to the longitudinal axis of the backbone. In other embodiments, the reversing helical configuration of the backbone can have a substantially non-constant, varying, or changing period. In some cases, the period can include one peak and one valley. In some embodiments, the period can include two peaks and one valley. In some embodiments, the period includes two valleys and one peak. In some cases, the period may span the entire length of the stent.

In accordance with at least some embodiments disclosed herein is the realization that the angular direction of the longitudinally-extending backbone structure can affect the characteristics of the stent. For example, a shallower angle (in relation to the longitudinal axis of the stent) can ease deployment of the stent. Conversely, a steeper angle (in relation to the longitudinal axis of the stent) can provide enhanced longitudinal flexibility of the stent and/or radial strength of the stent. As discussed further herein, surprising and advantageous results regarding the flexibility and deployment characteristics of a stent have been achieved by the inventors of the present application through implementing stent configurations disclosed herein. In particular, outstanding results have been obtained through implementing stent configurations having a reversing helical backbone with smooth or curvilinear peaks and valleys and a series of short-phase angle deviations along the length of the backbone between consecutive peaks and valleys.

Furthermore, in some embodiments, the reversing helical configuration can be defined as comprising a plurality of short-phase or leg elements. For example, in a backbone having a sinusoidal reversing helical configuration, each portion of the sinusoid from a valley toward a peak can be a short-phase or leg element, and each portion of the sinusoid from a peak toward a valley can be a short-phase or leg element. Generally, adjacent leg elements can have opposite slopes, e.g., a leg element with a positive slope will normally follow a leg element with a negative slope, and vice-versa.

In some embodiments, one or more of the short-phase or leg elements can be generally straight, generally curvilinear, or define a sub-pattern or variable shape configuration. For example, in some embodiments one or more of the leg elements can itself comprise a wave pattern, a sawtooth pattern, a triangular pattern, a rectangular pattern, a zig-zag pattern, and/or the like. Thus, in some cases, the backbone can have a reversing helical configuration and one or more of the leg elements can have a pattern that deviates from a generally straight length. In particular, some embodiments of the stent can provide a sinusoidal reversing helical backbone having a wave sub-pattern that extends between the peaks and troughs of the sinusoidal reversing helical backbone.

In some embodiments, the amplitude of the sub-pattern or variable shape of the leg elements is less than the amplitude of the reversing helical backbone. Surprisingly, the use of a sub-pattern on a reversing helical backbone has been found to advantageously promote uniform deployment of the stent. For example, it has been found that such a pattern-on-pattern configuration can reduce twisting and/or promote deployment of the stent. Furthermore, such a configuration can also exhibit the advantage of allowing stent characteristics to be modified and/or selected for the requirements of a particular application, e.g., rate of expansion of the stent, force to expand the stent, etc. For example, localized characteristics of the stent can be designed for given results, which provides substantial advantages and customization ability for the stents.

Furthermore, the inventors have also determined that embodiments of the reversing helical stents disclosed herein can also advantageously permit the implementation of longer stents that were not possible with certain prior art stents. Such prior art stents exhibited a "critical length" because their length was limited due to the expansion force requirements of the stent and the expansion force limitations of the catheter balloon. Above a certain size, some balloons were not strong enough to properly deploy such stents. In particular, a helical stent might create undue stress on the balloon toward the center of the stent due to the binding problems discussed above. However, embodiments of the reversing helical stent discussed herein can equalize the expansive force required to deploy the stent and avoid localized binding (and the additional force needed thereat) to expand the stent. Thus, embodiments of the reversing helical stent disclosed herein do not have the same critical length limitations as other helical stents.

Although many of the structural features discussed herein may be shown and described with reference to the circumferential orientation of the stent, some of the features and advantages provided by the reversing helical configuration can be implemented in the width dimension of the stent (e.g., along the radial direction of the stent). In some cases, the reversing helical configuration can be present in the thickness dimension of the backbone (e.g., in a radial dimension of the stent). Some embodiments can have a reversing helical configuration in the width and thickness dimensions of the backbone.

It is also contemplated that embodiments disclosed herein can reduce or minimize the twisting of a stent during expansion. Reducing or minimizing twisting can, for example, reduce friction between components of the stent and/or between the stent and the vasculature. In some instances, a reversing helical configuration can reduce binding of the stent during deployment by, for example, decreasing the relative motion of different components of the stent during expansion. For example, the reversing helical configuration can reduce the rotation of one end of the stent during expansion, from the vantage of a second end of the stent.

A further realization in accordance with at least one of the embodiments disclosed herein is that the configuration of the stent can impact the deployed shape of the stent. In some embodiments it may be desirable for the deployed stent to be substantially round, e.g., circular in cross-section. A substantially round stent can facilitate, for example, improvement of stent strength and placement of the stent in the vasculature. In at least one of the embodiments disclosed herein, a stent can include features to facilitate a substantially round shape in the deployed state. The stent can include one or more components, such as a longitudinally-extending structure (e.g., a backbone), that promotes the roundness of the stent. For example, the backbone can be shaped substantially as a sinusoid. In particular, at least one peak of the sinusoidal backbone is curved, e.g., not formed as a pointed peak or having a sharp angle. Such a rounded peak can promote an overall rounded shape or roundness of the stent. For example, the rounded peak can reduce the tendency for the peak to protrude into the lumen of the stent.

In some embodiments, surprising results have been found in further promoting roundness by implementing configurations in which the rail members are selectively oriented in opposing circumferential directions. For example, some embodiments, a first rail member can extend circumferentially in a first direction and a second rail member can extend circumferentially in a second direction. In some arrangements, the direction in which the first and second rail members extend can be related to or dependent upon the angle between the rail member and longitudinally-extending structure. For example, in some cases, the first and second rail members extend in a given circumferential direction such that the angle between the rail member and longitudinally-extending backbone or structure is an acute angle. Accordingly, it has been determined that, compared to stents with other features, e.g., non-reversing structures, a reversing helical backbone can promote roundness of the stent.

In some embodiments, the backbone can comprise one or more engagement elements. The engagement element can comprise a slot, indentation, passageway, aperture, protrusion, and/or other such structures. In many embodiments illustrated herein, the engagement element comprises a slot that can be configured to receive corresponding rail members, which extend along the circumferential axis of the stent. In some cases, the slots and/or rail members have a locking mechanism configured to permit only one-way sliding movement of the rail members with respect to the slots. In some cases, the locking mechanism can comprise one or more teeth, ridges, paddles, detents, ratchets, ramps, hooks, stops, and/or the like.

In some embodiments, the slots can be angled with respect to the longitudinal axis of the stent, which can advantageously effect the characteristics of the stent. For example, a shallower angle (in relation to the longitudinal axis of the stent) can decrease the force required to expand the stent, and thus can ease deployment of the stent. A steeper angle (in relation to the longitudinal axis of the stent) can increase the longitudinal flexibility of the stent and/or radial strength of the stent, and thus provide a stronger yet more flexible stent.

In some cases, the slot angle can be determined at least in part by the position of the slot along the aforementioned reversing helical configurations of the backbone and/or the leg element. For example, positioning the slot on a more steeply angled portion of reversing helical configurations can generally produce a steeper slot angle. Conversely, positioning the slot on a more shallowly angled portion of reversing helical configurations can generally produce a shallower slot angle.

The slot can be disposed at an angle that is different from the angle of the leg element overall (relative to the longitudinal axis of the stent). For example, in some cases a leg element is angled at about 10° to about 45° from the longitudinal axis of the stent, and the slot is angled at about 5° to about 60° from the longitudinal axis of the stent. In some embodiments, the absolute value of the slot angle can be between at least about 0 degrees and/or less than or equal to about 60 degrees. The absolute value of the slot angle can also be between at least about 10 degrees and/or less than or equal to about 50 degrees. Further, the absolute value of the slot angle can be between at least about 20 degrees and/or less than or equal to about 40 degrees. The slot angle can also vary between at least about 30 degrees and/or less than or equal to about 35 degrees. Finally, as illustrated, the absolute value of the slot angle can be approximately 10 degrees, 33 degrees, 40 degrees. Further, it is contemplated that the slot angle can be any variety or combination of desired angles that are configured to facilitate ease of expansion on the one hand and stent flexibility on the other hand.

In embodiments with multiple slots, each slot can be disposed at an angle that is different than the angle of adjacent slots. For example, in an embodiment with three slots, the first slot can be angled at a first angle, the second slot can be angled at a second angle, and the third slot can be angled at a third angle, wherein the first, second, and third angles are not equal.

Generally, each slot angle can be selected. Advantageously, in light of the above-discussed realization that different angles of the stent components can impact stent characteristics, employing slot angles that are selectable allows the stent to be customized for specific applications. For example, in applications in which radial strength and/or longitudinal flexibility are desired, the steeper slot angles can be employed; in applications in which ease of expansion is desired, shallower slot angles can be employed. Beneficially, it has been found that a stent having a combination of steep and shallow slot angles can provide a balance of radial strength, longitudinal flexibility, and ease of expansion.

As discussed above, the tubular member can include one or more rail members that are slidably coupled to a backbone and define a portion of the circumference of the tubular member. The term "rail member" can refer to on or more elongate, circumferentially extending rails that interconnect with at least one backbone the stent. The rail members in some embodiments can be coupled to or formed with an adjacent rail member to form a radial element. For example, the radial element can be generally U-shaped with a pair of rail members extending therefrom. Some embodiments can include a plurality of adjacent rail members or radial elements that interconnect with one or more respective backbones. Further, groups of rail members and/or radial elements can be circumferentially associated to form a circumferential band or radial module. In some arrangements, each radial element within a radial module can be coupled to a different backbone. For example, in an embodiment with a radial module having first and second radial elements, the first radial element can be coupled to a first backbone and the second radial element can be coupled to a second backbone.

In some arrangements, each radial element within a radial module can be slidingly engaged with an engagement element of a different backbone. In some embodiments, the engagement element can comprise a slot, a passage, a channel, and/or aperture extending through or along a backbone. For example, in an embodiment with a radial module having first and second radial elements, the first radial element can be slidingly received in an engagement element in a second backbone and a second radial element can be slidingly received in an engagement element in a first backbone. Of course, other numbers and combinations of radial elements and backbones are contemplated, e.g., one, three, four, etc. As previously discussed, the radial element and/or the slot can be configured to provide one-way sliding movement of the radial element with respect to the engagement element.

A further realization in accordance with at least one of the embodiments disclosed herein is that a modular stent can advantageously permit a given stent design provide multiple stent lengths. In such a design, the overall length of the stent can be increased or decreased by adding or subtracting modules. As similarly noted above, the modules can provide a circumferential and corresponding axial length to the stent. Further, the axial length of a module can correspond to the periodicity of the backbone, whether having a reversing helical or regular helical configuration. Thus, modular construction can refer to the use of one or more modules or sections that may be used to build the entire length of the stent. Modular construction generally also allows for addition and subtraction of the modules or sections in order to reach a desired size. Further, longitudinal modules or sections, including a backbone and corresponding rail members or radial elements, can also added or removed to a stent construction in order to modify the maximum and minimum diameters of the stent.

Thus, a stent with a modular construction can advantageously be modified (by adding or subtracting longitudinal or circumferential sections or modules) to provide, for example, a desired expanded diameter or length. For example, additional backbones can be added to the stent to provide an increased expanded diameter. Further, additional radial modules or sections can be added to provide a longer stent (which would require increasing the length of the backbone and providing additional rail members or radial elements corresponding thereto).

In some embodiments, an expandable slide and lock stent is provided in which the stent comprises a tubular member having a circumference and a longitudinal axis. The stent can comprise a first backbone and a second backbone and at least one rail member. The first and the second backbones can each have a reversing helical shape. The first and second backbones can extend along at least a portion of the circumference and along the longitudinal axis. In some embodiments, the first and second backbones can be reversing helical backbones defining a generally curvilinear sub-form extending along the backbones between a peak and a valley of the reversing helical backbones.

In some embodiments, at least one of the first and second backbones can define one or more discrete segments. The discrete segments can comprise that portion of the backbone extending between engagement elements of the backbone. Further, the discrete segments can also comprise the portion of the backbone at which the engagement elements are positioned. Furthermore, a backbone can be divided into two or more, and in some embodiments, four or more discrete segments. The number of discrete segments can be even or odd, as long as the overall path of the backbone achieves a desired angular orientation, flexibility profile, and strength characteristics.

The discrete segments can define a discrete helix angle. The discrete helix angle can be a general measurement of the angular direction of the discrete segment relative to the longitudinal axis of the stent. In some embodiments, one or more of the discrete segments of the backbone can define a discrete helix angle that is the same as or different from the discrete helix angle of another discrete segment. Further, in some embodiments, the discrete helix angle can be referred to as a slot angle measured at an engagement element or slot of the backbone.

Furthermore, some embodiments can be configured such that one or more of the discrete segments are generally curvilinear. The curvilinear shape can have increasingly positive slope, a decreasingly positive slope, increasingly negative slope, or a decreasingly negative slope. Thus, in contrast to straight or pointed portions of a backbone, the curvilinear discrete segments can provide improved flexibility, bending strength, and roundness of the stent.

The rail member can define proximal and distal ends. The proximal end of the rail member can be coupled to the first backbone. The distal end of the rail member can extend from the first backbone in the circumferential direction. The rail member can be configured to engage with an engagement element in the second backbone. Further, the rail member can be configured to provide one-way movement of the second backbone away from the first backbone such that the tubular member can be expanded between a collapsed diameter and an expanded diameter.

The reversing helical shape of the backbones can comprise a reversing undulating shape. The reversing helical shape can comprise a portion having a positively trending slope and a portion having a negatively trending slope. At least one of the portions having a positively trending slope and the portion having a negatively trending slope can further comprise a plurality of wave forms. The plurality of wave forms can comprise a plurality of continuous curves. Further, the intersection of the rail member and the second backbone can be at an oblique angle.

The stent can further comprising a plurality of rail members defining proximal and distal ends. The proximal end of each of the rail members can be coupled to the first backbone. The distal end of each of the rail members can extend from the first backbone in the circumferential direction and can be configured to intersect and pass through one of a plurality of slots in the second backbone.

Further, one or more of the slots in the backbone can define a slot angle that extends skew relative to the longitudinal axis of the stent. For example, these slot angles of the slots in the backbone can be different from each other, as discussed further herein. For example, in some embodiments, each of the slot angles can be disposed at a different angle with respect to the longitudinal axis compared to adjacent slot angles. Further, the slot angles can also be generally equal to each other.

In some embodiments, the rail member can comprise one or more teeth for engaging the slot to provide one-way expansion of the stent. Accordingly, and some embodiments, the slot can comprise a central passage and at least one internal recess for engaging the teeth of the rail member.

In accordance with another embodiment, methods for forming the stands and stent components are provided. For example, any of the embodiments disclosed herein can be formed by initially forming the structures disclosed, such as the reversing helical backbone, the discrete segments (depending on their configuration), and the like. For example, a method for forming a stent can be provided which comprises: forming a central passage as a first through hole in the backbone in a circumferential direction of stent, and forming the at least one internal recess as a second through hole in the backbone in a direction transverse to a circumferential direction of the central passage such that the first and second through holes partially overlap.

Next, in accordance with some embodiments, an expandable stent is provided that can comprise a plurality of radial components interconnected to form a tubular member. The stent can comprise at least one reversing helical backbone having a plurality of slots and further comprising a plurality of rail members. The reversing helical backbone can define a generally curvilinear sub-form extending along the backbone between a peak and a valley of the reversing helical backbone. Further, the rail members can be received into the slots of the helical support member to facilitate one-way expansion of the stent. The expandable stent can be made from a bioresorbable polymer. Further, these stent can be configured to exhibit structural properties equivalent to a metal stent.

Furthermore, a radial structure, module or element for forming an expandable slide and lock polymer stent can be provided which comprises an undulating helical backbone and a plurality of the elongate ribbed elements. The undulating helical backbone can half a plurality of engagement slots and a plurality of connection slots. The at least one engagement slot can be spaced between consecutive connection slots along the backbone. The plurality of elongate rib elements can have proximal and distal portions. The proximal portion can be interconnectable with one or more connections slots of the continuously slotted backbone. Each rib element can be positionable generally circumferentially about the longitudinal axis and have a fixed engagement at a nonperpendicular angle with respect to the helical backbone.

The plurality of elongate rib elements can be arranged to interconnect with at least one other undulating helical backbone of another radial element so as to form an expandable tubular skeleton. The elongate rib elements can have a one-way slidable engagement with the engagement slots of the helical backbone of the other radial element. The tubular skeleton can be configured to expand radially between a collapsed diameter and an expanded diameter upon circumferential motion of the slidable engagement of the rib elements to the helical backbones. Further, the slidable engagement can include a mechanism restraining collapse of the tubular skeleton from the expanded diameter towards the collapsed diameter.

In some embodiments, the undulating helical backbone can comprise portions of reduced thickness for allowing at least partial nesting of an elongate rib element thereagainst. Further, a pair of elongate rib elements can be interconnected at their distal portions by a crossbar. The crossbar can comprise an offset portion configured to at least partially receive an elongate rib of an adjacent radial element for reducing a passing profile of a stent formed using a plurality of radial elements. Next, the undulating helical backbone can extend helically at a generally fixed radius and helix angle relative to the longitudinal axis. The engagement slot can comprise a through slot that defines a central axis extending in a generally circumferential direction and within a plane that is perpendicular to the longitudinal axis of the radial element, the central axis of the engagement slot can extend at a nonperpendicular angle relative to the helical backbone.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments. The drawings contain the following figures:

FIG. 3 shows an assembly in which rail members of the radial elements are generally obliquely oriented with respect to the stent longitudinal axis, and perpendicular to the backbones, according to an embodiment.

FIG. 5 shows a stent assembly with multiple locally non-slanted backbone portions, according to an embodiment.

FIGS. 9A-9D illustrate an embodiment with multi-directional rail member arrays, in expanded and collapsed configurations.

FIGS. 10A-10F illustrate alternative embodiments in which the teeth or locking members are provided with one or more relieving holes or indentions located within the rail member, according to an embodiment.

FIGS. 11A-11D illustrate the engagement of teeth or locking members on the rail members of the radial element, according to an embodiment.

FIG. 12A illustrates a stent embodiment having rail modules with rail members, in the compacted state, according to an embodiment.

FIG. 17A illustrates a plan view of an embodiment of a backbone of the stent embodiment of FIG. 12A, according to an embodiment.

FIG. 17B illustrates an elevation view of an embodiment of a backbone of the stent embodiment of FIG. 12A, according to an embodiment.

FIG. 17C illustrates a focused view of a portion of the stent embodiment of FIG. 17A, according to an embodiment.

FIGS. 20A-20D illustrate an assembly process of mounting embodiments of rail members to an embodiments of backbone, according to an embodiment.

DETAILED DESCRIPTION

Figure 1:
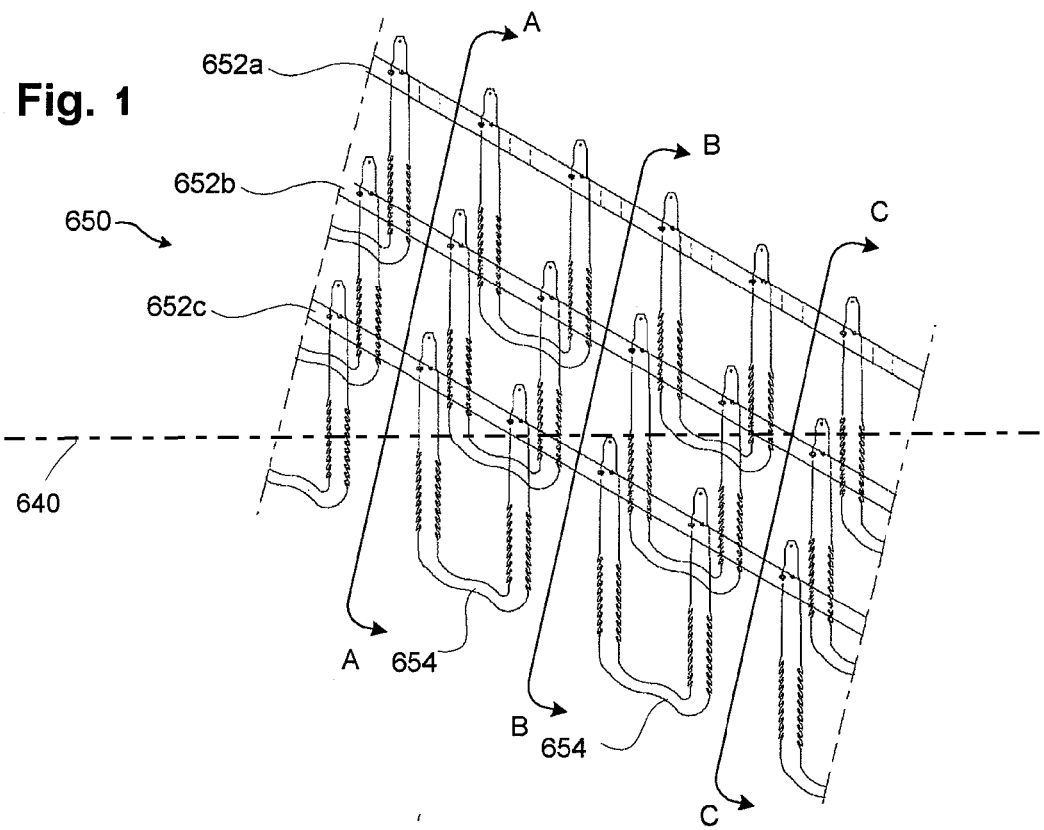
FIGS. 1 and 2 show planar representations of two embodiments of a stent or stent assembly, illustrating different interconnecting arrangements of the backbones and radial elements.

As will be discussed herein, embodiments of the stent summarized above and defined by the enumerated claims may be better understood by referring to the following detailed description, which should be read in conjunction with the accompanying drawings. This detailed description of embodiments, set out below to enable one having skill in the art to build and use one particular implementation, is not intended to limit the enumerated claims, but to serve as a particular example thereof. While the description sets forth various embodiments in specific detail, it will be appreciated that the description is illustrative only and should not be construed in any way as limiting the same. Furthermore, various applications of the embodiments, and modifications thereto, which can occur to those who are skilled in the art, are also encompassed by the general concepts described herein.

Overview

As discussed herein, in accordance with at least one of the embodiments disclosed herein is the realization that a vascular implant may experience a number of mechanical limitations related to delivery. For example, some portions of the vasculature are curved or substantially non-cylindrical. These portions of the vasculature have proven difficult to deploy stent devices. Sometimes, the curvature of the vessel can cause a deployed stent to fold, especially in stents with insufficient flexibility in the design. Curved vessels further increase the potential for hinging and denting as described in further detail below.

A vascular implant may also experience a number of countering forces post-deployment. Some of these countering forces are a result of what is herein referred to as vasodynamics; the resulting movements, constrictions and contortions of the vasculature. Of these countering forces is crush force, caused by post-expansion elastic recoil of the vessel.

Additionally, some stents experience an occlusion-derived impaction force; a point force derived from the impact of a luminary occlusion directly onto the device; such a luminary occlusion can be plaque or a thrombus. Other countering forces such as dilation, and contortion, are to be discussed in further detail below.

In accordance with an aspect of at least some embodiments is the realization that known radially expandable and slidably engaged stents can experience what the inventors of this application refer to herein as "hinging." Many slidably-engaged expandable stents possess a common limitation where the engagements are generally longitudinally aligned, thereby inherently creating an alignment of failure points. A failure point is a weakness in a stent design, usually a point where two parts are joined together in a less than permanent fashion such as an engagement between slidably-engaged rail members and/or radial modules. When an amount of radial pressure is exerted on the expanded stent, the stent tends to buckle or fold at the failure point. A series of failure points that are longitudinally aligned can act as a perforation in the material and cause a substantial weakness and propensity for hinging.

Another plaque-related problem is herein referred to as "denting." Denting is caused by an inherent device pattern weakness where a vaso-occlusion can drive a portion of at least one stent module into the luminary space, thereby substantially enhancing the effect of the vaso-occlusion. Such an occlusion or dent can lead to collection of thrombus or flow distortions which are problematic and can increase stenosis.

Vascular plaque is typically non-uniform and often forms in a bulky occlusion, such an occlusion can place added stress on the stent via a point force, and increase the risk of hinging or denting.

The inventors of the present application have recognized that denting can significantly dampen or interfere with vasodynamics, and therefore may cause an increase in realized stenosis. Furthermore, denting may not be immediately apparent to the implanting physician where a polymer stent is adapted for increased ductility over time.

In accordance with at least one of the embodiments disclosed herein is a realization that the configuration of a vascular implant, such as a stent, may effect the deployment characteristics of the implant. For example, the shape and structure of the stent may impact the rate and order that discrete areas of the stent deploy, e.g., expand. For instance, based at least in part on the characteristics of the stent, one portion of the stent may expand prior to a second portion of the stent. In some embodiments, the stent can be designed with characteristics such that the stent advantageously deploys substantially equally along a longitudinal length of the stent. Accordingly, various embodiments disclosed herein provide a stent that can be deployed or expanded in a generally uniform manner without binding.

In accordance with some embodiments disclosed herein, the stent can be slidably expandable. The geometry of the stent may be generally described as a tubular member. The tubular member can have a collapsed state and an expanded state.

Many devices are fabricated from a biodegradable polymer which may become substantially more ductile and flexible with the progression of time up to a point of water absorption equilibrium. As water is absorbed, the polymer material becomes bendable or ductile. Differing polymer compositions will have a varied rate of moisture absorption. The inventors of the present application recognized the benefits of controlled water absorption into the polymer material such as a reduced propensity for microfissures. Furthermore, the inventors of the present application recognized detriments such as a propensity for denting where the design pattern provides unsupported adjacent components. The likelihood of denting occurrences is increased for stent patterns lacking the support of a structural backbone, especially when there are unsecured corners or other points having a propensity for weakness. Often, the extent to which denting occurs cannot be determined until several hours after the deployment procedure, hence the importance to minimize the potential for denting and improving the design pattern of the target device.

In accordance with at least one of the embodiments disclosed herein, the inventors of the present application have recognized that a mechanically-improved stent design will overcome one or more of the limitations set out above, and will further set out to increase adaptability to the dynamics of the vasculature.

Many prior art stent embodiments are designed around crush force and maintaining patency of a luminary space. Although patency of the lumen is of primary concern, there are other factors which must be addressed in an effort to go beyond functionality, but rather to move toward the successful treatment and healing of a vessel.

The vasculature is a dynamic system. Although it is difficult to quantify, the vasculature may experience a number of dynamic movements at any given moment in time. Of these is a wave-like dilation, which presents variability in the interior diameter of the vessel at a given location. Dilation can occur from a change in blood pressure or other change in the circulation. Additionally, portions of the vasculature can experience a contortion or twist like motion in addition to dilation. Where there is plaque or a luminary occlusion, the vasculature can experience a resistance to these natural movements. Such a resistance can cause the adjacent tissue to undergo a cytotic response, such as the division of cells, or intravascular cell growth known as neointimal growth. Neointimal growth is a new or thickened layer of arterial intima formed especially on a prosthesis or in atherosclerosis by migration and proliferation of cells.

Clinical data generally shows that stent implants stimulate neointimal growth in the vessel immediately subsequent to implantation. Neointimal growth is acceptable up to a point where blood pressure is substantially increased or where the lumen is obstructed and blood can no longer efficiently pass.

It is thought that resistance to vasodynamics, among other things, can dramatically increase stenosis surrounding an implanted vascular device. Therefore, it is critical to understand the dynamics of the vasculature and to design a stent capable of maintaining patency of the lumen while promoting the motions associated with vasodynamics such as periodic dilation and contortion. A stent designed to incorporate the dynamics of the vasculature can better serve to treat and ultimately heal the vessel.

Generally, neointimal growth surrounds and encompasses the implanted stent, leaving the stent to reside substantially within the new vessel wall. It is in this state that stent mechanics are critical in minimizing further stenosis.

Although stents can be made of generally any biocompatible material, there is a movement toward the use of stents fabricated from a biodegradable and bioresorbable polymer. Biodegradation is the structural decomposition of a polymer, often occurring as bulk erosion, surface erosion, or a combination thereof. Bioresorption includes the cellular metabolism of the degraded polymer. The inventors of the present application have set out to design a stent capable of utilizing the degradation and resorption properties of the polymer to enhance the healing and treatment of the vessel.

In some embodiments, there is provided a stent having a uniform distribution of failure points. This uniform distribution can minimize, if not eliminate the potential for hinging and denting. Further, in some embodiments, there is provided a stent having a rotationally flexible backbone capable of adaption to vasodynamic movements, thereby minimizing stenosis of the vasculature.

In some embodiments, there is provided a stent design capable of being efficiently encapsulated with neointimal growth, such that initial degradation of the stent material will transform the stent into a rotationally flexible and vaso-adaptive support within the new vessel wall.

In summary, there remains a need for an improved radially expandable and slidably engaged luminary support structure: one that uniformly distributes failure points about the device so as to prevent hinging, one that provides adequate support to components so as to prevent denting, one that embraces the effects of water absorption so as to prevent micro fissures while providing effective stenting to the vasculature, one that is capable of restoring vaso-motion to the treated vessel upon neo-intima containment, and one that embraces known properties of radially expandable and slidably engaged support structures such as low cross-section deliverability, less bulk material thickness, high resolution fitting, and shape customization such as hourglass-shape configurations.

An expandable stent is disclosed in accordance with an embodiment of the present inventions. The stent can provide radial support to maintain patency of a lumen, a flexible vaso-adaptive backbone structure, and a uniform circumferential distribution of slidable engagements.

Aside from radial expansion and an ability to maintain patency of the body lumen, the present disclosure provides solutions to the aforementioned problems of hinging, denting and restriction of vasodynamic movements.

In accordance with at least one of the embodiments disclosed herein is the realization that a propensity for hinging is increased in stent designs having an alignment of engagement means that are substantially parallel with respect to the longitudinal axis of the stent. Further, in accordance with at least one of the embodiments disclosed herein is the realization that a potential for denting can be minimized by incorporating a support backbone to secure the extremities and corners of those members or features associated with maintaining patency of the lumen, herein elongate members.

Additionally, in accordance with at least one of the embodiments disclosed herein is the realization of the importance of providing a stent having flexibility sufficient to promote and adapt to natural vasodynamic movements while maintaining patency of the lumen. Further, stenosis can be minimized by improving the flexibility of the stent so as to provide adaption to vasodynamic movements such as wave-like dilation and contortion movements.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments can be useful in lumens of other body systems such as the reproductive, endocrine, hematopoietic and/or the integumentary, musculoskeletal/orthopedic and nervous systems (including auditory and ophthalmic applications); and, (4) finally, stent embodiments can be useful for expanding an obstructed lumen and for inducing an obstruction (e.g., as in the case of aneurysms).

The term "stent" is further used herein to designate embodiments such as; support structures for maintaining patency of a body lumen; support structures for anchoring thrombus filters and heart valves; as well as support structures for the distribution and delivery of therapeutic agents as well as other devices.

In the following description of embodiments, the term "stent" can be used interchangeably with the term "prosthesis" and should be interpreted broadly to include a wide variety of devices configured for supporting a segment of a body passageway.

Furthermore, it should be understood that the term "body passageway" encompasses any lumen or duct within a body, such as those described herein.

Still further, it should be understood that the term "shape-memory material" is a broad term that can include a variety of known shape memory alloys, such as nickel-titanium alloys, as well as any other materials that return to a previously defined shape after undergoing substantial plastic deformation.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents can be used in applications wherein precise placement and sizing are important. Balloon expandable stents can be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

General Stent Geometry

In accordance with the principles disclosed herein, the geometry of the stent may be generally described as a tubular member. The tubular member can be expanded from a collapsed state to an expanded state.

In accordance with these various features, the slidably engaged expandable stent can include at least one backbone or backbone member coupled with at least one rail member, elongate member or radial element. As discussed herein, a plurality of rail members (also referred to as elongate members or rails), such as two or more, can be coupled together to form a radial element. The backbone and the rail member and/or radial element can define a circumference of the tubular member. Generally, the rail member is configured to permit one-way sliding movement of at least one of the backbones (in relation to the rail member), so as to permit expansion of the tubular member from the collapsed state to the expanded state.

In some embodiments, the stent can comprise one or more reversing helical backbones. Many of the reversing helical backbones of the embodiments described herein provides a high degree of longitudinal structural integrity combined with longitudinal flexibility and radial strength, both in the compacted and deployed configurations. One or more elongate members, elongate rails, or radial elements can extend from the backbone and can interlock with one or more other backbones to form an interwoven circumferential surface that provides crush strength and radial stiffness without unduly inhibiting longitudinal or rotational flexibility. In some embodiments, the generally circumferential alignment of the radial elements allows the elongate members to engage each other and the backbone in a configuration which provides "hoop-strength," thus providing a substantial increase overall longitudinal "beam" stiffness. In some embodiments, the generally circumferential alignment of the radial elements allows the elongate members to engage each other and the backbone without direct coupling in a configuration to provide "hoop-strength" and a substantial increase overall longitudinal "beam" stiffness. In certain embodiments, the stent structure may be described as expandable tubular "skeleton" assembly defined by the systematic movable interconnection of a plurality reversing helical "backbones" via a plurality of circumferentially arranged rail or "rib" elements.

In some embodiments, the backbone comprises one or a plurality of engagement elements. The engagement element can comprise a slot, indentation, passageway, aperture, protrusion, and/or other such structures. In many embodiments illustrated herein, the engagement element comprises at least one slot. In other words, embodiments of the backbone can be configured to comprise one or a series of slots formed along the backbone for facilitating interconnection of the backbone assembly with one or more rail members or radial elements. This may be referred to as a continuously slotted backbone. The slots of the backbone can be advantageous by reducing the tendency for hinging, kinking, and buckling of the stent. Indeed, in some cases, the slots in the backbone can provide for local areas of reduced stiffness and/or enhances flexibility. Further, in conjunction with the unique reversing helical backbone structure and slide-and-lock expansion mechanism of embodiments disclosed herein, the slotted backbone can also contribute to superior flexion and crush strength of the stent.

Generally, the backbone comprises a reversing helical shape, such as a shape that has an alternating positive and negative slope. For example, the reversing helical shape can be a zig-zag, undulation, wave pattern, or the like. In some cases, the reversing helical shape is curvilinear or a series of continuous curves, smooth curves, continuous variable curvature, or the like. In some arrangements, the reversing helical shape is symmetrical along the longitudinal axis of the stent. For example, in some embodiments the backbone comprises a sinusoidal shape.

As discussed above, a "reversing helical" shape can be defined as one that changes its circumferential direction as it extends in an axial direction. In some embodiments, a path of a reversing helical backbone can extend helically about the tubular member in a first axial direction and a first circumferential direction and change its path to a second circumferential direction. For example, changing course from the first to the second circumferential direction can include changing from a clockwise circumstantial direction to a counterclockwise circumferential direction. However, these are compression direction can also be varied in only the counterclockwise or clockwise circumferential directions.

In some embodiments, the reversing helical backbone can define one or more elbows or points where the direction or path of the backbone changes. Further, the shape of the backbone can also define at least one peak or high point and at least one trough or low point. For example, when seen from a side view, the backbone can extend in a generally upward direction having an overall positive slope until reaching a peak or uppermost point. Likewise, the backbone can extend from the peak in a generally downward direction having an overall negative slope until reaching a trough or lowermost point. In some embodiments, the shape of the backbone can comprise a plurality of peaks and troughs. Thus, the reversing helical shape can be characterized as comprising an undulating shape, a zig-zag shape, a wave pattern, a sinusoidal shape, and/or the like. Surprisingly, such a configuration can promote deployment of the stent. Additionally, such a configuration can allow for stent characteristics to be modified and/or selected for the requirements of a particular application, e.g., rate of expansion of the stent, force to expand the stent, etc.

Additionally, in some embodiments, at least some of the peaks and/or valleys of the backbone of the stent can be pointed or sharply angled, e.g. a sawtooth, triangle, or the like. In some embodiments, at least some of the peaks and/or valleys of the backbone of the stent can be curved, smoothed, rounded, chamfered, filleted, or the like. Further, in some embodiments, some of the peaks and valleys of the backbone can be pointed while others are rounded. In some embodiments, a generally rounded or smooth curve at a peak or valley can promote an overall rounded shape of the stent. Further, a generally pointed peak or valley may promote a desired strength, flexibility or rigidity characteristic. Thus, some embodiments of the stent can be configured to create localized stiffness, strength, flexibility, patency, roundness, and/or other characteristics by manipulating the shape of peaks and valleys and the angular direction of the backbone, as discussed further herein. For example, a rounded peak may reduce the tendency for the peak to protrude into the lumen of the stent. Thus such a feature can assist in maintaining the patency of the lumen.

In accordance with some embodiments, the reversing helical backbone can be curvilinear. For example, the reversing helical backbone can comprise one or more continuous curves, one or more smooth curves, a continuously variable curvature, and/or the like. In some instances, the reversing helical backbone can be formed in an undulating reversing helical configuration. For example, the reversing helical configuration can extend generally in a wave pattern, a sawtooth pattern, a triangular pattern, a rectangular pattern, a zig-zag pattern, and/or the like. Further, the backbone can extend in a regular, repeating, and/or symmetrical pattern. However, in other embodiments of the stent, the backbone can extend in an irregular, non-repeating, and/or asymmetrical pattern.

Accordingly, the reversing helical configuration of the backbone can comprise nearly any wave form. For example, the reversing helical configuration can have a substantially constant amplitude. The amplitude is the distance between the adjacent peak and valley, as measured perpendicular to a longitudinal axis of the backbone. In other embodiments, the reversing helical configuration can have a substantially non-constant, varying, or changing amplitude.

Furthermore, in some embodiments, the reversing helical configuration can have a substantially constant period. The period is the distance or interval between adjacent peaks or adjacent valleys, as measured parallel to the longitudinal axis of the backbone. In other embodiments, the reversing helical configuration of the backbone can have a substantially non-constant, varying, or changing period. In some cases, the period can include one peak and one valley. In some embodiments, the period can include two peaks and one valley. In some embodiments, the period includes two valleys and one peak. In some cases, the period may span the entire length of the stent.

In accordance with at least some embodiments disclosed herein is the realization that the angular direction of the longitudinally-extending backbone structure can affect the characteristics of the stent. For example, a shallower angle (in relation to the longitudinal axis of the stent) can ease deployment of the stent. Conversely, a steeper angle (in relation to the longitudinal axis of the stent) can provide enhanced longitudinal flexibility of the stent and/or radial strength of the stent. As discussed further herein, surprising and advantageous results regarding the flexibility and deployment characteristics of a stent have been achieved by the inventors of the present application through implementing stent configurations disclosed herein. In particular, outstanding results have been obtained through implementing stent configurations having a reversing helical backbone with smooth or curvilinear peaks and valleys and a series of short-phase angle deviations along the length of the backbone between consecutive peaks and valleys.

Furthermore, in some embodiments, the reversing helical configuration can be defined as comprising a plurality of short-phase or leg elements. For example, in a backbone having a sinusoidal reversing helical configuration, each portion of the sinusoid from a valley toward a peak can be a short-phase or leg element, and each portion of the sinusoid from a peak toward a valley can be a short-phase or leg element. Generally, adjacent leg elements can have opposite slopes, e.g., a leg element with a positive slope will normally follow a leg element with a negative slope, and vice-versa.

In some embodiments, one or more of the short-phase or leg elements can be generally straight, generally curvilinear, or define a sub-pattern or variable shape configuration. For example, in some embodiments one or more of the leg elements can itself comprise a wave pattern, a sawtooth pattern, a triangular pattern, a rectangular pattern, a zig-zag pattern, and/or the like. Thus, in some cases, the backbone can have a reversing helical configuration and one or more of the leg elements can have a pattern that deviates from a generally straight length. In particular, some embodiments of the stent can provide a sinusoidal reversing helical backbone having a wave sub-pattern that extends between the peaks and troughs of the sinusoidal reversing helical backbone.

In some embodiments, the amplitude of the sub-pattern or variable shape of the leg elements is less than the amplitude of the reversing helical backbone. Surprisingly, the use of a sub-pattern on a reversing helical backbone has been found to advantageously promote uniform deployment of the stent. For example, it has been found that such a pattern-on-pattern configuration can reduce twisting and/or promote deployment of the stent. Furthermore, such a configuration can also exhibit the advantage of allowing stent characteristics to be modified and/or selected for the requirements of a particular application, e.g., rate of expansion of the stent, force to expand the stent, etc. For example, localized characteristics of the stent can be designed for given results, which provides substantial advantages and customization ability for the stents.

Various embodiments described herein can provide for a polymeric stent that exhibits advantageous structural properties that are comparable to those of a metal stent. For example, research has illustrated that the helical backbone construction, paired with the slide-and-lock interconnection of radial elements, can be used in a polymer stent such that the advantages of bioresorbability and superior structural stiffness and strength (similar to that of a metal stent) can be realized. This significant advance in stent technology allows other preferable materials—not just metals—to be used in a stent to achieve desirable material properties, while ensuring that the necessary structural properties of the stent are also achieved.

The slidably engaged radial elements can be configured for unidirectional slidable movement so as to permit the radial expansion of the tubular member. In an embodiment, the stent can define a first collapsed diameter, and a second expanded diameter. The slidably engaged expandable stent is adapted to be expandable between at least the first collapsed diameter and at least the second expanded diameter.

In some embodiments, the slidably engaged expandable stent is configured with two radial modules, each radial module being slidably engaged and configured for unidirectional expansive movement. Each radial module can include a backbone, a first elongate member and a second elongate member. In some embodiments, the elongate members are annular elongate members; in some embodiments, the elongate members are ring-like members elongated from the backbone. The elongate members can be slidably engaged with slots and can be configured for unidirectional slidable movement.

The slidably engaged expandable stent in some embodiments has a plurality of radial elements, including a first radial element and a second radial element. These radial elements can be substantially commonly oriented with respect to the backbone. The second radial element can be axially or circumferentially offset with respect to the first radial element.

The axially or circumferential offsetting of rail members and/or radial elements allows a distribution of slidable engagements. Such a distribution of slidable engagements is said to render the stent uniform with respect to mechanical failure points; as the slidable engagements are generally the weakest mechanical points in the design. Slidable engagements are herein defined as the engagement means between two slidably engaged radial modules. In some embodiments, the slidable engagements are defined by the interlocking of slots and contained rail members of the slidably engaged radial elements.

The slots can further comprise a locking member. A locking member can be, for example, a tooth, a deflectable tooth, stop, ridge, paddle, detent, ratchet, ramp, hook, or the like. In some embodiments, the slots comprise a number of stops inside the surface or cavity of the slot. In another embodiment, the slots comprise at least one tooth adjacent to the entry side of the slot.

The slots can be angled with respect to the longitudinal axis of the stent, which can to provide further advantages to the stent. For example, it has been determined that a shallower angle (in relation to the longitudinal axis of the stent) can decrease the force required to expand the stent, and thus can ease deployment of the stent. A steeper angle (in relation to the longitudinal axis of the stent) can increase the longitudinal flexibility of the stent and/or radial strength of the stent, and thus provide a stronger yet more flexible stent. Thus, appropriate slot angles may be selected to promote desired stent characteristics.

Additionally, the elongate members can be configured to comprise at least one conjugate locking member. A conjugate locking member is essentially a component designed to engage with the locking member. In some embodiments, a conjugate locking member is adapted to fit be engaged by the locking member. In one embodiment, the conjugate locking member is one of a tooth, a deflectable tooth, or a stop. A locking member and a conjugate locking member define an engagement means whereby the radial elements, rail members, and/or radial modules are slidably engaged. Exemplary conjugate locking members are described in co-pending U.S. patent application Ser. No. 12/577,018, filed Oct. 9, 2009, titled "EXPANDABLE SLIDE AND LOCK STENT," the entirety of which is incorporated herein by reference.

The backbone can comprise a flexible link, such as a spring link. Alternatively, the flexible backbone can be made of an elastomeric polymer material sufficient to promote adaption to vasodynamic movements. Elastomeric polymers are defined in the art, however for illustrative purposes examples can include polycaprolactone, polydioxanone, and polyhexamethylcarbonate.

Various embodiments of the stents disclosed herein can incorporate various features, structures, material configurations, and other attributes of Applicant's patents and co-pending patent applications, such as U.S. patent application Ser. Nos. 11/016,269, 11/455,986, 11/196,800, 12/193,673, 11/399,136, 11/627,898, 11/897,235, 11/950,351, 11/580, 645, 11/680,532, and U.S. Pat. No. 6,951,053, each of which are hereby incorporated by reference in their entireties.

EXAMPLES

FIGS. 1-20D illustrate examples of stent embodiments having aspects of the embodiments disclosed herein. For clarity of the stent structure, certain of these figures illustrate various stent embodiments in a flat (e.g., unrolled) state. It should be understood, however, that such for delivery and/or implantation in a vascular structure, such embodiments can be rolled to form a tubular member. Although parts of the stent may have been illustrated as being on opposite sides of the stent (see, e.g., FIG. 9A, elements 732a and 735) for clarity, in the rolled state such elements can be slidingly engaged (see, e.g., FIG. 9C). Various figures include a representation of a longitudinal axis 640 of a stent if formed into a tubular member. The longitudinal axis 640 can provide a frame of reference in measuring relative angles and orientations of components of the stents disclosed herein. However, the longitudinal axis 640 may not in all figures represent a center axis of the stent, but instead represent an axis extending parallel to a center axis of the stent.

Cross-Over Rail Pattern Versus Discrete Rail Modules

Figure 2:
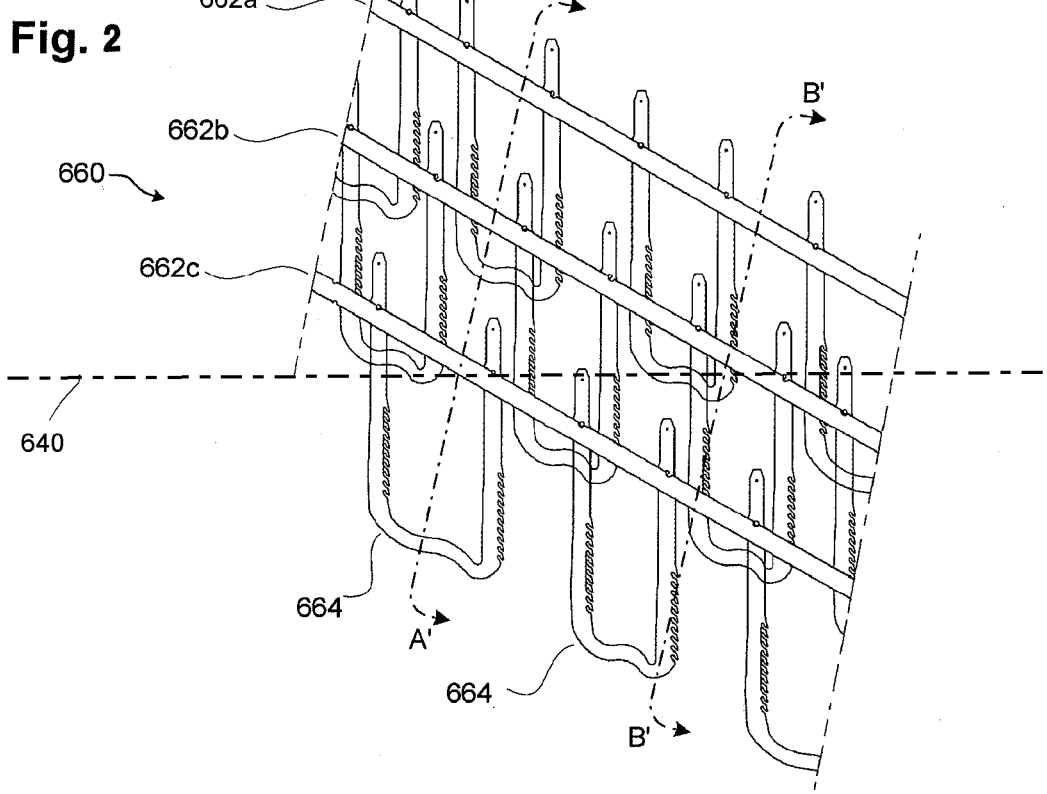

FIGS. 1 and 2 show planar representations of the circumferential surfaces (in the tubular state) of embodiments of a stent or stent assembly. The examples of FIGS. 1 and 2 illustrate two different interconnecting arrangements of the elongate members or rail members of the stents, which extend generally circumferentially so as to integrate the stent assembly. The embodiments illustrated have generally U-shaped rail elements and three backbones. Other embodiments have more or fewer than three backbones. In other embodiments, the rail members need not be U-shaped, e.g., alternative shapes, such as "W-shaped" members and the like, may be advantageously employed).

FIG. 1 shows a stent assembly 650 with 3 backbones 652a-c. The plurality of rail members or rail elements 654 are arranged in triplet patterns bonded to respective adjacent backbones. In this arrangement, cutting lines AA, BB and CC can be seen to cross all three backbones without intersecting any rail member. In this sense, the rail members may be described as being arranged in distinct radial modules. The radial modules may contain more or fewer than three rail members.

Further, in some embodiments, rail members or radial elements of a circumferentially extending radial module can be positioned adjacent to or at least partially overlap with rail members or radial elements of another circumferentially extending radial module. The spacing or overlap of adjacent radial modules can promote stiffness and flexibility of the stent.

For example, in the assembled tubular stent is illustrated in FIG. 1, a separation between distinct radial modules can promote a relative degree of flexibility at these junctions (the regions of cutting lines AA, BB and CC).

Further, FIG. 2 shows an assembly 660 with a plurality of backbones 662a-c. The plurality of rail members 664 are arranged in an overall cross-over pattern with respect to adjacent rail members. In this arrangements, cutting lines A'A' and B'B' can be seen to necessarily cross one or more rail members in traversing the array of backbones. In this sense, the rail members may be described as being integrated in a cross-over or partial overlap arrangement, without distinct or separated radial modules. As discussed above, in the assembled tubular stent, such a cross-over arrangement can promote radial strength and continuity along the axis of the stent.

As with other embodiments of this disclosure, the concepts illustrated in FIGS. 1 and 2 may be used in combination. For example, one or more portions of the stent length may have a crossover pattern (e.g., a robust center section adjacent a lesion or plaque being supported radially), while other portions may be arranged as distinct modules (e.g., distal and proximal terminal modules suited to flexing to vessel contours).

Rail Pattern Perpendicular to Helical or Slanted Backbones

While many of the examples described herein have patterns of rail members oriented generally perpendicular relative to the stent longitudinal axis 640 (and generally obliquely oriented with respect to the helical or slanted portions of the backbones), alternative arrangements may be employed without departing from the unique and novel aspects disclosed herein.

For example, FIG. 3 shows an assembly 670 with three backbones 672a-c, arrayed generally parallel with one another, and set at an angle relative to the stent longitudinal axis 640. The rail elements 674, however, are generally aligned perpendicular to the backbones 672a-c. As may be seen in Arrow 677, the direction of sliding of the toothed portion of the rail member 674 with respect to the backbone pass-through slot is at an angle to the stent axis.

Note that in FIG. 3, as well as in several of the figures beginning with FIG. 1, the elements of the stent assembly may be shown in an untrimmed or unfinished configuration, with portions 676a of the rail members extending outward beyond the bonding slots of the backbone. These portions are provided for manufacturing convenience during assembly and the bonding and/or affixing of rail elongate portions to backbone structure. The extended portions may be trimmed to final shape 676b by known methods (blades, laser cutting, and the like) during the final assembly process. Similarly, in many of the figures, an extended proximal and distal portions of backbones is shown, which may be trimmed to a final desired length as a manufacturing procedure.

Non-Slanted Backbone Portions

It is often desirable to have the stent deploy or expand within a lumen in a uniform manner along its axis. In other cases, it may be desired to have portions of the stent deploy before or later than others. A balloon-based deployment system may tend to apply greater force or pressure at certain points along the stent axis, or inflate sooner at different longitudinal points. The stent structure may be tailored to achieve the desired deployment sequence.

In at least some deployment scenarios it may be advantageous, at certain longitudinal portions of the stent backbones, to have less mechanical resistance to expansion of the rail members through the pass-through engagement elements, than at other longitudinal portions. For example, where a balloon catheter deployment system tends to inflate more readily in the center than at the terminal ends, it may be advantageous to compensate for this by having less resistance to expansion of the terminal portions of the stent (or one end) than in a center portion. Thus, in some arrangements the stent can advantageously be configured to mitigate non-uniform expansion of the balloon catheter, e.g., the stent can be configured to expand substantially uniformly although the balloon catheter expands non-uniformly.

Figure 4A:
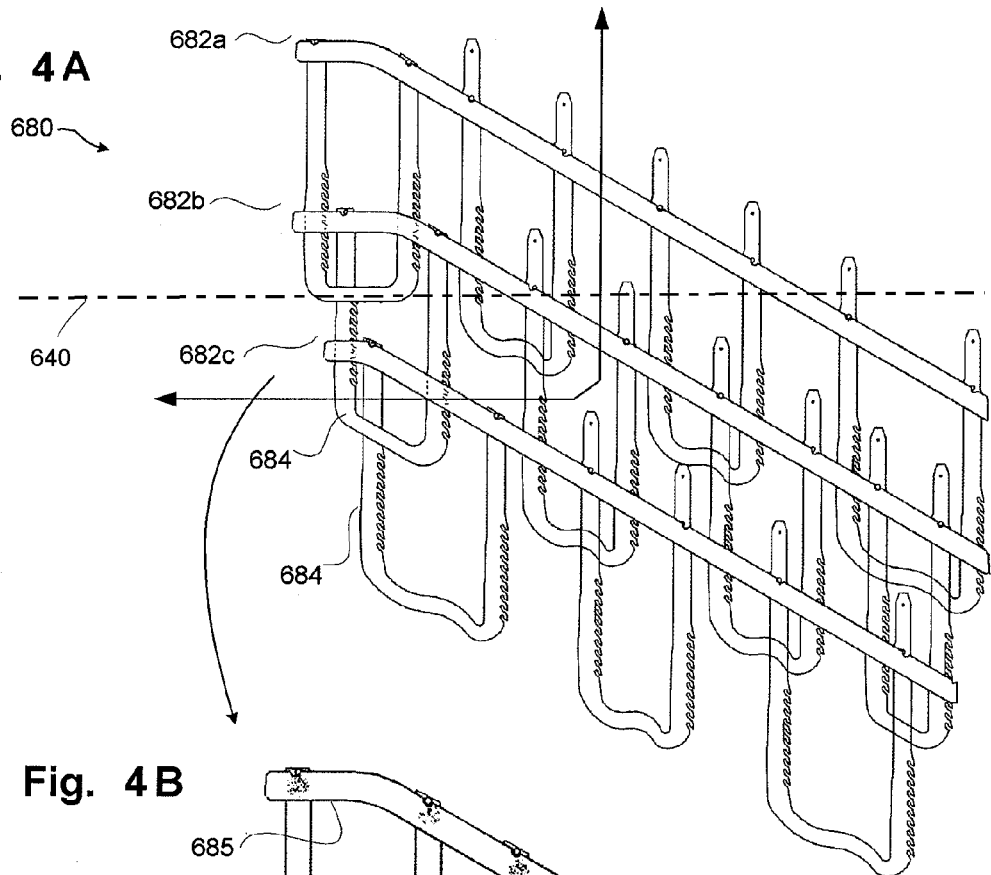
FIGS. 4A and 4B show a stent assembly with backbones arrayed generally in an slanted or helical orientation, having portion which is parallel to the stent axis, according to an embodiment.
Figure 4B:
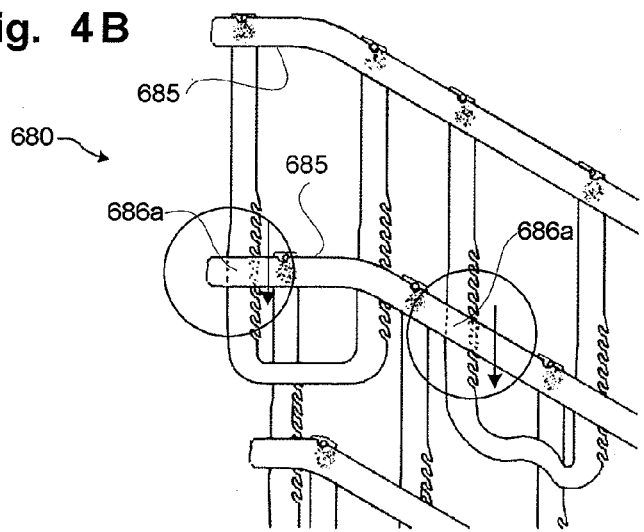

FIGS. 4A and 4B show a stent assembly 680 with three backbones 682a-c, arrayed generally parallel to one another in an locally slanted or helical orientation. FIG. 4B is a detail of the upper-left corner of FIG. 4A. Rail members 684 are arranged bonded to the backbones and passing though slots in adjacent backbones. However, one or more of the backbones (e.g., all three in the example illustrated) may have a portion 685 which is less slanted or generally parallel to the stent axis. This less slanted or generally parallel portion 685 can facilitate motion of the rail elongate elements 684 through the pass through slots being generally parallel to the backbone at the un-slanted portion 686a, and generally oblique to the backbone at slanted portion 686b.

In certain cases, in an assembly of generally helically aligned or slanted backbones, a short section of backbone parallel to the axis of the stent at a terminal end of the stent cab enhance radial rigidity of the stent, particularly where the terminal end is supported by the last rail in sequence of the array, such as the left-hand portion of 682a. Thus a non-slanted terminal backbone portion may be advantageously included one or more of the backbones of a stent assembly, e.g., stent assembly 680.

FIG. 5 shows a stent assembly 690 with three backbones 692a-c arrayed generally parallel to one another in a generally slanted or helical orientation. Similar to the example shown in FIGS. 4A and 4B, one or more of the backbones 692a-c can include multiple portions that are locally non-slanted or less-slanted (e.g., generally parallel to the stent longitudinal axis 640). In FIG. 5, several of these portions are marked with circles. For example, in some embodiments, one or more of the left end, right end, and/or a middle portion of at least one of the backbone 692a-c can contain such a non-slanted or less-slanted portion. In the particular example illustrated in FIG. 5, each backbone has three spaced-apart non-slanted portions. As shown, rail pass-through slot portions 696a can be provided with a perpendicular backbone-rail member alignment where the backbone portion is non-slanted. In this manner the deployment characteristics of the assembly may be tailored along the longitudinal axis of the stent, while maintaining an overall slanted or helical backbone pattern.

Bi-Directional, Multi-Directional or Variable-Directional Backbone Arrays

While many of the examples described have patterns of backbones oriented generally helical array, generally at a consistent angle to the stent longitudinal axis, alternative arrangements may be employed without departing from the unique and novel aspects disclosed herein.

Figure 6:
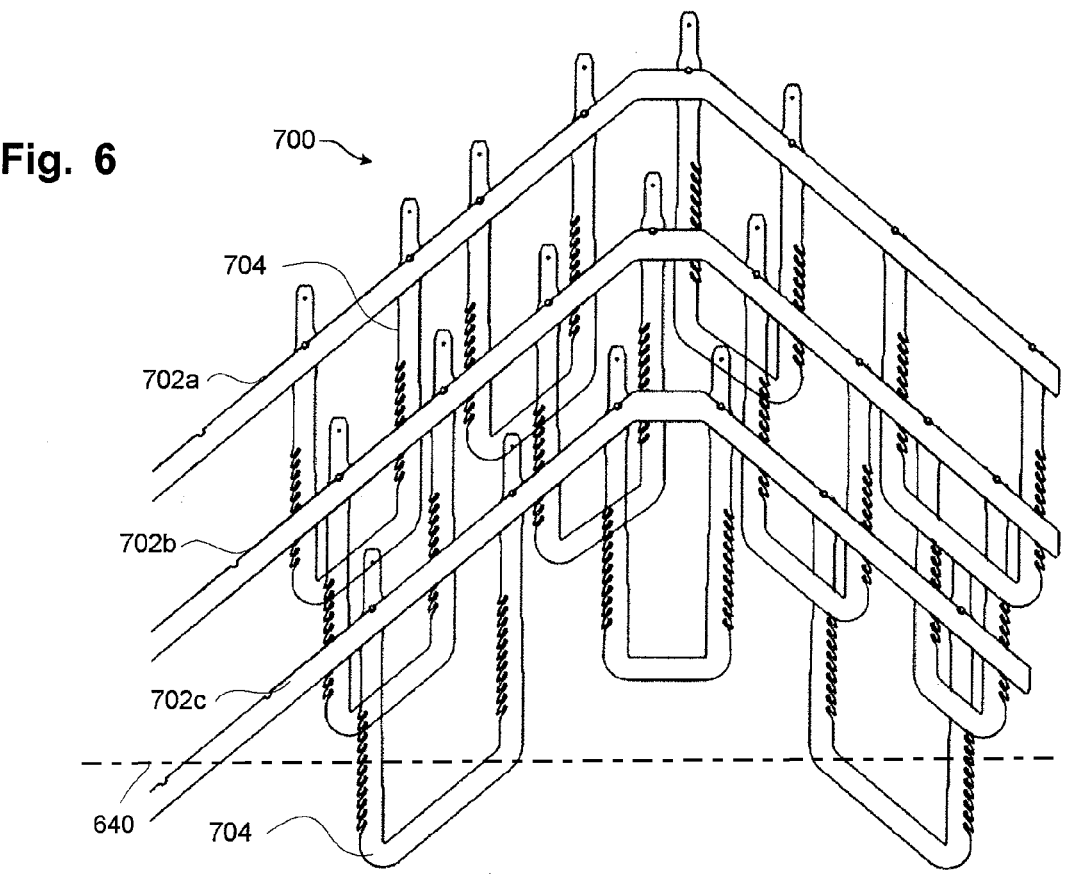
FIGS. 6, 7, and 8 each show embodiments of stent assemblies in which the backbones have bi-directional, multidirectional or continuously variable backbone orientation along the stent longitudinal axis, according to an embodiment.

In the example assembly 700 shown in FIG. 6, each backbone 702a-c has a slant angle that reverses at the mid-portion of the assembly. As shown, some embodiments can further include a medial non-slanted portion. As noted above, the inventors have noted that a "non-reversing" helical stent tends to unwind from either end toward the center, which creates binding and increased resistance to expansion in the center of the stent. Surprisingly, the inventors have determined that creating a stent with a reversing helical backbone and positioning the peak or apex of the reversing helical backbone at about the midpoint of the stent can reduce the tendency of the stent to bind during expansion.

However, by implementing the reversing helix illustrated in FIG. 6, the inventors have surprisingly determined that deployment of the stent can be more uniform and that binding is reduced in the center of the stent. In solving this problem, the inventors have also noted that a decreased amount of binding attributable to the helical arrangement takes place at approximately the one-quarter and three-quarter marks of the stent—the points between the ends and the center point where the helix reverses. Accordingly, as discussed further herein, the inventors have invented new and unique solutions for reducing and/or eliminating binding of the stent in these and other areas where localized binding may build.

Figure 7:
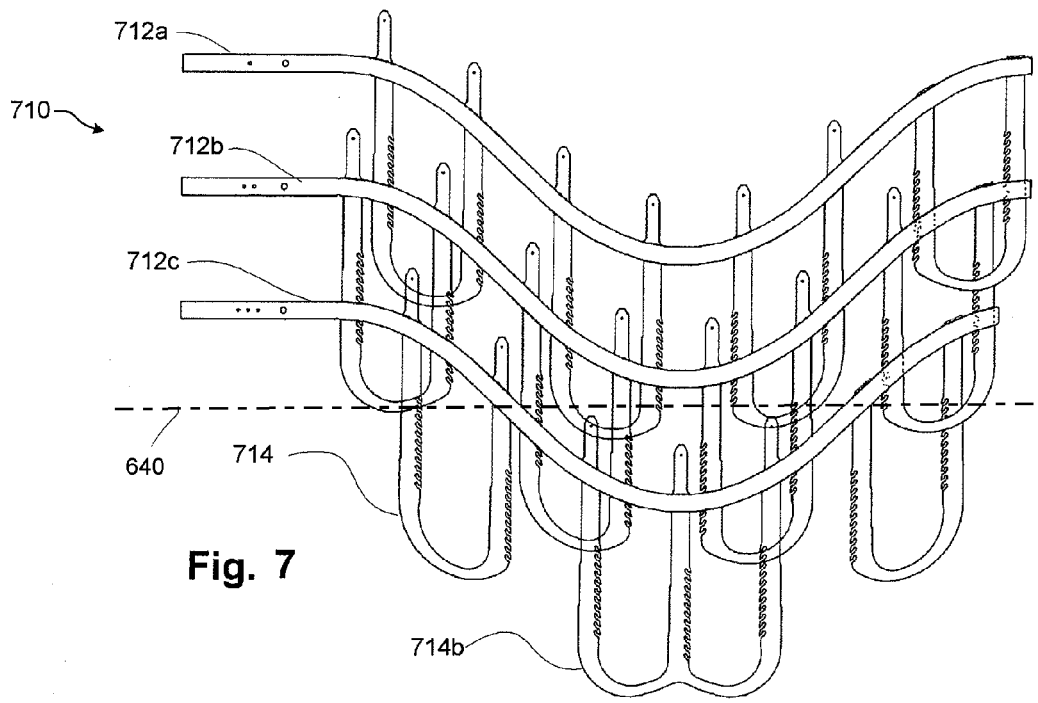

In the example assembly 710 shown in FIG. 7, each backbone 712*a-c* includes a curvilinear portion and defines has a slant angle or slope (with respect to the stent axis) that is continuously variable from proximal end to distal end. This continuously variable curve extending between respective peaks and valleys of the backbones can provide superior flexibility and deployment characteristics, as discussed herein. In the illustrated embodiment of FIG. 7, the slope changes from negative to positive (as viewed from left to right in the figure) at the valleys of the backbones or midpoint of the assembly, giving the backbone an overall cosine wave appearance in this illustration. The rounded apex of the cosine wave can inhibit the apex from protruding into the lumen when the stent is in the rolled configuration. Avoiding such protrusions can be advantageous at least for the reason that such protrusions can block flow through a portion of the lumen. Additionally, inhibiting the apex from protruding into the lumen, can facilitate an overall round shape of the stent, as discussed above. Further, compared to a stent having a sharply angled peak (which could become entangled with or even puncture vasculature or the catheter balloon) the rounded apex of the cosine wave can generally slide against vasculature or the catheter balloon, thus facilitating delivery and deployment of the stent assembly.

Figure 8:
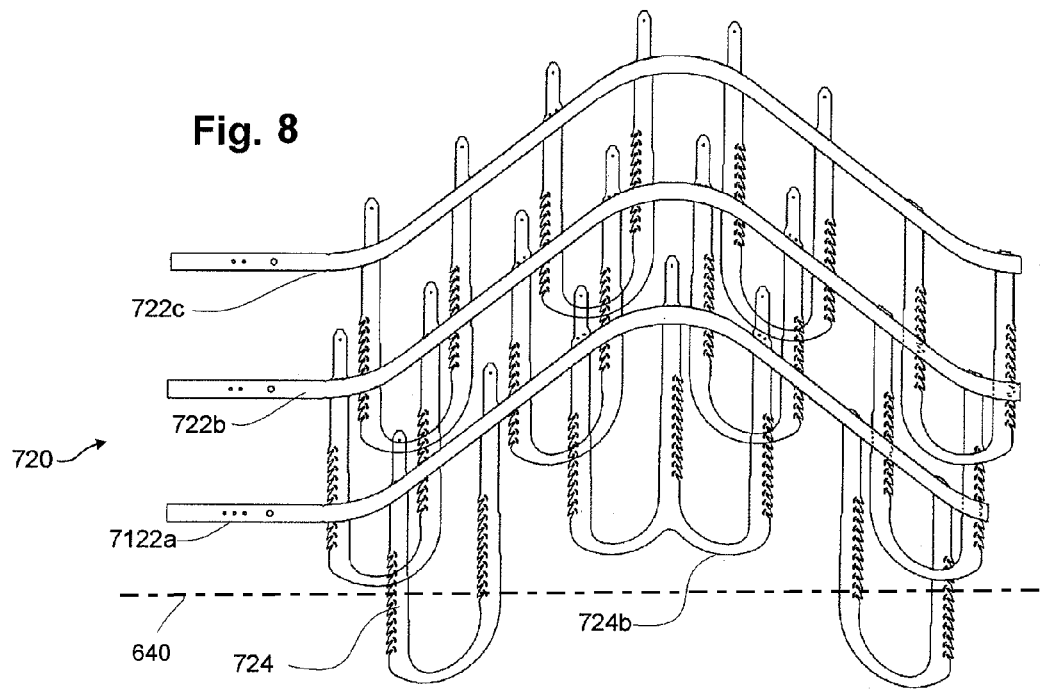
Figure 9C:
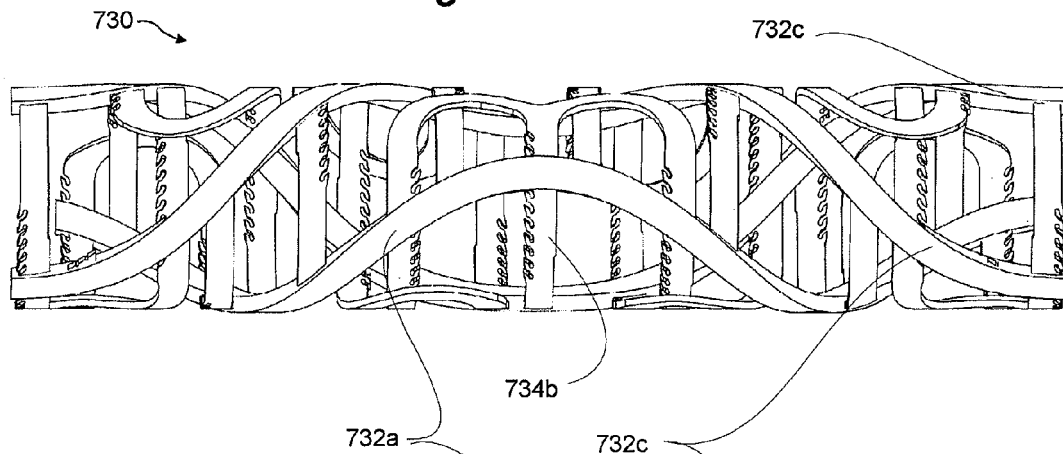
Figure 9D:
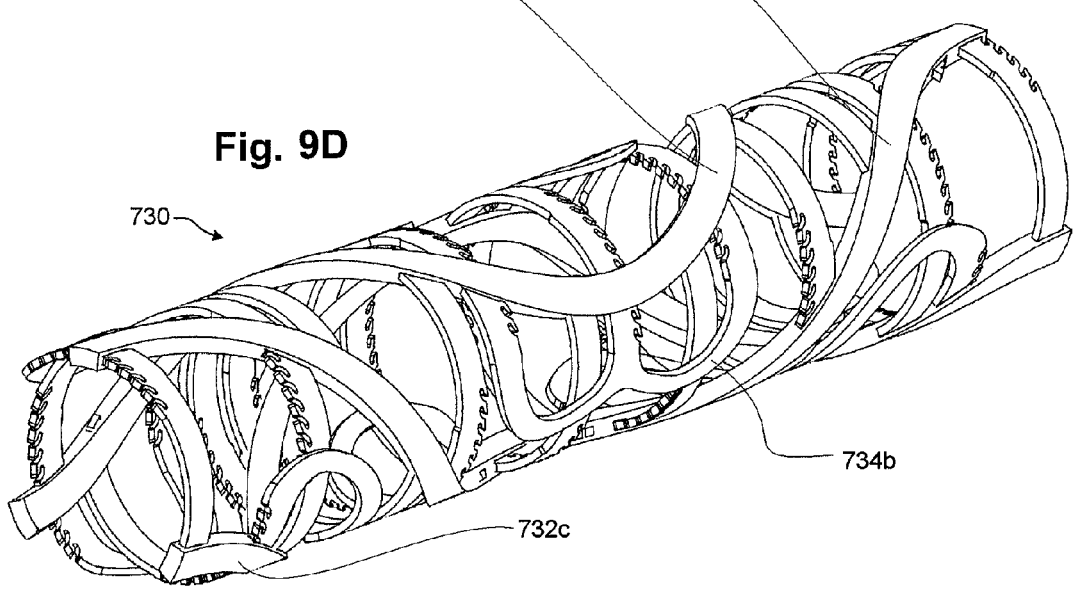

Like the example of FIG. 7, in the example assembly 720 shown in FIG. 8, each backbone 722*a-c* includes a curvilinear portion and also has a slant angle or slope (with respect to the stent axis) that is continuously variable from proximal end to distal end. In the illustrated embodiment, the slope changes from positive to negative (as viewed from left to right in the figure) at the peaks of the backbones or midpoint of the assembly, giving the backbone an overall sine wave appearance in this illustration. As discussed above, the rounded apex of the wave can inhibit the apex from protruding into the lumen of the stent, can promote a more round overall stent shape, and can avoid entanglement during delivery and deployment. Further, as shown, in some cases a trident or W-shaped rail member 714*b* or 724*b* can be provided at the apex of the sine or cosine shape or enhancing flexibility and strength of stent at the peaks or valleys of the backbones.

In the examples of FIGS. 7 and 8, the backbone array provides a smooth transition between portions that are minimally sloped and portions that are markedly sloped. Many of the other embodiments illustrated in the appended figures provide similar advantages.

The absolute value of the overall helix angle (the angle at which a backbone extends relative to the longitudinal axis 640 of the stent) of the backbones of embodiments of the stent can be between at least about 15 degrees and/or less than or equal to about 60 degrees. The absolute value of the overall helix angle of the backbones can also be between at least about 20 degrees and/or less than or equal to about 50 degrees. Further, the absolute value of the overall helix angle of the backbones can be between at least about 22 degrees and/or less than or equal to about 30 degrees. In some embodiments, the absolute value of the overall helix angle of the backbones can be about 25 degrees.

Bi-Directional or Multi-Directional Rail Member Arrays

While many of the examples described have patterns of rail members or radial elements oriented in a consistent direction from proximal to distal end of the array, alternative arrangements may be employed without departing from the unique and novel aspects disclosed herein.

FIGS. 9A-9D illustrate an embodiment that provides an improved deployed shape of the stent. In some embodiments it may be desirable for the deployed stent to be substantially round, e.g., circular in cross-section. The illustrated embodiment includes one or more components, such as a longitudinally-extending structure (e.g., a backbone) and a unique rail member arrangement that promotes the roundness of the stent. In some embodiments, excellent results for further promoting stent roundness have been found by implementing configurations in which rail members are selectively oriented in opposing circumferential directions.

For example, some embodiments, a first rail member can extend circumferentially in a first direction and a second rail member can extend circumferentially in a second direction. In the example assembly 730 shown in FIGS. 9A-9D, the direction of orientation of arrays of the rail members or radial elements is reversed at the peaks of the backbones or at a midpoint of the stent assembly. In this particular example, the backbones 732*a-c* are arrayed similarly to the example of FIGS. 7 and 8, e.g., each backbone 732*a-c* is generally curvilinear and has a slant angle or slope with respect to the stent axis that changes direction of slope in the middle portion. Thus, the backbones can be described as reversing helical backbones having smooth or curved peaks and valleys.

With respect to the peaks or middle portion of the backbone array (shown in the expanded position in FIG. 9A and in the collapsed position in FIG. 9B), the rail members 734 are oriented with cross-members 735 of the U or W shaped rail members extending "upward" (in the drawing), and thus extending to the "outside" of the adjacent backbone curvature 732*a*. With respect to the left and right end portions of the backbone array, the rail members are oriented with cross-members 735 of the rail members 734 extending "downward" (in the drawing), and thus also extending to the "outside" of the adjacent backbone curvature 732*c*.

In the illustrated embodiment, as in the embodiment of FIGS. 1 and 2, the middle portion of the rail member array is a distinct radial module from the end portions. In other words, the embodiment illustrated in FIG. 9A illustrates three radial modules that are spaced apart from each other and provide, in a tubular member, independent circumferential modules. However, within the middle portion, the rail members form a crossover arrangement. Accordingly, as discussed above, in such an embodiment the middle portion can include enhanced radial strength and continuity along the axis of the stent, while the end portions can have enhanced flexibility to flex to vessel contours.

In some arrangements, the direction in which the first and second rail members extend can be related to or dependent upon the angle between the rail member and longitudinally-extending structure. For example, in some cases, the first and second rail members extend in a given circumferential direction such that the angle between the rail member and longitudinally-extending backbone or structure is an acute angle. Accordingly, it has been determined that, compared to stents with other features, e.g., non-reversing structures, a reversing helical backbone can promote roundness of the stent.

As shown, the backbone can be shaped substantially as a sinusoid. In particular, at least one peak of the sinusoidal backbone can be curved, e.g., not formed as a pointed peak or having a sharp angle. Such a rounded peak can further promote an overall rounded shape or roundness of the stent. For example, the rounded peak can reduce the tendency for the peak to protrude into the lumen of the stent.

Enhanced Tooth Deflection and Resiliency

FIGS. 10A-10F illustrate alternative embodiments of the teeth or locking members provided on the elongate elements or rails of the various embodiments shown herein for engaging with the backbones in or adjacent the pass-through slots. Each of FIGS. 10A-10F shows a portion of rail 774 including a plurality of teeth 772. In some embodiments, the teeth are positioned on multiple edges of each elongate element. In other embodiments, the teeth are on positioned a single edge, such as is shown in FIGS. 10A-10F.

The embodiments shown the FIGS. 10A-10F each have one or more relieving openings 776 located within the rail member, which can reduce stress concentrations as the teeth 772 are deflected as they pass through the slot during stent expansion. In some cases, the relieving openings 776 may decrease force needed to deflect the teeth 772. Advantageously, the relieving opening 776 can also promote stiffness of the tooth in the opposite direction, thus enhancing the one-way ratcheting configuration of the stent. Further, such relieving openings 776 can allow for a shallower configuration of the teeth to be employed, thus promoting manufacturability and reducing the amount of material than is removed to form the teeth 772.

Such relieving openings 776 may extend through the material of the rail 744 (open holes) or may only extend partially through the material on one or both sides (indentations). The relieving openings 776 may, for example, prevent or reduce stresses in the teeth 772 during deployment so as to avoid or reduce plastic deformation, and to increase the effective rebound of the tooth as it passes beyond the pass-through slot of the backbone.

Note that the teeth 772 need not necessarily have a tooth-like appearance, and alternative profiles may be employed, as shown in FIGS. 10E and 10F. In these embodiments, the locking portion is rounded, and depresses inward under the forces of deployment.

FIGS. 11A-11D show the action of engagement teeth or locking members provided on the elongate elements or rails of the rail members, configured for engagement with slots in the backbones of the stent embodiments described herein. In some respects, the example shown is particularly similar to the locking mechanism depicted in the embodiments of FIGS. 12A-14B, discussed below. In the example of FIGS. 11A-11D, the rail member 770 includes a pair of elongate rails 773a and 773b (note: there may be more than two, e.g., see member 724b in FIG. 8).

A reference frame for the rail member 770 may be defined relative to the backbone to which it is to be fixedly mounted, joined or bonded in the assembled stent. In this reference frame, each of rails 773a-b of member 770 has a proximal end 772a-b configured to be fixedly mounted or bonded to a supporting backbone (e.g., 782a in FIG. 12A). In this reference frame, the rail elements 773a-b, as assembled, will extend distally to engage a sliding slot 787 of an adjacent backbone (e.g., 782b in FIG. 12A). Each of rails 773a-b includes a medial portion 774a-b supporting a locking mechanism 776a-b. In the illustrated embodiment, the locking mechanism 776 is disposed on only one side of rail 773. Other embodiments have at least some of the locking mechanism 776 disposed on both sides of the rail 773a and/or 773b. The rails 773a and 773b are joined at their distal ends by cross-member 775. In alternative embodiments, where member 770 has more than two rails, cross-member 775 may join more than two rails.

In the detail drawing FIG. 11B, it may be seen that the locking mechanism 776 comprises a sequential plurality of locking elements 777, which are illustrated as being tooth-like in this example. The locking elements 777 can be separated by indented connecting regions 778. In some cases, at least one stress management or relieving opening 779 is disposed adjacent connecting regions 778. The relieving opening 779 can facilitate adjustment of the characteristics (e.g., flexibility, rebound, and the like) of the locking elements 777 by the selection of the shape, position, and/or size of the opening 779.

Figure 11C:
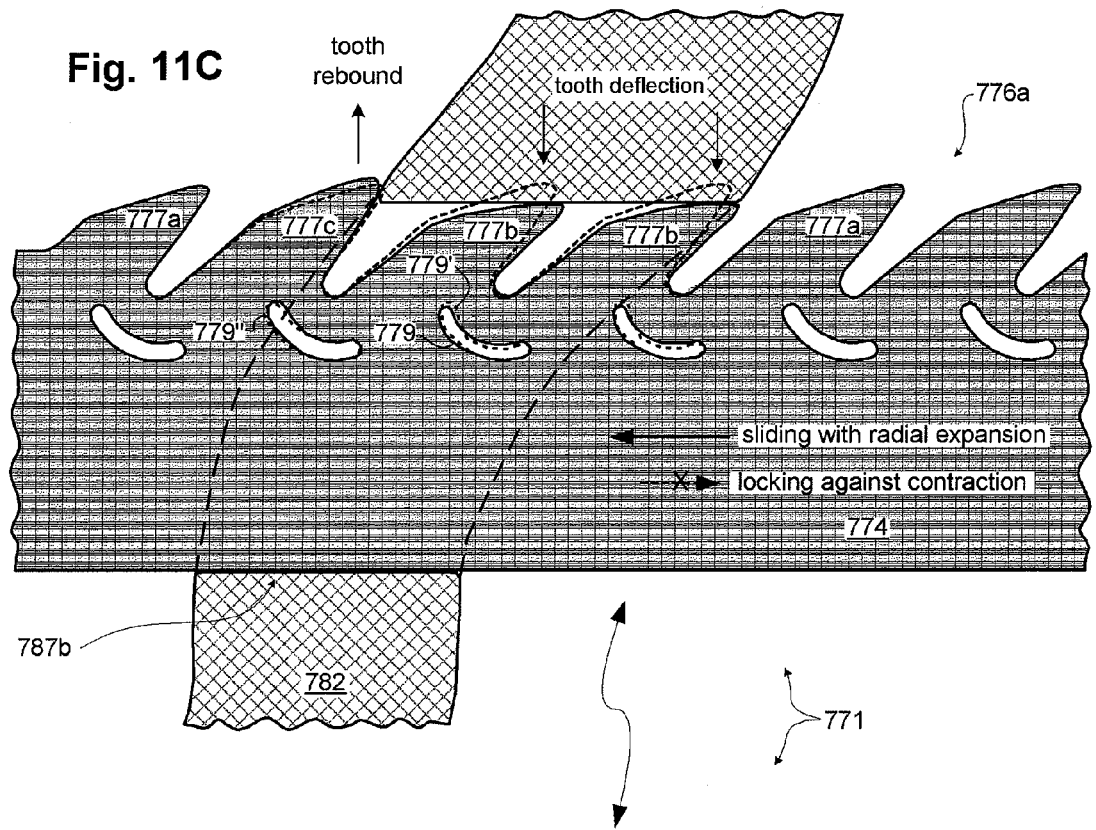
Figure 11D:
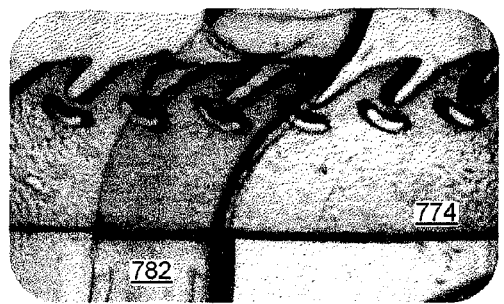

The drawing of FIG. 11C and the photograph of FIG. 11D depict a stent locking assembly 771 composing the medial portion 774 disposed to pass through slot 787b of the backbone 782. During radial expansion of the stent upon deployment, one or more of the locking elements or teeth 777a can enter the proximal opening of slot 787b and become deflected inward by engagement with the slot. This deflection is illustrated by deflected tooth 777b, seen together with the superimposed undeflected shape as a dashed line. It may be seen that, as the adjacent tooth 777b is deflected, the relieving opening 779 may also deform under the deflection stress to a deformed shape 779', shown as a dashed line.

As the tooth element 777c passes distally beyond slot 787b, the tooth 777b rebounds to approximately the shape of the un-deflected tooth 777a, so as to prevent radial contraction (proximal motion of rail portion 774). Relieving opening 779 may be configured to reduce or eliminate plastic deformation of locking mechanism 776 as the locking elements 777 are deflected during slot engagement, so as to improve the rebound of deflected tooth 777b. The shape of tooth 777a upon rebound is configured to inhibit the tooth 777a from re-entering the distal opening of slot 787b, so as to inhibit contraction of the stent. In this process, the tooth 777c may deflect outward to increase the positive nature of the locking assembly 771. The relieving opening 779 may deform under the locking stress to form a different shape 779".

Stent Assemblies with Extended Rail Arrays

Figure 12B:
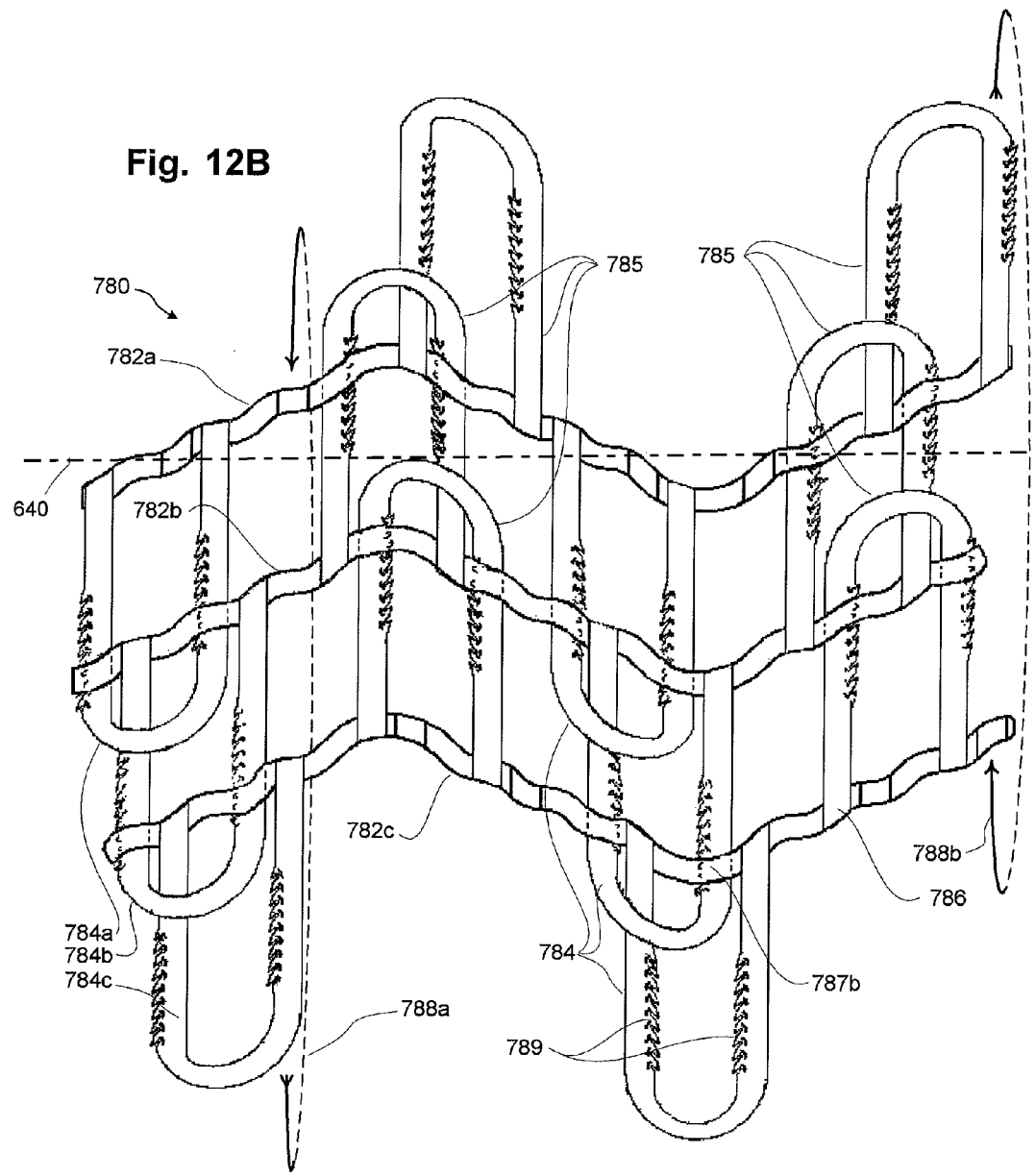
FIG. 12B illustrates the stent embodiment of FIG. 12A in the expanded state, according to an embodiment.

FIGS. 12A and 12B depict an alternative stent embodiment 780, in which additional modules of rail members are included. Like the embodiment of FIGS. 9A-9D, the embodiment 780 has at least a first module of rail members 784 directed in a generally perpendicular direction relative to the stent axis (e.g., downward in the illustrations of FIGS. 12A and 12B), and at least a second module of rail members 785 directed generally opposite the first module of rail members 784 and generally perpendicular relative to the stent axis (e.g., upward in the illustrations of FIGS. 12A and 12B).

In the example shown in FIGS. 12A and 12B, each of the modules 784, 785 can comprise a group of three overlapping rail members 784a-c, 785a-c. Each rail member can be joined or mounted to at least one backbone (three backbones 782a-c are illustrated) at attachment point 786. Each rail member 784 can comprise a plurality of space-apart generally parallel rails 784', 784" that can be connected by a distal cross member 784". Rail members 785 can be similarly structured.

In addition to being proximally mounted to at least one backbone, each of the individual rails or the rail members 784a-c, 785a-c can engage and pass slidably through a slot 787 in an adjacent backbone. As discussed above, although FIGS. 12A and 12B diagrammatically show assembly 780 as planar shape, these figures represent a generally tubular stent assembly 780. As shown by arrow 788a, the rail members 784c mounted to backbone 782c can be configured to pass slidably through slots of adjacent backbone 782a, and similarly arrow 788b indicates that rails member 785a mounted to backbone 782a can be configured to pass slidably through slots in backbone 782c.

FIG. 12A illustrates a compacted form of stent assembly 780, in which the toothed portion 789 of each rail of rail members 784a-c, 785a-c is positioned distal to the corresponding engagement slot 787 (indicated as 787a). In some embodiments, the backbones 782a-c are disposed closely adjacent one another and/or nested. In some embodiments, in the compacted configuration, the stent 780 is configured to mount on a collapsed balloon catheter.

FIG. 12B illustrates a radially expanded form of the stent assembly 780, in which the toothed portion 789 of each rail of the rail members 784a-c, 785a-c is positioned at least partially within the corresponding engagement slot 787 (indicated as 787b). In some embodiments, in the radially expanded state of the stent 780, the backbones 782a-c are disposed at a substantial separation from one another, as would typically be configured for deployment at a larger tubular diameter supporting a treated vascular or other body lumen. In this configuration the toothed portion 789 can inhibit radial contraction of the stent 780.

In the illustrated embodiment, each backbone 782a-c has an overall slant angle or slope θ (with respect to the stent axis) and can be disposed as a generally helical portion in the tubular stent body. In some embodiments, the overall slope angle θ reverses (shown as +θ and −θ in FIG. 12A) adjacent each rail module 784, 785, so as to form an overall zig-zag shape. In the example shown, each backbone includes three distinct helical portions of substantial pitch, and the stent assembly 780 comprises four rail modules, each oppositely aligned relative its each adjacent rail modules. In the example shown in FIGS. 12A and 12B, the slope angle θ of each portion is about 25 degrees, although it may be greater or less than this.

Figure 13A:
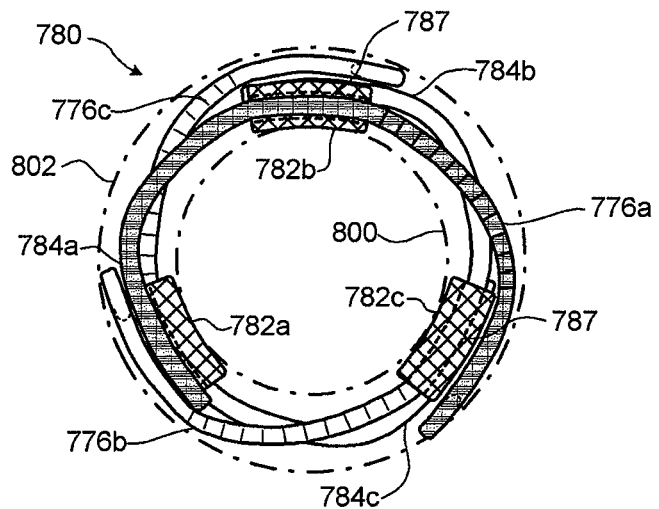
FIG. 13A illustrates an end view of the stent embodiment of FIG. 12A in a tubular configuration, according to an embodiment.
Figure 13B:
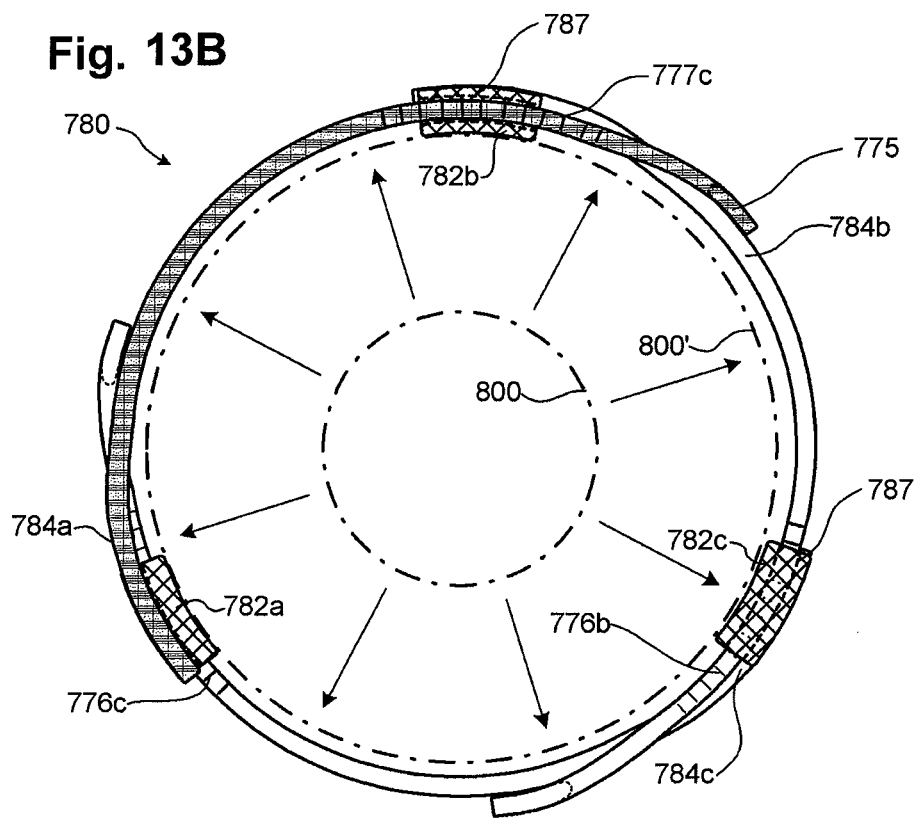
FIG. 13B illustrates an end view of the stent embodiment of FIG. 12B in the tubular configuration, according to an embodiment.

FIGS. 13A and 13B illustrate end-on views (looking down the open lumen) of the stent 780 in the compacted and expanded stent configurations, respectively. In these figures, stent 780 is viewed as if viewing the perspective view of FIG. 14A looking at the axis of the drawing from the right hand side. The view is, in essence, a cross section of the stent through rail member 784a. These views also correspond to viewing the assembly 780 in FIGS. 12A and 12B from the left hand side of the figure plane (when the stent is in the rolled configuration).

As may be seen in the compacted configuration of FIG. 13A, the rail member 784a is mounted at its proximal end to backbone 782a. Rail member 784a extends clockwise in the figure to pass through slot 787 in adjacent backbone 782b. As shown, the locking mechanism 776a normally is positioned beyond the slot 787 when the stent 780 is in the compacted configuration. The other backbone and rail member assemblies 782b-784b, 782c-784c are disposed and configured similarly in clockwise fashion, each rail member 784b, 784c also passing through a slot 787 in an adjacent backbone. A deflated balloon catheter 800 is represented by phantom lines inside the perimeter defined by the compacted stent assembly 780. In some embodiments, a retractable/removable sheath 802 surrounds the compacted stent assembly 780 until the stent is in position within a lumen at a treatment site.

Figure 14A:
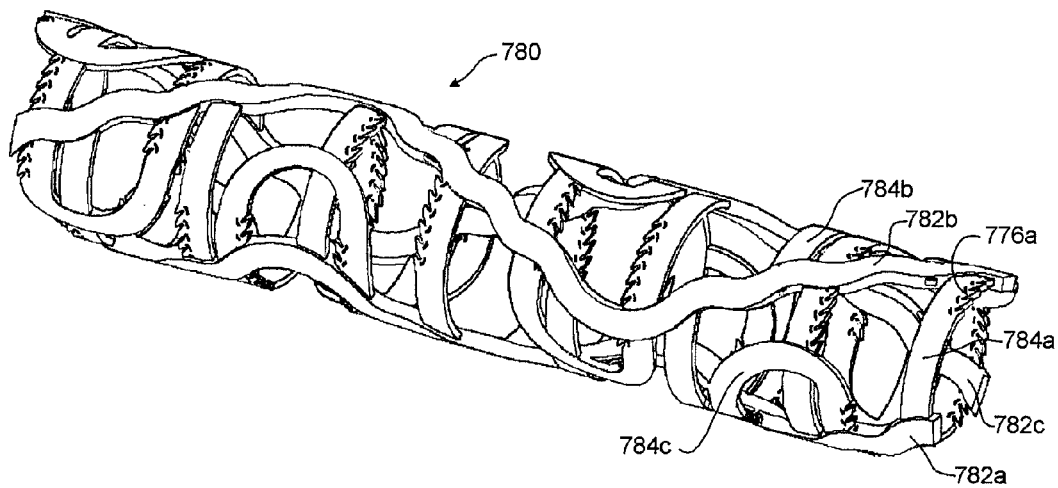
FIG. 14A illustrates a perspective view of the stent embodiment of FIG. 12A in the tubular configuration, according to an embodiment.

As may be seen in the radially expanded configuration of FIGS. 13B and 14A, the balloon 800 of the catheter assembly has been inflated to an extended diameter 800', expanding the perimeter of stent assembly 780 radially outward. During such expansion, each backbone 782a-c generally moves circumferentially farther away from each adjacent backbone than it was in the compacted state. As a result, each rail member 784 moves with respect to its respective engagement slot 787 such that after the expansion the engagement slot 787 is positioned at a more distal portion of the rail member 784. Such movement eventually results in the locking mechanism 776 being at least partially engaged within the slot with at least one of the locking elements 777 inhibiting radial contraction of the rail member 784, e.g., in the manner shown in FIGS. 11C and 11D. Note that cross member 775 of each rail member lies at the outside the perimeter defined by adjacent rail members, spanning across these adjacent rail members. Such an arrangement advantageously can maintain the distal end of the deployed rail member 784 securely outside of the vascular lumen following retraction and removal of the balloon catheter 800.

Figure 14B:
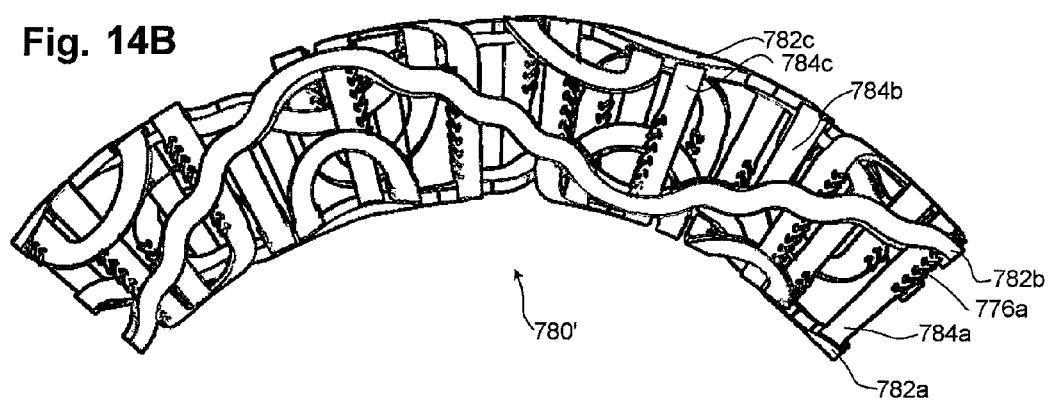
FIG. 14B illustrates a flexed or bent configuration of the stent embodiment of FIG. 12A in the tubular configuration, as potentially deployed in a curving vascular lumen, according to an embodiment.

FIG. 14B illustrates a flexed or bent configuration of stent assembly 780 as deployed in a curving vascular lumen. In some embodiments, the spring-like configuration and longitudinal continuity of the plurality of backbones 782a-c can permit the tubular assembly to be smoothly flexed to follow a curved lumen. Additionally, in some embodiments, the regular rib-like structure comprising a plurality of circumferentially aligned rail members 784a-c, 785a-c can provide radial strength and support for the lumen wall.

Figure 15A:
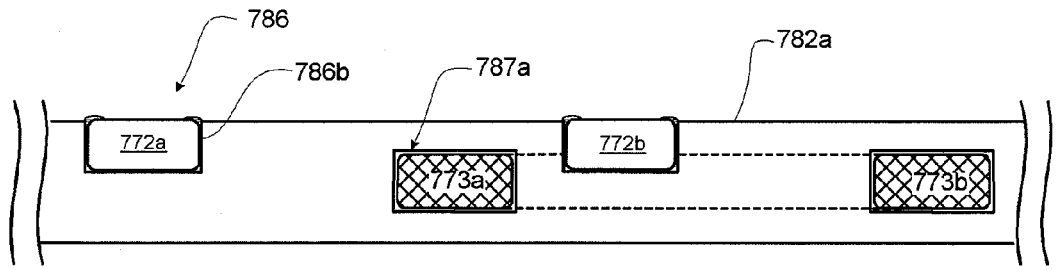
FIGS. 15A and 15B schematically illustrate the relation of backbones to rail members, according to an embodiment.
Figure 15B:
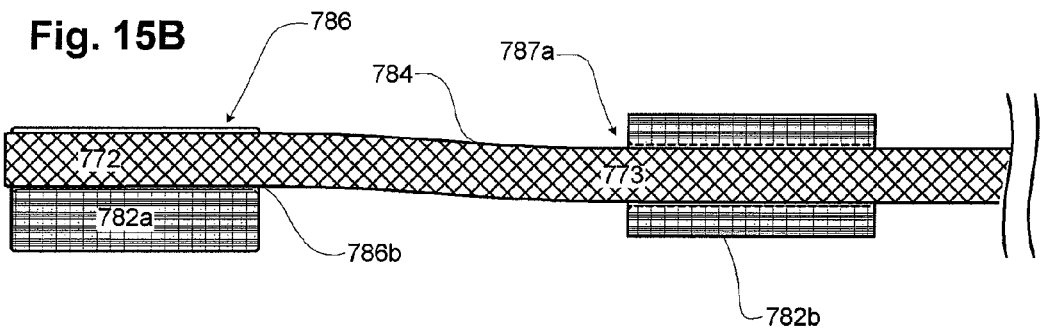

FIGS. 15A and 15B illustrate schematically the relation of the backbones (e.g., 782a and 782b) to the rail members 784. FIG. 15A is a cross-sectional side view of a portion of backbone 782a, illustrating the proximal ends 772a-b of one rail member mounted in backbone recess 786 (e.g., by adhesive or solvent bond 786b), and showing the elongate rail elements 773a-b on and adjacent rail member passing through the slots 787a of the backbone. FIG. 15B illustrates a single rail member 784 in cross section, having a proximal portion 773 mounted to backbone 782a at recess 786, and passing through slot 787a of adjacent backbone 782b.

Overall and Localized Backbone Slope

Figure 16:
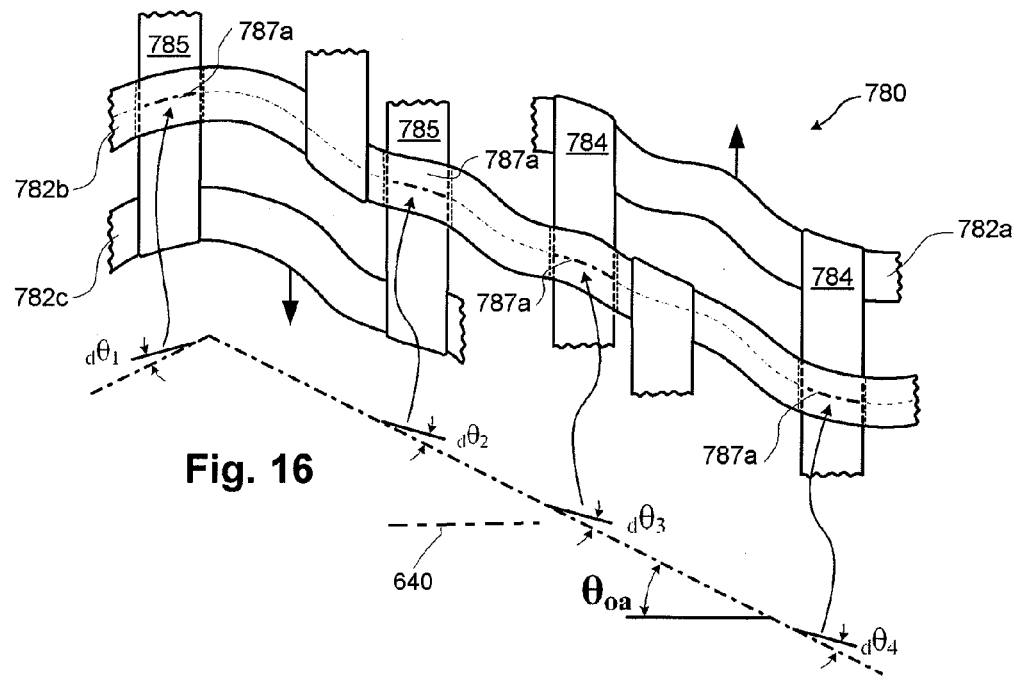
FIG. 16 illustrates a detail of a mid portion of the stent assembly of FIG. 12A, according to an embodiment.

FIG. 16 is a detail of a mid portion of the compacted stent assembly 780 shown in FIG. 12A, and the elements are labeled as in FIG. 12A. As shown, the backbone 782b can include an overall helix angle for the backbone portion shown ($\theta_{oa}$). In general, a steeper overall helix angle contributes to a deployed stent that has greater longitudinal flexibility and radial strength. In contrast, a shallower overall helix angle normally contributes to an assembly that may be expanded during balloon deployment with a reduced tendency to twist as it expands, thereby promoting a smoother and more uniform deployment. The overall helix angle may be selected to provide desired stent characteristics. For example, in some cases the overall helix angle is selected to balance between the aforementioned general properties.

In some arrangements, although the overall helix angle $\theta_{oa}$ may be in one direction (e.g., positive) a portion of the stent assembly 780 may include one or more regions with an opposite slope (e.g., negative). For example, the overall helix angle $\theta_{oa}$ may be negative, but a portion of the stent assembly may be positive, before reversing and trending downward again. Further, as illustrated in FIG. 17, the backbone can comprise a plurality of discrete segments. The discrete segments can be that portion of the backbone extending between engagement elements of the backbone. Further, the discrete segments can comprise the portion(s) of the backbone corresponding to the engagement elements of the backbone. In some embodiments, each of these discrete segments can comprise a discrete helix angle or slot angle. In some embodiments, such as when the discrete segment is an engagement element (such as a slot), the discrete helix angle may be referred to as a slot angle. A discussion of the overall helix angle and the discrete helix angle or slot angle follows.

Normally, the reversing helical shape of the backbone can comprise at least one portion that trends positive and at least one portion that trends negative. A positive trend is a portion or the backbone that has a positive overall helix angle, regardless of the discrete helix angles of the individual or discrete segments. A negative trend is a portion or the backbone that has a negative overall helix angle, regardless of the discrete helix angles of the individual or discrete segments. In some cases, within one or both of the positive and negative trending portions there can be one or more sections that are sloped oppositely to the trend. For example, a negatively trending portion can include a positively sloped section. Likewise, positively trending portion can include a negatively sloped section. Generally, the oppositely sloped section is minor compared to the trending portion. For example, in some embodiments the oppositely sloped section is less than about 25% of the length of the trending portion. In some embodiments the oppositely sloped section has an amplitude that is less than about 30% of the amplitude of the trending portion.

Surprisingly, a backbone having a reversing (e.g., a zig-zag) helix angle, such as is shown in FIGS. 12A and 12B, can promote an advantageous balance between these general properties so as to provide enhanced longitudinal flexibility and radial strength in combination with a reduced tendency to twist upon deployment. In contrast, a substantially continuous overall slope (such as in the backbones of the embodiment of FIGS. 1-3) does not provide the same advantages.

In addition to the generally overall helical alignment of the backbone portions indicated by angle $\theta_{oa}$, it may be seen that each helical portion (e.g., each leg of the zig-zag) has a local reversing helical shape, e.g., a small-pitch undulation or waviness. Contrast the small-pitch undulation or waviness of the backbones 782a-c of FIGS. 12A-12D with the backbone alignment shown in FIG. 9A. This localized non-uniformity results all or some of the slot 787 having a characteristic centerline slope incrementally different than the overall slope, the difference denominated $d\theta_1$, $d\theta_2$, $d\theta_3$, $d\theta_4$, ... $d\theta_n$.

In the example shown in FIG. 16, each slot portion 787a has approximately the same value of $d\theta$ relative to the overall helical angle $\theta_{oa}$, although this need not be so. The values of $d\theta$ may each be different from adjacent slots and may have a positive variation or negative variation. For example, FIGS. 17A-C illustrate plan, elevation, and partial focused views of an example backbone 792 that is generally similar to the backbone 782a (shown in FIGS. 12A and 12B) and has different $d\theta$ values. In this example, the overall helix angle of each of three slanted portions (the three legs of the zig-zag) is about 25 degrees or –25 degrees. As discussed further above, the absolute value of the overall helix angle of the backbone can be between at least about 15 degrees and/or less than or equal to about 60 degrees. The absolute value of the overall helix angle of the backbones can also be between at least about 20 degrees and/or less than or equal to about 50 degrees. Further, the absolute value of the overall helix angle of the backbones can be between at least about 22 degrees and/or less than or equal to about 30 degrees. In some embodiments, the absolute value of the overall helix angle of the backbones can be about 25 degrees. As shown, the plurality of slots 797 are normally distributed longitudinally along the backbone 792 to provide sliding engagement for an array of rail members, such as members 784, 785 in FIGS. 12A and 12B.

The approximate angle of the mid-line of each slot 797 is indicated. As shown, this embodiment includes a relatively small slot angle of about 10 degrees, and medium slot angle of about 33 degrees and a steeper slot angle of about 40 degrees. Of course, this embodiment is only one example and various other slot angle values and arrangements are contemplated. In some embodiments, the absolute value of the slot angle can be between at least about 0 degrees and/or less than or equal to about 60 degrees. The absolute value of the slot angle can also be between at least about 10 degrees and/or less than or equal to about 50 degrees. Further, the absolute value of the slot angle can be between at least about 20 degrees and/or less than or equal to about 40 degrees. The slot angle can also vary between at least about 30 degrees and/or less than or equal to about 35 degrees. Finally, as illustrated, the absolute value of the slot angle can be approximately 10 degrees, 33 degrees, 40 degrees. Further, it is contemplated that the slot angle can be any variety or combination of desired angles that are configured to facilitate ease of expansion on the one hand and stent flexibility on the other hand.

For example, in some embodiments, two of the slot angles values are equal. In some embodiments, the middle slot has the greatest slot angle value. In some embodiments, at least one of the slot angles values is equal to the overall helical angle $\theta_{oa}$. In some embodiments, the average or the median of the slot angles values is about equal to the overall helical angle $\theta_{oa}$.

Generally, a steeper slot angle enhances longitudinal flexibility and radial strength of the stent, thereby promoting a stent that is both stronger and more elastic. In contrast, a shallower slot angle generally enhances expansion of the stent deployment and reduces the tendency of the stent twist as it expands, thereby promoting a stent with a smoother and more uniform deployment.

The individualized slot angles of the slots 797 as provided by the tailored undulations or waiviness of the backbone as shown in FIG. 17B allows further refinement of deployment characteristics. Surprisingly, it has been found that a slope angle in the region of slot 787a may be selected to promote more uniform and predictable stent deployment as the stent is radially expanded by a balloon catheter at a selected vascular treatment site. As discussed above, angles may be selected to promote strength and flexibility, or a highly uniform deployment behavior. In some embodiments, angles are selected to promote a sequential opening longitudinally, for example, configured to match balloon inflation characteristics.

Figure 17D:
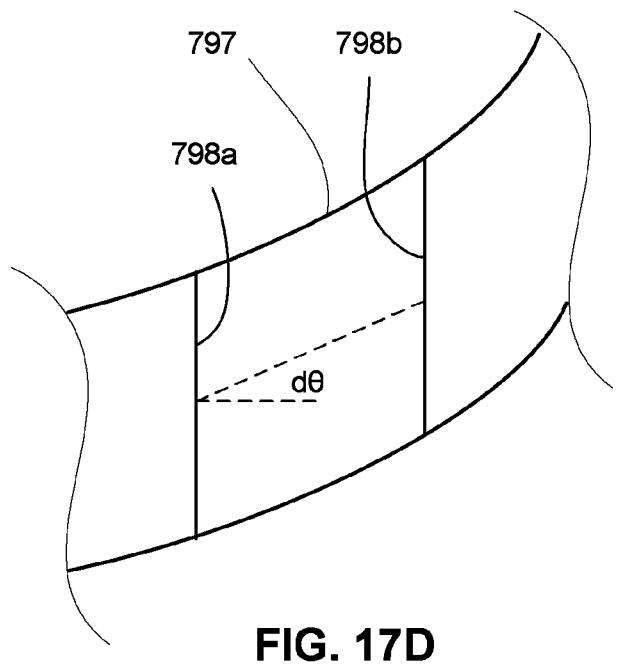
FIGS. 17D and 17E illustrate focused views of a slot of the stent embodiment of FIG. 17B, according to an embodiment.
Figure 17E:
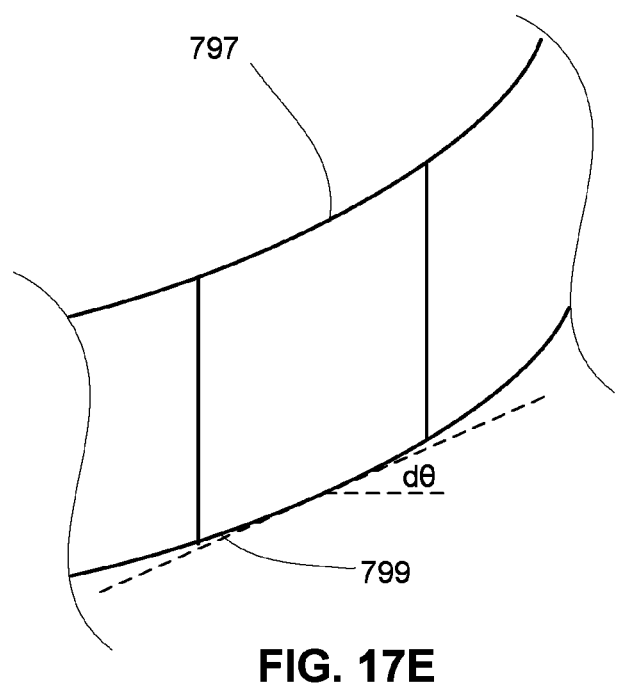

As shown in FIGS. 17D and 17E, the slot angle $d\theta$ for each slot may be measured in at least two locations. As shown in FIG. 17D, in some embodiments, the slot angle $d\theta$ is the angle between a line connecting the midpoints of sidewalls 798a, 798b of the slot 797 and a line parallel with the longitudinal axis of the stent. In other embodiments, the slot angle $d\theta$ can be measured as the angle between a tangent to a midpoint of the lower edge 799 of the slot 797 and a line parallel with the longitudinal axis of the stent, as shown in FIG. 17E.

Additionally, although the above discussion characterizes the backbone as being divided into discrete parts whose angular orientation is taken at the slots of the backbone, the angular orientation of discrete parts of the backbone can also be taken in similar fashion for those segments of the backbone extending between the slots of the backbone. As illustrated in FIG. 17B, the discrete segments extending between the slots of the backbone can be generally curvilinear and define an increasingly or decreasingly positive slope (as shown on the immediate left side of a peak along a leg of the backbone) and/or define an increasingly or decreasingly positive slope (as shown on the immediate right side of a peak along a leg of the backbone).

In some embodiments, these discrete segments can be generally curvilinear and provide the "rise" or "fall" component of the helical extension of the backbone while the slot extends generally parallel relative to the longitudinal axis of the stent. In other words, in some embodiments, only the discrete segments extending between the slots would extend in a helical direction. However, as discussed extensively herein, the incorporation of curved or curvilinear segments in some embodiments can enhance the flexibility and strength of the stent. In other embodiments, the discrete segments and the slots of the backbone can all be curvilinear or generally straight and extend in a direction generally parallel to the relative to the longitudinal axis or helically about the axis.

Stent Device Manufacture, Processes and Assembly

The overall stent device manufacturing process may include any or all of the following sub-steps in any effective operational order:

Polymer synthesis, compounding and/or mixing.
Non-polymer materials, such as a biocompatible metal material, such as a bioerodable alloy or non-bioerodable alloy. All or some parts may be metallic, and metal sheet processing steps below may be functionally equivalent to polymer oriented steps below.
Optional composite materials, e.g., reinforcing materials, drug carrier particles, and the like.
Polymer film pressing, molding and/or thermal processing.
Multi-layer film.
Drug coating of polymer film.
Cutting of parts from polymer film, e.g., laser cutting. In some embodiments, different parts of the stent may have different film composition or structure.
Industrial precision part forming methods, injection molding, 3-D printing, UV stereo-forming, and the like.
Drug coating of formed parts, e.g., anti-restenosis compound applied in polymer/solvent carrier, such as by spraying, dipping, or the like.
Pre-forming and/or molding of parts, e.g., pre-shaped backbones and rail members (see, e.g., FIGS. 18, 19A, and 19B).
Assembly of stent in semi-compacted configuration, e.g.:
 tooling to hold and manipulate parts;
 grooved mandrels to hold backbone assembly,
 insertion of rail members though slide slots;
 bonding of rail members in bond recesses or bond-slots (such as with adhesive bonding, solvent bonding, heat or energy bonding, or the like);
 trimming of excess material and/or assembly tabs from parts; and/or
 optional post-assembly treating, coating and/or polishing.
Inspection and quality control of assembled stent.
Final stent compaction and mounting on balloon catheter (e.g., iris-like uniform compaction devices, heat, pressure, fluids, vacuum and/or pressure applied to balloon, and the like).
Packaging and sterilization of stent/catheter product (e.g., E-beam Irradiation, chemical sterilization, or the like).

The stent can be made from many types of biocompatible materials. For example, polymer compositions suitable for making the stent embodiments described herein are described in published patent application US2010-0228,343, Brandom, et al.; "Phase-Separated Biocompatible Polymer Compositions For Medical Uses". See, e.g., Tables 2 and 3 of that publication, and related description, which teach the preparation and testing of a copolymers of $I_2DTE$ (di-iodo-desaminotyrosyl tyrosine ethyl ester) and PCL (polycaprolactone) of different molecular weights, such as Poly(85% I2DTE-co-8% PCL10K-co-7% PCL1.25K carbonate).

Other biocompatible materials may be employed Likewise, composite and/or layered materials may be employed. Different parts, such as rail members and backbones, may have differing polymer composition and/or different material properties (e.g., different layer structure, heat treatment or annealing history, composite content or the like). In alternative embodiments combination of polymer and metallic materials may be employed. Bioerodable metallic materials such as alloys and coated metals may be employed for the stent structure without departing from the unique and novel aspects disclosed herein. Bioerodable metallic materials may comprised magnesium, iron alloys, zinc, manganese and the like.

Figure 18:
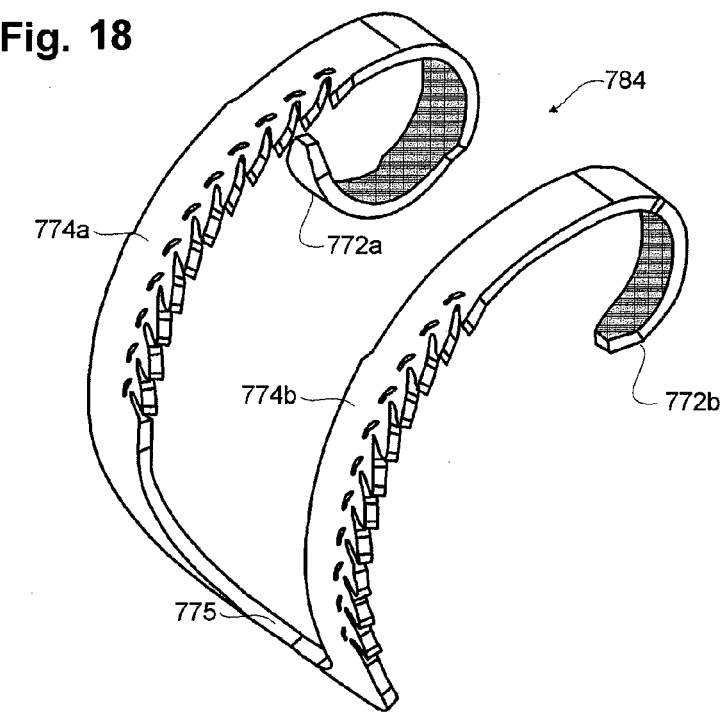
FIG. 18 illustrates a radial element having a pre-formed shape, according to an embodiment.
Figure 19A:
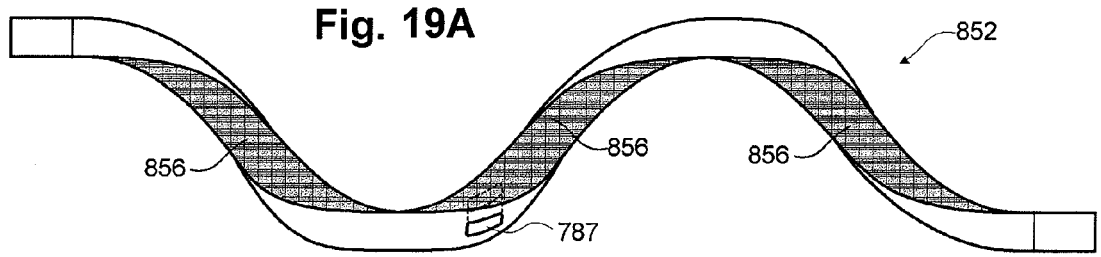
FIGS. 19A-19B illustrate embodiments of a backbone having a pre-formed shape, according to an embodiment.
Figure 19B:
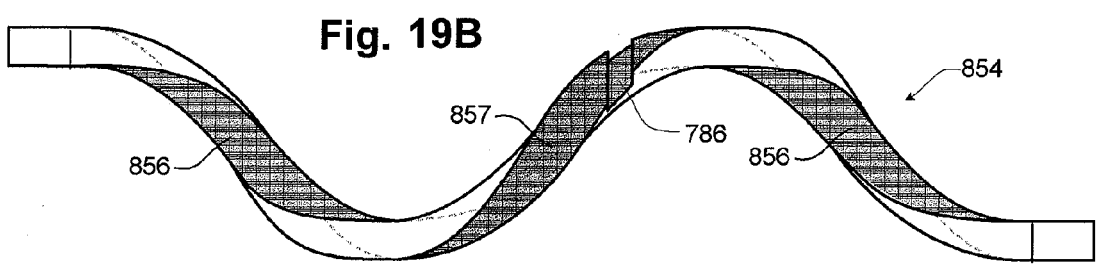

FIGS. 18, 19A, and 19B illustrate pre-formed backbone and rail member parts having a pre-formed shape between the same parts as cut from flat sheet polymer (see, e.g., FIGS. 11, 17A, and 17B) and the shape as finally assembled in a complete stent structure (such as FIGS. 13A-14B). For example, the parts may be shaped in molds or other tooling by application of pressure, heat, optionally moisture, and the like or combinations of those. Such pre-forming or pre-shaping of parts such as backbones 782 and rail members 784 may advantageously reduce or eliminate plastic deformation, residual stresses, or other changes to material properties during the process of assembling and mounting the stent. Pre-forming or pre-shaping of parts may also simplify and promote convenience in the assembly process, and promote precision in alignment of parts for bonding or the like.

FIG. 18 shows a typical rail member 784, which has been pre-formed to have an overall curvature approximating the curved surface of the tubular stent assembly, and in which the proximal rail end portions 772a and 772b have been given a greater curvature (smaller radius) approximating the curvature of these portions in the compacted stent assembly (see, e.g., FIG. 13A).

FIGS. 19A and 19B show typical backbones 852 and 854 that have been given a pre-formed shape approximating the shape in the assembled stent. The backbone 852 in FIG. 19A has a reversing helical shape (see FIGS. 14A and 14B), such that only the inside surface 856 (facing toward center of assembled stent lumen) is apparent in the plane of the drawing. In contrast, backbone 854 in FIG. 19B has a continuous helical shape, in which both inside surface 856 and outside surface 857 (facing outward from assembled stent lumen) is apparent in the plane of the drawing.

FIGS. 20A-20D show details of the assembly process of mounting rail members (e.g., 784-785 of FIGS. 12A and 12B) during assembly, which is applicable to core bonded assemblies (e.g., embodiments in which the rail member is bonded to the backbone) of the various alternative embodiments described herein. In such assemblies, the typical sequence is to pass rail members through the sliding slots of the adjacent backbone prior to fixedly mounting the rail member to its supporting backbone. In some cases, grooved or conformably-shaped mandrels are used for securing the backbones during assembly of the stent structure.

FIGS. 20A and 20B shows the preliminary step of inserting the proximal ends of the rail members 772 through the slots 787 in the adjacent backbone 782b in the direction shown by the arrow. FIGS. 20C and 20D show a subsequent step of fixedly mounting the proximal rail member ends 772 to supporting backbone 782a. In this example, an adhesive bond is formed between the rail end 772 and the surface of recess 786 using a bonding agent 860. An amount or portion of bonding agent 860 may be deposited in recess 786, followed by pressing rail end 772 down into recess 786. Specialized positioning or clamping tooling may be provided for convenience and consistency in this mounting process. In one example, a bonding agent 860 may comprise a solvent which allows the material of backbone 782 to adhere to the material of rail end 772. For example, an agent comprising methylene chloride or a similar solvent may be applied to bond polymer parts comprising a copolymer of I₂DTE and PCL. In other examples, agent 860 may comprise cross-linking or UV curable adhesive. In yet another example, energy such a locally applied heat or ultrasound may be used to bond rail 772 to backbone 782. In yet other examples, a fitting or fastener may be employed.

Testing Data of Stent Embodiments Compared to Prior Art Stents

As discussed herein, embodiments of the helical slide-and-lock stents can provide superior flexibility and stiffness compared to prior polymer stents. In this regard, various tests have shown that the stiffness of embodiments disclosed herein is greater than that of prior art polymer stents. Indeed, the structural properties, such as the stiffness, of embodiments disclosed herein more closely mimics the structural properties of metal stents.

Accordingly, embodiments of the stents disclosed herein represent a significant advance in stent technology which allows a polymer and/or composite material to be used in a configuration that provides structural properties that can approach and/or replicate the structural properties of a metal stent. Metal stents have the disadvantage of not being as bioresorbable as polymer stents; however, metal stents have long provided superior structural properties that may be needed for severe lesions, such as rigidity, stiffness, and crush strength. In contrast, prior polymer stents could provide resorbability and other benefits not available with metal stents; however, prior polymer stent were not as stiff, rigid, or strong as the metal counterparts. One of the solutions and advances made by embodiments of the stent of the present application is the provision of a manner of achieving bioresorbability and the other benefits of polymers while exhibiting superior structural properties similar to metal stents. Indeed, the unique features and configurations of the helical slide-and-lock polymer stents disclosed herein enable one of skill to obtain the benefits of polymer and metal stents. Further, the present disclosure also provides for a variety of stents having a composite material structure which can incorporate advantages of various materials.

Lamination Manufacturing Process Embodiments

Stents in accordance with embodiments can be fabricated or created using a wide variety of manufacturing methods, techniques and procedures. These include, but are not limited to, laser processing, milling, stamping, forming, casting, molding, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

In certain embodiments, stents can be fabricated by using an injection molding process, technique or method. For example, an injection molding process or the like, among others, can be used to form stent rows as integral units. The axially extending rows can then be connected and rolled into a tubular form in the collapsed state.

In some embodiments, a lamination stack can used to fabricate the stent rows by a lamination process in accordance with one embodiment. The axially extending rows can then be connected and rolled into a tubular form in the collapsed state.

The lamination stack, in some embodiments, generally can comprise three sheets or pallets which can have the desired features formed thereon, for example, by laser cutting, etching and the like. The pallets can be aligned and joined, for example, by bonding, welding and the like to form a unit. The excess material (e.g., side and end rails) can be removed to form the stent rows. The pallets can include various circumferentially nesting features such as male and female articulating and/or ratcheting designs to control and limit the diameter in collapsed and fully deployed states.

Stent Materials Generally

The stent can be fabricated from at least one or more materials. These materials include metals, polymers, composites, and shape-memory materials. In another optional embodiment, the stent further can comprise a tubular member formed from a biocompatible and preferably, bioresorbable polymer, such as those disclosed in co-pending U.S. application Ser. No. 10/952,202, the disclosure of which is incorporated herein in its entirety by reference. It is also understood that the various polymer formulae employed can include homopolymers and heteropolymers, which can include stereoisomerism, composites, filled materials, etc. Homopolymer is used herein to designate a polymer comprised of all the same type of monomers. Heteropolymer is used herein to designate a polymer comprised of two or more different types of monomer which is also called a co-polymer. A heteropolymer or copolymer can be of a kind known as block, random and alternating. Further with respect to the presentation of the various polymer formulae, products according to embodiments can be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products can be eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term "inherently radiopaque" is used herein to designate polymer that is intrinsically radiopaque due to the covalent bonding of halogen species to the polymer. Accordingly, the term does encompass a polymer which is simply blended with a halogenated species or other radiopacifying agents such as metals and their complexes.

In another optional variation, the stent further can comprise an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that can be natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, can include virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 USC 262(a)). Further the term "biological agent" can include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent can also include vitamin or mineral substances or other natural elements.

In some embodiments, the design features of the axially or circumferentially offset elements can be varied to customize the functional features of strength, compliance, radius of curvature at deployment and expansion ratio. In some embodiments, the stent can comprise a resorbable material and vanishes when its job is done. In some embodiments, the stent serves as a therapeutic delivery platform.

Some aspects are also disclosed in co-pending U.S. patent application Ser. Nos. 11/016,269, 60/601,526, 10/655,338, 10/773,756, and 10/897,235, the disclosures of each of which are incorporated herein in their entirety by reference thereto.

Some features and arrangements of embodiments of stents are disclosed in U.S. Pat. Nos. 6,033,436, 6,224,626, and 6,623,521, each issued to Steinke, the disclosures of each of which are hereby incorporated in their entirety by reference thereto.

Advantageously, the stent design elements and interlocks can be varied to customize the functional features of strength, compliance, radius of curvature at deployment and expansion ratio. In some embodiments, the stent can comprise a resorbable material and vanishes when its job is done. In some embodiments, the stent serves as a delivery platform for therapeutic agents such as pharmaceutical compounds or biological materials.

Metal Stents and Methods of Manufacturing

Possible materials for making the stents in accordance with some embodiments include cobalt chrome, 316 stainless steel, tantalum, titanium, tungsten, gold, platinum, iridium, rhodium and alloys thereof or pyrolytic carbon. In still other alternative embodiments, the stents can be formed of a corrodible material, for instance, a magnesium alloy. Although various stent embodiments have been described as being conventional balloon expandable stents, those skilled in the art will appreciate that stent constructions according to embodiments can also be formed from a variety of other materials to make a stent crush-recoverable. For example, in alternative embodiments, such as self expandable stents, shape memory alloys that allow for such, such as Nitinol and Elastinite®, can be used in accordance with embodiments.

Various methods of forming the individual elements from metal sheets can comprise laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which can be desirable to help improve engagements of lockouts. Further one can use plasma etching or other methods known in the art which are capable of producing high-resolution and polished components. The embodiments disclosed herein are not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, can be used to fasten the individual elements. Some methods allow for different front and back etch artwork, which could result in chamfered edges, which can be desirable to help improve engagements of lockouts. In an advantageous method of manufacture, the components of the stent can be heat set at various desired curvatures. For example, the stent can be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent cannot outlive its usefulness within the vessel. Moreover, a bioresorbable stent could potentially be used to deliver a greater dose of a therapeutic agent, deliver multiple therapeutic agents at the same time or at various times of its life cycle, to treat specific aspects or events of vascular disease. Additionally, a bioresorbable stent can also allow for repeat treatment of the same approximate region of the blood vessel. Accordingly, there remains an important unmet need to develop temporary (i.e., bioresorbable and/or radiopaque) stents, wherein the polymeric materials used to fabricate these stents can have the desirable qualities of metal (e.g., sufficient radial strength and radiopacity, etc.), while circumventing or alleviating the many disadvantages or limitations associated with the use of permanent metal stents.

In some embodiments, the stent can be formed from biocompatible polymers that are bio-resorbable (e.g., bio-erodible or bio-degradable). Bio-resorbable materials can be preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. For additional information, see U.S. Pat. Nos. 4,980,449, 5,140,094, and 5,264,537, the disclosures of each of which are incorporated by reference herein.

In one mode, the degradable materials can be selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, polyalkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul., 2004) Ratner, Hoffman, Schoen, and Lemons; and Atala, A., Mooney, D. Synthetic Biodegradable Polymer Scaffolds. 1997 Birkhauser, Boston; each of which are incorporated herein by reference).

Further still, in another embodiment, the stents can be formed of a polycarbonate material, such as, for example, tyrosine-derived polycarbonates, tyrosine-derived polyarylates, tyrosine-derived diphenol monomers, iodinated and/or brominated tyrosine-derived polycarbonates, iodinated and/or brominated tyrosine-derived polyarylates. For additional information, see U.S. Pat. Nos. 5,099,060, 5,198,507, 5,587,507, which was resiussed in U.S. Pat. Nos. RE37,160, 5,670,602, which was resiussed in U.S. Pat. Nos. RE37,795, 5,658,995, 6,048,521, 6,120,491, 6,319,492, 6,475,477, 5,317,077, and 5,216,115, and U.S. application Ser. No. 09/350,423, the disclosures of each of which are incorporated by reference herein. In yet another embodiment, the polymer can be any of the biocompatible, bioabsorbable, radiopaque polymers disclosed in: U.S. Patent Application Nos. 60/852,513, 60/852,471, 60/601,526, 60/586,796, 60/866,281, 60/885,600, 10/952,202, 11/176,638, 11/335,771, 11/200,656, 11/024,355, 10/691,749, 11/418,943, and 11/873,362; U.S. Patent Publication No. US26115449A1; U.S. Pat. Nos. 6,852,308 and 7,056,493; and PCT Application Nos. PCT/US2005/024289, PCT/US2005/028228, PCT/US07/01011, and PCT/US07/81571, the disclosures of each of which are incorporated herein by reference thereto.

Natural polymers (biopolymers) include any protein or peptide. Biopolymers can be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers can be used to fabricate stents constructed according to embodiments. Suitable shape-shifting polymers can be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. Nos. 6,160,084 and 6,284,862, the disclosures of each of which are incorporated by reference herein. For additional disclosure on shape memory polymers, see U.S. Pat. Nos. 6,388,043 and 6,720,402, the disclosures of each of which are incorporated by reference herein. Further the transition temperature can be set such that the stent can be in a collapsed condition at a normal body temperature. However, with the application of heat during stent placement and delivery, such as via a hot balloon catheter or a hot liquid (e.g., saline) perfusion system, the stent can expand to assume its final diameter in the body lumen. When a thermal memory material is used, it can provide a crush-recoverable structure.

Further still, stents can be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers can comprise or contain any example of thermoplastics, such as the following, among others: fluorinated ethylene-propylene, poly(2-hydroxyethyl methacrylate) (aka pHEMA), poly(ethylene terephthalate) fiber (aka Dacron®) or film (Mylar®), poly(methyl methacrylate) (aka PMMA), Poly(tetrafluoroethylene) (aka PTFE and ePTFE and Gore-Tex®), poly(vinyl chloride), polyacrylates and polyacrylonitrile (PAN), polyamides (aka Nylon), polycarbonates and polycarbonate urethanes, polyethylene and poly(ethylene-co-vinyl acetate), polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Finally, the polymer(s) utilized in embodiments of the stent can be fabricated according to any variety of processes, such as those discussed in U.S. Patent Application Nos. 60/852,471 and 60/852,513, and U.S. Pat. Nos. 5,194,570, 5,242,997, 6,359,102, 6,620,356, and 6,916,868, the disclosures of each of which are incorporated by reference herein.

Methods of Manufacturing and Assembling Polymeric Stents

Where plastic and/or degradable materials are used, the elements can be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain embodiments with the disclosed polymers can be shaped into stents via combinations of two or more thereof, and the like.

Such processes can further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, the disclosure of which is incorporated by reference herein.

Stents of some of the embodiments can be manufactured with elements prepared in full stent lengths or in partial lengths of which two or more are then connected or attached. If using partial lengths, two or more can be connected or attached to comprise a full length stent. In this arrangement the parts can be assembled to give rise to a central opening. The assembled full or partial length parts and/or modules can be assembled by inter-weaving them in various states, from a collapsed state, to a partially expanded state, to an expanded state.

Further, elements can be connected or attached by solvent or thermal bonding, or by mechanical attachment. If bonding, advantageous methods of bonding comprise the use of ultrasonic, radiofrequency or other thermal methods, and by solvents or adhesives or ultraviolet curing processes or photoreactive processes. The elements can be rolled by thermal forming, cold forming, solvent weakening forming and evaporation, or by preforming parts before linking.

Rolling of the flat series of module(s) to form a tubular member can be accomplished by any means known in the art, including rolling between two plates, which can be each padded on the side in contact with the stent elements. One plate can be held immobile and the other can move laterally with respect to the other. Thus, the stent elements sandwiched between the plates can be rolled about a mandrel by the movement of the plates relative to one another. Alternatively, 3-way spindle methods known in the art can also be used to roll the tubular member. Other rolling methods that can be used in accordance with certain embodiments include those used for "jelly-roll" designs, as disclosed for example, in U.S. Pat. Nos. 5,421,955, 5,441,515, 5,618,299, 5,443,500, 5,649,977, 5,643,314 and 5,735,872, the disclosures of each of which are incorporated herein in their entireties by reference thereto.

The construction of the slide-and-lock stents in these fashions can provide a great deal of benefit over the prior art. The construction of the locking mechanism can be largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In some embodiments, the frequency of catches, stops or teeth present on selected circumferential elements can prevent unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity can be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platinum, iridium, and rhodium. In some embodiments, a halogen such as iodine and/or bromine can be employed for its radiopacity and antimicrobial properties.

Multi-Material Vascular Prosthesis

In still other alternative embodiments, various materials (e.g., metals, polymers, ceramics, and therapeutic agents) can be used to fabricate stent embodiments. The embodiments can comprise: 1) differentially layered materials (through stacking in the vertical or radial axis) to create a stack of materials (materials can be stacked in any configuration, e.g., parallel, staggered, etc.); 2) spatially localized materials which can vary along the long axis and/or thickness of the stent body; 3) materials that are mixed or fused to create a composite stent body (e.g., whereby a therapeutic agent(s) is within the stent body with a polymer); 4) embodiments whereby a material can be laminated (or coated) on the surface of the stent body (see Stent Surface Coatings with Functional Properties as well as see Therapeutic Agents Delivered by Stents); and, 5) stents comprised of 2 or more parts where at least one part can be materially distinct from a second part, or any combination thereof.

The fashioning of a slide-and-lock multi-material stent can have between two or more materials. Thickness of each material can vary relative to other materials. This approach as needed or desired allows an overall structural member to be built with each material having one or more functions contributing towards enabling prosthesis function which can include, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which can impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials can comprise loadbearing properties, elastomeric properties, mechanical strength that can be specific to a direction or orientation e.g., parallel to another material and/or to the long axis of the stent, or perpendicular or uniform strength to another material and/or stent. The materials can comprise stiffeners, such as the following, boron or carbon fibers, pyrolytic carbon. Further, stents can be comprised of at least one re-enforcement such a fibers, nanoparticles or the like.

In another implementation of some embodiments, the stent can be made, at least in part, from a polymeric material, which can be degradable. The motivation for using a degradable stent can be that the mechanical support of a stent can only be necessary for several weeks. In some embodiments, bioresorbable materials with varying rates of resorption can be employed. For additional information, see U.S. patent application Ser. Nos. 10/952,202 and 60/601,526, the disclosures of each of which are incorporated by reference herein. Degradable polymeric stent materials can be particularly useful if it also controls restenosis and thrombosis by delivering pharmacologic agents. Degradable materials can be well suited for therapeutic delivery (see Therapeutic Agents Delivered by Stents).

In some embodiments, the materials can comprise or contain any class of degradable polymer as previously defined. Along with variation in the time of degradation and/or resorption the degradable polymer can have other qualities that are desirable. For example, in some embodiments the materials can comprise or contain any example of natural polymers (biopolymers) and/or those that degrade by hydrolytic and/or enzymatic action. In some embodiments, the material can comprise or contain any example of hydrogels that can or cannot be thermally reversible hydrogels, or any example of a light or energy curable material, or magnetically stimulateable (responding) material. Each of these responses can provide for a specific functionality.

In some embodiments, the materials can comprise or be made from or with constituents which can have some radiopaque material alternatively, a clinically visible material which can be visible by x-ray, fluoroscopy, ultrasound, MRI, or Imatron Electron Beam Tomography (EBT).

In some embodiments, one or more of the materials can emit predetermined or prescribed levels of therapeutic radiation. In an embodiment, the material can be charged with beta radiation. In another embodiment, the material can be charged with Gamma radiation. In yet another embodiment, the material can be charged with a combination of both Beta and Gamma radiation. Stent radioisotopes that can be used include, but are not limited to, 103Pd and 32P (phosphorus-32) and two neutron-activated examples, 65Cu and 87Rb2O, (90)Sr, tungsten-188 (188).

In some embodiments, one or more of the materials can comprise or contain a therapeutic agent. The therapeutic agents can have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells can serve as a limited release system. For additional concepts of therapeutic delivery, see the section entitled: Therapeutic Agents Delivered by Stents.

Therapeutic Agents Delivered by Stents

In another implementation, the stent further can comprise an amount of a therapeutic agent (as previously defined for a pharmaceutical agent and/or a biologic agent) sufficient to exert a selected therapeutic effect. The material of at least a portion of the stent itself can comprise at least one therapeutic agent, or at least one therapeutic agent can be added to the stent in a subsequent forming process or step. In some embodiments of the stent (e.g., polymer stents and multi-material stents), the therapeutic agent can be contained within the stent as the agent is blended with the polymer or admixed by other means known to those skilled in the art.

For example, one or more therapeutic agents can be delivered through a multi-material vascular prosthesis. In some embodiments, the entire stent can be formed from materials comprising one or more therapeutic agents. In other embodiments, portions of the stent, such as individual components thereof, can comprise materials comprising one or more therapeutic agents. In such embodiments, it is contemplated that the therapeutic agent(s) can be released as the stent material degrades.

For example, the therapeutic agent can be embedded or impregnated into the film by means of a combination of solvent casting and thermal pressing. In such a method, the film can be formed from a mixture of the polymer and the therapeutic agent (20% solids polymer, for example poly (90% DTE-co-10% DT carbonate), which can be made with 1% rapamycin in dichloromethane). Once this mixture is prepared, the film can be cast using a doctor blade. Alternatively, the film can be formed by using a mechanical reverse roll coater or other solvent-based film caster. Once the film is cast, the solvent can be evaporated off using a vacuum oven, e.g., for a period of time and at a temperature suitable for the polymer and drug, such as at 40° C. for at least 20 hours. Once the film is dried, it can be thermally pressed, e.g., at a temperature of 100° C. between two heated platens of a hydraulic press. This allows the potency of the drug to be retained.

In addition, the therapeutic agent can be embedded or impregnated into the film using only a solvent or by spin casting. Once a therapeutic agent is selected, one needs to determine if the solvent is compatible with the agent and the polymer chosen. The objective is to prepare a suitable sprayable suspension. Additionally, the stability of the drug can be measured such that the therapeutic agent can remain active while in the coating as well under physiological conditions once released from the film. This can be determined by those skilled in the art who conduct standard in vitro elution studies (see Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials & Artificial Organs, Vol. 19(2), 88-92 (2006), http://medind.nic.in/taa/t06/i1/taat06i1p88.pdf) of agent embedded films and through the use of analytical methods such as HPLC methods (see Dhanikula et al., *Development and Characterization of Biodegradable Chitosan Films for Local Delivery of Paclitaxel*; and Kothwala et al., *Paclitaxel Drug Delivery from Cardiovascular Stent*) to detect the purity of the drug.

In other embodiments, at least one therapeutic agent can be added to the stent and/or its components after the formation of the stent and/or its components. For example, at least one therapeutic agent can be added to individual stent components, through a coating process or otherwise. The addition of at least one therapeutic agent can occur before or after cutting or lasing of the stent components. In another example, at least one therapeutic agent can also be added to at least a portion of the stent after partial or full assembly thereof, through a coating process or otherwise. In some embodiments of the stent, the therapeutic agent can be delivered from a polymer coating on the stent surface. In other embodiments of the stent, a therapeutic agent can be localized in or around a specific structural aspect of the device.

For example, the therapeutic agent can be delivered from a polymer coating on the stent surface. Thus, the stent can be made by applying the therapeutic agent to a stent component before the stent is assembled or formed. In this regard, the stent component can be created from a polymer sheet, such as a flat polymer film. Thus, at least one stent component can be separated from a remainder or excess portion of the film either before or after the therapeutic agent has been applied to the stent component and/or film. After the therapeutic agent is applied and the stent component is separated from the film, the stent component can be assembled (and in some embodiments, with other stent components) to form a stent therefrom.

In some embodiments, the stent can be prepared with the following preparation method. The stent can be initially prepared by creating a pattern of a stent component on a flat polymer film. The creation of the pattern on the film can occur before or after application of a therapeutic agent thereto, as discussed below. The pattern of the stent component can be created on the film such that the stent component can be detached from the film when desired. In some embodiments, the pattern can be created using a laser to lase the pattern onto the film. Additionally, the lased pattern can be of any given stent component design, such as that used in a slide and lock stent design. After the pattern is created on the film, the entire film can be cleaned. For example, if the therapeutic agent has not yet been applied to the film, the entire lased film can be immersed into a cleaning solution that is compatible with the specific type of polymer from which the film is made. The cleaned film can then be dried, for example, by being blown and oven dried.

A coating formulation can be prepared by dissolving or dispersing the polymer and the therapeutic agent(s) of choice and solvent(s) or other compatible excipient(s) using a calculated amount of each component to achieve the desired concentration. The coating formulation can then be applied to the lased polymer film using one or more coating methods. For example, the film may be coated by means of spraying, dipping, or other coating methods. Additionally cross-linking reagents may also be used to prepare a coating.

In a spraying coating method, the lased polymer films can be coated with the coating formulation by first mounting the cleaned dried films into a spray apparatus. The coating formulation can then be sprayed onto the film, and the film can be rotated 180 degrees such that the other side can be coated if desired. This method can allow for coating of one or both sides of the stent component(s). This method can also allow one to apply different therapeutic agents per side of the lased film and/or stent component and to selectively coat regions thereof. The method can further allow one to coat multiple drugs per film and/or stent component. Alternative coating methods can allow for other similar benefits.

For example, a therapeutic agent can be coated onto a film or stent component as in the following illustration. First, the therapeutic agent in this example is a Polymer-Paclitaxel Formulation, such as a 0.5% [25% Paclitaxel/75% Poly (86.75% I2DTE-co-10% I2DT-co-3.25% PEG2000 carbonate)] in tetrahydrofuran (THF), which can be prepared using an analytical balance. In order to do so, one must first weigh 0.0150 g of Paclitaxel into a tared vial. Then weigh 0.0450 g of polymer into another vial. Next, weigh 11.940 g of THF into each vial. Shake the vials on a laboratory shaker, such as a Roto-genie, for at least one hour. In this example, coating can be achieved using a spray gun apparatus, such as an air brush (see Westedt, U., *Biodegradable Paclitaxel-loaded Nanoparticles and Stent Coatings as Local Delivery Systems for the Prevention of Restenosis—Dissertation*, Marburg/Lahn (2004), http://deposit.ddb.de/cgi-bin/dokserv?idn=972868100&dokvar=dl&dokext=pdf&filename=972868100.pdf; and Berger, H. L. *Using Ultrasonic Spray Nozzles to Coat Drug-Eluting Stents*, Medical Device Technology (2006), http://www.devicelink.com/mdt/archive/06/11/004.html). Typically, the spray gun apparatus should first be cleaned with THF. In order to do so, a syringe can be filled with at least 10 ml of THF. The syringe can then be attached to a spray line attached to the spray gun. Gradually, the 10 ml of THF can be pushed from the syringe into the spray gun without N2 pressure. This can be repeated as necessary to ensure that the line is washed clean. The syringe pump can then be set up with the syringe containing the Polymer-Paclitaxel Formulation.

Next, a film, which can be either lased or unlased, can be placed into a hooded environment and mounted or clipped into a holder. If necessary, the surfaces of the film can be cleaned of lint and dust using a pure air or gas source or equivalent. For consistent coating quality, the film can be programmed to move at a set rate (distance and speed) relative to a spray stream by integrating the film holder apparatus with a motion control system. Manual coating without the motion control can also be used to achieve a coating. The spray gun can also be set to direct the spray to only a given location to control coating distribution.

In some embodiments, to coat both sides of the film uniformly, the spray cycle can start with the spray hitting at the bottom corner of the film, and the motion control should move the film incrementally as it traverses back and forth in front of the spray nozzle. The system can then move the film back to the start position so the spray is directed at the bottom. The film holder can be turned 180 degrees and the cycle can be repeated to coat the second side. After coating, the film holder can be removed with the film and the film can be dried in a vacuum oven at a temperature suitable for the drug and polymer, e.g., 25°±5° C. for at least 20 hours.

Other methods and teachings related to impregnation or coating processes are found in the following references, the entirety of each of which is hereby incorporated by reference herein: Westedt, U., *Biodegradable Paclitaxel-loaded Nanoparticles and Stent Coatings as Local Delivery Systems for the Prevention of Restenosis—Dissertation*, Marburg/Lahn (2004), http://depositddb.de/cgi-bin/dokserv?idn=972868100&dokvar=dl&dokext=pdf&filename=972868100.pdf; Berger, H. L. Using Ultrasonic Spray Nozzles to Coat Drug-Eluting Stents, Medical Device Technology (2006), http://www.devicelink.com/mdt/archive/06/11/004.html; Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials & Artificial Organs, Vol. 19(2), 88-92 (2006), http://medind.nic.in/taa/t06/i1/taat06i1p88.pdf.

After the film is coated using a given coating method, the film can be given time to dry. Once dried, the lased, coated stent component(s) can be separated from the remainder of the film. Care should be taken to not disturb the surfaces of the coated stent component(s) when being detached from the film and assembled or knitted together to form a three-dimensional cylindrical stent.

In another variation the therapeutic agent can be delivered by means of a non-polymer coating. In other embodiments of the stent, the therapeutic agent can be delivered from at least one region or one surface of the stent. The therapeutic agent can be chemically bonded to the polymer or carrier used for delivery of the therapeutic from at least one portion of the stent and/or the therapeutic can be chemically bonded to the polymer that can comprise at least one portion of the stent body. In some embodiments, a polymer can be used as a component of the coating formulation. Accordingly, the coating can essentially bond directly to a clean lased film and/or stent component, which can also be comprised of a polymer. Such an embodiment of the method can provide for a seamless interface between the coating and the lased film and/or stent component. Further, in another embodiment, more than one therapeutic agent can be delivered.

The amount of the therapeutic agent can be preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) can be selected from the group consisting of antiproliferative agents, anti-inflammatory, anti-matrix metalloproteinase, and lipid lowering, cholesterol modifying, anti-thrombotic and antiplatelet agents, in accordance with some embodiments. For vascular stent applications, some anti-proliferative agents that improve vascular patency include without limitation paclitaxel, Rapamycin, ABT-578, Biolimus A9, everolimus, dexamethasone, nitric oxide modulating molecules for endothelial function, tacrolimus, estradiol, mycophenolic acid, C6-ceramide, actinomycin-D and epothilones, and derivatives and analogs of each.

Some agents act as an antiplatelet agent, antithrombin agent, compounds to address other pathologic events and/or vascular diseases. Various therapeutic agents can be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents can include other pharmaceutical and/or biologic agents intended for purposes of treating body lumens other than arteries and/ or veins). Therapeutic agents can be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments can be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents can be useful for expanding an obstructed lumen and for inducing an obstruction (e.g., as in the case of aneurysms).

Therapeutic release can occur by controlled release mechanisms, diffusion, interaction with another agent(s) delivered by intravenous injection, aerosolization, or orally. Release can also occur by application of a magnetic field, an electrical field, or use of ultrasound.

Stent Surface Coatings with Functional Properties

In addition to stents that can deliver a therapeutic agent, for instance delivery of a biological polymer on the stent such as a repellant phosphorylcholine, the stent can be coated with other bioresorbable polymers predetermined to promote biological responses in the body lumen desired for certain clinical effectiveness. Further the coating can be used to mask (temporarily or permanently) the surface properties of the polymer used to comprise the stent embodiment. The coating can be selected from the broad class of any biocompatible bioresorbable polymer which can include any one or combination of halogenated and/or non-halogenated which can or cannot comprise any poly(alkylene glycol). These polymers can include compositional variations including homopolymers and heteropolymers, stereoisomers and/or a blend of such polymers. These polymers can include for example, but are not limited to, polycarbonates, polyarylates, poly(ester amides), poly(amide carbonates), trimethylene carbonate, polycaprolactone, polydioxane, polyhydroxybutyrate, polyhydroxyvalerate, polyglycolide, polylactides and stereoisomers and copolymers thereof, such as glycolide/lactide copolymers. In an embodiment, the stent can be coated with a polymer that exhibits a negative charge that repels the negatively charged red blood cells' outer membranes thereby reducing the risk of clot formation. In another embodiment, the stent can be coated with a polymer that exhibits an affinity for cells, (e.g., endothelial cells) to promote healing. In yet another embodiment, the stent can be coated with a polymer that repels the attachment and/or proliferation of specific cells, for instance arterial fibroblasts and/or smooth muscle cells in order to lessen restenosis and/or inflammatory cells such as macrophages.

Described above are embodiments that can be modified with a coating to achieve functional properties that support biological responses. Such coatings or compositions of material with a therapeutic agent can be formed on stents or applied in the process of making a stent body via techniques such as dipping, spray coating, cross-linking combinations thereof, and the like, as mentioned and described above. Such coatings or compositions of material can also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In accordance with an aspect of certain embodiments, a stent would have a coating applied that can alter the physical characteristics of the stent, such as to provide specific mechanical properties to the stent. The properties can include inter alia thickness, tensile strength, glass transition temperature, and surface finish. The coating can be preferably applied prior to final crimping or application of the stent to the catheter. The stent can then be applied to the catheter and the system can have either heat or pressure or both applied in a compressive manner. In the process, the coating can form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

From the foregoing description, it will be appreciated that a novel approach for expanding a lumen has been disclosed. While several components, techniques and aspects have been described with a certain degree of particularity, it is manifest that many changes can be made in the specific designs, constructions and methodology herein above described without departing from the spirit and scope of this disclosure.

The methods which are described and illustrated herein are not limited to the sequence of acts described, nor are they necessarily limited to the practice of all of the acts set forth. Other sequences of acts, or less than all of the acts, or simultaneous occurrence of the acts, can be utilized in practicing embodiments.

While a number of embodiments and variations thereof have been described in detail, other modifications and methods of using and medical applications for the same will be apparent to those of skill in the art. Accordingly, it should be understood that various applications, modifications, materials, and substitutions can be made of equivalents without departing from the unique and novel last next disclosed herein or the scope of the claims.

References

Some of the references cited herein are listed below, the entirety of each one of which is hereby incorporated by reference herein:

Charles R, Sandirasegarane L, Yun J, Bourbon N, Wilson R, Rothstein R P, et al., Ceramide-Coated Balloon Catheters Limit Neointimal Hyperplasia after Stretch Injury in Carotid Arteries, Circulation Research 2000; 87(4): 282-288.

Coroneos E, Martinez M, McKenna S, Kester M., Differential regulation of sphingomyelinase and ceramidase activities by growth factors and cytokines. Implications for cellular proliferation and differentiation, J Biol. Chem. 1995; 270(40): 23305-9.

Coroneos E, Wang Y, Panuska J R, Templeton D J, Kester M., Sphingolipid metabolites differentially regulate extracellular signal-regulated kinase and stress-activated protein kinase cascades, Biochem J. 1996; 316 (Pt 1): 13-7.

Jacobs L S, Kester M., Sphingolipids as mediators of effects of platelet-derived growth factor in vascular smooth muscle cells, Am. J. Physiology 1993; 265 (3 Pt 1): C740-7.

Tanguay J F, Zidar J P, Phillips H R, 3rd, Stack RS, Current status of biodegradable stents, Cardiol. Clin. 1994; 12(4): 699-713.

Nikol S, Huehns T Y, Hofling B., Molecular biology and post-angioplasty restenosis, Atherosclerosis 1996; 123 (1-2): 17-31.

Buddy D. Ratner, Allan S. Hoffman, Frederick J. Schoen, And Jack E. Lemons, Biomaterials Science An Introduction to Materials in Medicine (Elsevier Academic Press 2004).

What is claimed is:

1. An expandable slide and lock stent, the stent comprising a tubular member having a circumference and a longitudinal axis, the stent comprising:
   a first backbone and a second backbone, the first and the second backbones each having a reversing helical shape, a first part of the shape extending in a clockwise circumferential direction and reversing into a second part of the shape, the second part extending in a counterclockwise circumferential direction, the first and second backbones extending along at least a portion of the circumference and along the longitudinal axis;
   a rail member defining proximal and distal ends, the proximal end of the rail member being coupled to the first backbone, the distal end of the rail member extending from the first backbone in the circumferential direction, the rail member configured to engage with an engagement element in the second backbone; and
   wherein the rail member is configured to provide one-way movement of the second backbone away from the first backbone such that the tubular member can be expanded between a collapsed diameter and an expanded diameter.

2. The stent of claim 1, wherein the reversing helical shape comprises a curvilinear shape.

3. The stent of claim 1, wherein the reversing helical shape comprises a sinusoidal shape.

4. The stent of claim 1, wherein the reversing helical shape comprises at least one portion having a positively trending slope and at least one portion having a negatively trending slope.

5. The stent of claim 4, wherein at least one of the portions having a positively trending slope and a negatively trending slope further comprises a plurality of generally sinusoidal wave forms.

6. The stent of claim 5, wherein the plurality of waves comprise a plurality of continuous curves.

7. The stent of claim 1, wherein the reversing helical shape of the first and second backbones comprises a sub-pattern wave form extending at least partially along at least one of the first and second backbones.

8. The stent of claim 7, wherein the second backbone comprising a plurality of engagement elements each defined by a respective pair of sidewalls, wherein at least one of the engagement elements defines an engagement element angle between about 0 degrees and about 60 degrees, the engagement element angle being measured between a line connecting midpoints of the sidewalls of the at least one engagement element and a line parallel with the longitudinal axis.

9. The stent of claim 8, wherein the at least one of the engagement elements comprises a slot.

10. The stent of claim 1, wherein an intersection of the rail member and the second backbone is at an oblique angle.

11. The stent of claim 1, further comprising second and third rail members defining proximal and distal ends, the proximal end of each of the second and third rail members being coupled to the first backbone, the distal end of each of the second and third rail members extending from the first backbone in the circumferential direction and configured to intersect and pass through one of a plurality of slots in the second backbone.

12. The stent of claim 11, wherein one or more of the slots in the second backbone define a slot angle, wherein the slot angle extends skew relative to the longitudinal axis.

13. The stent of claim 12, wherein each of the slots is disposed at a different angle with respect to the longitudinal axis compared to the slots that are adjacent.

14. The stent of claim 1, wherein the first and second backbones are reversing helical backbones defining a generally curvilinear sub-form extending along the backbones between a peak and a valley of the reversing helical backbones.

15. The stent of claim 1, wherein the rail member comprises one or more teeth for engaging the slot to provide one-way expansion of the stent.

16. The stent of claim 15, wherein the slot comprises a central passage and at least one internal recess for engaging the teeth of the rail member.

17. A method for forming the stent of claim 16, comprising forming the central passage as a first through hole in the backbone in a circumferential direction of stent, and forming the at least one internal recess as a second through hole in the backbone in a direction transverse to the circumferential direction of the central passage such that the first and second through holes partially overlap.

18. An expandable slide and lock stent, the stent comprising a tubular member having a circumference and a longitudinal axis, the stent comprising:
   a first backbone and a second backbone, the first and the second backbones each having a reversing helical shape in which a part of the shape spirals in a clockwise circumferential direction and another part of the shape spirals in a counterclockwise circumferential direction, the first and second backbones extending along at least a portion of the circumference and along the longitudinal axis;
   wherein the reversing helical shape of the first and second backbones each comprise a first wave having a first frequency, a first amplitude, a first portion with a positively trending slope, and a second portion with a negatively trending slope;
   wherein at least one of the first and second portions comprise a plurality of second waves having a second frequency and a second amplitude, the second frequency being greater than the first frequency and the second amplitude being less than the first amplitude; and
   a rail member defining proximal and distal ends, the proximal end of the rail member being coupled to the first backbone, the distal end of the rail member extending from the first backbone in the circumferential direction, the rail member configured to engage with an engagement element in the second backbone;
   wherein the rail member is configured to provide one-way movement of the second backbone away from the first backbone such that the tubular member can be expanded between a collapsed diameter and an expanded diameter.

19. The stent of claim 18, wherein each of the waves in the plurality of second waves are generally identical.

20. The stent of claim 18, wherein each of the first and second portions comprise the plurality of second waves.

21. The stent of claim 18, wherein the second backbone comprising a plurality of engagement elements each defined by a respective pair of sidewalls, wherein at least one of the engagement elements defines an engagement element angle between about 0 degrees and about 60 degrees, the engagement element angle being measured between a line connecting midpoints of the sidewalls of the at least one engagement element and a line parallel with the longitudinal axis.

22. An expandable slide and lock stent, the stent comprising a tubular member having a circumference and a longitudinal axis, the stent comprising:

a first backbone and a second backbone, the first and the second backbones each having a reversing helical shape, wherein the shape alternatingly reverses from a clockwise circumferential direction to a counterclockwise circumferential direction, and comprising at least one portion having a positively trending slope and at least one portion having a negatively trending slope, the first and second backbones extending along at least a portion of the circumference and along the longitudinal axis;

wherein at least one of the portions having a positively trending slope and a negatively trending slope further comprises a plurality of wave forms;

wherein each of the portions further comprises a plurality of slots, each of the slots being disposed at a different angle with respect to the longitudinal axis compared to the slots that are adjacent on the same portion; and a rail member defining proximal and distal ends, the proximal end of the rail member being coupled to the first backbone, the distal end of the rail member extending from the first backbone in the circumferential direction, the rail member configured to engage with an engagement element in the second backbone;

wherein the rail member is configured to provide one-way movement of the second backbone away from the first backbone such that the tubular member can be expanded between a collapsed diameter and an expanded diameter.

* * * * *